United States Patent
Hariri et al.

(10) Patent No.: US 9,216,200 B2
(45) Date of Patent: *Dec. 22, 2015

(54) TUMOR SUPPRESSION USING HUMAN PLACENTAL PERFUSATE AND HUMAN PLACENTA-DERIVED INTERMEDIATE NATURAL KILLER CELLS

(75) Inventors: Robert J. Hariri, Bernardsville, NJ (US); Mohammad A. Heidaran, Chatham, NJ (US); Lin Kang, Edison, NJ (US); Neerav Dilip Padliya, Scotch Plains, NJ (US); Ajai Pal, Bridgewater, NJ (US); Vanessa Voskinarian-Berse, Millington, NJ (US); Andrew Zeitlin, Basking Ridge, NJ (US); Xiaokui Zhang, Livingston, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,612

(22) Filed: Aug. 13, 2012

(65) Prior Publication Data

US 2014/0093488 A1 Apr. 3, 2014

Related U.S. Application Data

(63) Continuation of application No. 12/240,956, filed on Sep. 29, 2008, now Pat. No. 8,263,065.

(60) Provisional application No. 61/090,555, filed on Aug. 20, 2008, provisional application No. 60/995,763, filed on Sep. 28, 2007.

(51) Int. Cl.
| | |
|---|---|
| *A01N 63/00* | (2006.01) |
| *A61K 35/17* | (2015.01) |
| *A61K 35/50* | (2015.01) |
| *C12N 5/0783* | (2010.01) |
| *A61K 35/12* | (2015.01) |

(52) U.S. Cl.
CPC ............... *A61K 35/17* (2013.01); *A61K 35/50* (2013.01); *C12N 5/0646* (2013.01); *A61K 2035/124* (2013.01)

(58) Field of Classification Search
None
See application file for complete search history.

(56) References Cited

U.S. PATENT DOCUMENTS

| | | |
|---|---|---|
| 3,862,002 A | 1/1975 | Sanders |
| 4,798,824 A | 1/1989 | Belzer et al. |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,356,373 A | 10/1994 | Dracker et al. |
| 5,372,581 A | 12/1994 | Anderson |
| 5,415,665 A | 5/1995 | Hessel et al. |
| 5,436,151 A | 7/1995 | McGlave et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,580,777 A | 12/1996 | Bernard |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson |
| 5,709,854 A | 1/1998 | Griffith-Cima et al. |
| 5,716,616 A | 2/1998 | Prockop et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Alici et al., "Autologous antitumor activity by NK cells expanded from myeloma patirents using GMP-compliant components," Blood 111:3155-3162 (2008).

(Continued)

*Primary Examiner* — Sean Aeder
(74) *Attorney, Agent, or Firm* — Jones Day

(57) ABSTRACT

Provided herein are placental perfusate, placental perfusate cells, and placenta-derived intermediate natural killer cells, and combinations thereof. Also provided herein are compositions comprising the same, and methods of using placental perfusate, placental perfusate cells, and placenta-derived intermediate natural killer cells, and combinations thereof, to suppress the growth or proliferation of tumor cells, cancer cells, and the like, and to treat individuals having tumor cells.

31 Claims, 12 Drawing Sheets

(56) References Cited

U.S. PATENT DOCUMENTS

Figure 1:
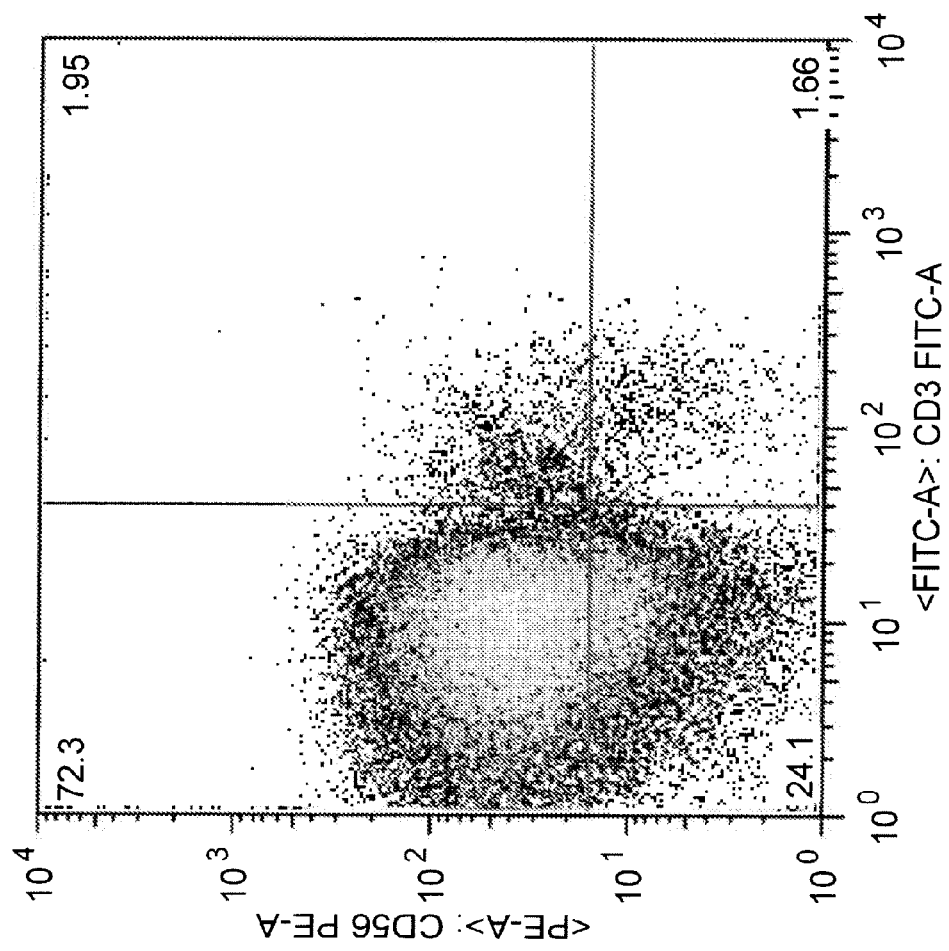

| | | |
|---|---|---|
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Brauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,102,871 A | 8/2000 | Coe |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,615 B1 | 10/2002 | Srivastava |
| 6,461,645 B1 | 10/2002 | Boyse et al. |
| 6,497,875 B1 | 12/2002 | Sorrell et al. |
| 6,534,084 B1 | 3/2003 | Vyakarnam et al. |
| 6,541,024 B1 | 4/2003 | Kadiyala et al. |
| 6,548,299 B1 | 4/2003 | Pykett |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 6,916,655 B2 | 7/2005 | Yasumoto |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,202,703 B2 | 6/2012 | Edinger et al. |
| 8,263,065 B2 * | 9/2012 | Hariri et al. .................. 424/93.1 |
| 8,545,833 B2 | 10/2013 | Hariri |
| 8,562,973 B2 | 10/2013 | Edinger |
| 2001/0005591 A1 | 6/2001 | Qasba et al. |
| 2001/0038836 A1 | 11/2001 | During et al. |
| 2002/0102239 A1 | 8/2002 | Koopmans |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton et al. |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0045552 A1 | 3/2003 | Robarge et al. |
| 2003/0068306 A1 | 4/2003 | Dilbert |
| 2003/0096841 A1 | 5/2003 | Robarge et al. |

(56) References Cited

U.S. PATENT DOCUMENTS

| | | |
|---|---|---|
| 2003/0161818 A1 | 8/2003 | Weiss et al. |
| 2003/0180269 A1 | 9/2003 | Hariri |
| 2003/0187515 A1 | 10/2003 | Hariri |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0084815 A1 | 4/2006 | Muller et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0224174 A1 | 9/2007 | Kang et al. |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2009/0004150 A1 | 1/2009 | Schwartz-Albiez et al. |
| 2009/0017539 A1 | 1/2009 | Spanholtz |
| 2009/0053805 A1 | 2/2009 | Hariri |
| 2009/0104164 A1 | 4/2009 | Zhang et al. |
| 2009/0123442 A1 | 5/2009 | Dilber et al. |
| 2009/0126482 A1 | 5/2009 | Fundak et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2009/0263361 A1 | 10/2009 | Lee et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0178275 A1 | 7/2010 | Spanholtz |
| 2010/0183571 A1 | 7/2010 | Paludan et al. |
| 2010/0216181 A1 | 8/2010 | Daigh et al. |
| 2010/0260847 A1 | 10/2010 | Hariri |
| 2010/0285586 A1 | 11/2010 | Timmins et al. |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |

(56) References Cited

U.S. PATENT DOCUMENTS

| | | | |
|---|---|---|---|
| 2012/0122215 A1 | 5/2012 | Edinger et al. |
| 2012/0156782 A1 | 6/2012 | Tryggvason et al. |
| 2012/0171160 A1 | 7/2012 | Johnson, Jr. et al. |
| 2012/0171161 A1 | 7/2012 | Abramson et al. |
| 2012/0171295 A1 | 7/2012 | Abramson et al. |
| 2012/0230959 A1 | 9/2012 | Abbot et al. |
| 2012/0328583 A1 | 12/2012 | Herzberg et al. |
| 2013/0022581 A1 | 1/2013 | Edinger et al. |
| 2013/0028871 A1 | 1/2013 | Edinger et al. |
| 2013/0071362 A1 | 3/2013 | Bhatia et al. |
| 2013/0184821 A1 | 7/2013 | Hariri et al. |
| 2013/0259845 A1 | 10/2013 | Heidaran et al. |
| 2013/0315875 A1 | 11/2013 | Hariri et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 A1 | 3/2003 |
| EP | 1384775 A1 | 1/2004 |
| EP | 1405649 | 4/2004 |
| EP | 1535994 | 6/2005 |
| EP | 1775341 | 4/2007 |
| EP | 2411507 A1 | 2/2012 |
| JP | 2003235549 | 12/2002 |
| JP | 2005151907 | 11/2003 |
| JP | 2004-523220 | 8/2004 |
| JP | 2004-528021 | 9/2004 |
| JP | 2006-509770 | 3/2006 |
| WO | WO 90/11354 | 10/1990 |
| WO | WO 91/01140 | 2/1991 |
| WO | WO 91/06666 | 5/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 97/18298 | 5/1997 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 02/46373 | 6/2002 |
| WO | WO 02/063962 | 8/2002 |
| WO | WO 02/064755 | 8/2002 |
| WO | WO 03/042405 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/095584 | 10/2005 |
| WO | WO 2005/097190 | 10/2005 |
| WO | WO 2005/105992 | 11/2005 |
| WO | WO 2005/055929 | 1/2006 |
| WO | WO 2006/015214 | 2/2006 |
| WO | WO 2006/090286 | 8/2006 |
| WO | WO 2006/111706 | 10/2006 |
| WO | WO 2007/011693 | 1/2007 |
| WO | WO 2007/024441 | 3/2007 |
| WO | WO 2007/037682 | 4/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/076522 | 7/2007 |
| WO | WO 2007/079183 | 7/2007 |
| WO | WO 2007/087293 | 8/2007 |
| WO | WO 2008/019148 | 2/2008 |
| WO | WO 2008/051568 | 5/2008 |
| WO | WO 2008/060541 | 5/2008 |
| WO | WO 2008/100497 | 8/2008 |
| WO | WO 2008/118020 | 10/2008 |
| WO | WO 2009/045360 | 4/2009 |
| WO | WO 2010/013947 | 2/2010 |
| WO | WO 2010/027094 | 3/2010 |
| WO | WO 2010/110734 | 9/2010 |
| WO | WO 2010/111631 | 9/2010 |
| WO | WO 2012/009422 | 1/2012 |
| WO | WO 2012/075412 | 6/2012 |

OTHER PUBLICATIONS

Alici et al., "Anti-myeloma activity of endogenous and adoptively transferred activated natural killer cells in experimental multiple myeloma model," Exp Hematol. 35(12):1839-46 (2007).

Allikmets et al., "A human placenta specific ATP binding cassette gene (*ABCP*) on chromosome 4q22 that is involved in multidrug resistance," Cancer Res. 58(23):5337-5339 (1998).

Anker In't P, et al., "Isolation of Mesenchymal Stem Cells of Fetal or Maternal Origin from Human Placenta," Stem Cells; 22:1338-45 (2004).

Aplin, "Implantation, trophoblast Differentiation and Haemochorial Placentation: Mechanistic Evidence in vivo and in vitro," Journal of Cell Science 99:681-692 (1991).

Ashihara, et al., "Successful Peripheral Blood Stem Cell Transplantation for Myelodysplastic Syndrome," Bone Marrow Transplantation 24(12): 1343-1345 (1999).

Bailo, et al., "Engraftment Potential of Human Amnion and Chorion Cells Derived from Term Placenta," Transplantation 78:1439-1448 (2004).

Ballin, et al., "Autologous Umbilical Cord Blood Transfusion," Arch. Dis. Child Fetal Neonatal. Ed. 73(3):F181-F183 (1995).

Barkholt et al., "Resetting the immune system in refractory Crohn's disease: is autologous hematopoietic stem cell transplantation the way forward?" Immunotherapy. Sep. 2009;1(5):753-64.

Barlow et al., "Comparison of Human Placenta- and Bone Marrow-Derived Multipotent Mesenchymal Stem Cells," Stem Cells and Development 17:1095-1108 (2008).

Barry et al., "The Monoclonal Antibody SH-2, Raised Against Human Mesenchymal Stem Cells, Recognizes an Epitope on Endoglin (CD105)," Osiris Therapeutics Inc., (2001) Aliceanna Street, Baltimore, MD 21231, Biochemical and Biophysical Research Communications 265:134-139 (1999).

Barry, "Where do all the placentas go?" Canadian Journal of Infection Control 9(1):8-10 (1994).

Battula et al., "Prospective Isolation and Characterization of Mesenchymal Stem Cells from Human Placenta Using a Firzzled-9-Specific Monoclonal Antibody," Differentiation 76:326-336 (2008).

Belvedere, et al., "Increased Blood Volume and CD34(+)CD38(−) Progenitor Cell Recovery Using a Novel Umbilical Cord Blood Collection System," Stem Cells 18(4):245-251 (2000).

Bloxam et al., "Culture of Syncytiotrophoblast for the Study of Human Placental Transfer. Part I: Isolation and Purification of Cytotrophoblast," Placenta 18:93-98 (1997).

Bloxam, "Human Placental Trophoblast Culture: One-Sided and Two-Sided Models," Proceedings of the Nutrition Society 50:349-354 (1991).

Bossolasco et al., "Molecular and phenotypic characterization of human amniotic fluid cells and their differentiation potential," Cell Research 16:329-336 (2006).

Bullen et al., "Two-Sided Culture of Human Placental Trophoblast. Morphology, Immunocytochemistry and Permeability Properties," Placenta 11:431-450 (1990).

(56) References Cited

OTHER PUBLICATIONS

Campagnoli, et al., "Identification of Mesenchymal Stem/Progenitor Cells in Human First-Trimester Fetal Blood, Liver, and Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Carayol et al., "NK Cells Differentiated from Bone Marrow, Cord Blood and Peripheral Blood Stem Cells Exhibit Similar Phenotype and Functions," European Journal of Immunology 28(6):1991-2002 (1998).
Carlens et al., "A new method for in vitro expansion of cytotoxic human CD3-CD56+ natural killer cells," Hum Immunol. 62(10):1092-8 (2001).
Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).
Cester et al., "Cation Transport Across Cultured Trophoblast Membrane in Preeclampsia," Clin. and Exper. Hyper. in Pregnancy, B11(1):59-69 (1992).
Chang, et al., "Placenta-Derived Multipotent Cells Exhibit Immunosuppressive Properties That are Enhanced in the Presence of Interferon-gamma," Stem Cells 24:2466-2477 (2006).
Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chies et al., "Sickle Cell Disease: A Chronic Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Contractor, et al., "A comparison of the effects of different perfusion regimens on the structure of the isolated human placental lobule," Cell Tissue Res. 237:609-617 (1984).
Cosma, et al., "Use and Application of Stem Cells in Toxicology," SOT Annual Meeting, p. 4, Abstract 19 (2003).
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Czarneski, et al., "Effects of Cord Blood Transfer on the Hematopoietic Recovery Following Sublethal Irradiation in MRL lpr/lpr Mice," Proc. Soc. Exp. Biol. Med. 220(2):79-87 (1999).
Database WPI Week 200357 Derwent Publications Ltd., London, GB, AN 2003-59905 & CN 1 407 888 A (Zhou S) Apr. 2, 2003.
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood; 96(13): 4096-4102 (2000).
Davila, et al., "Use and Application of Stem Cells in Toxicology," Toxicological Sciences 79:214-223 (2004).
De Coppi, , et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81 (2004).
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93 (2002).
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7 (2005).
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Dezell et al., Natural killer cell differentiation from hematopoietic stem cells: a comparative analysis of heparin- and stromal cell-supported methods. Biol Blood Marrow Transplant. 18(4):536-45. Epub Dec. 7, 2011 (2012).
Dominici, et al., "Minimal Criteria for Defining Multipotent Mesenchymal Stromal Cells. The International Society for Cellular Therapy Position Statement," Cytotherapy 8(4):315-317 (2006).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).
Dushnik-Levinson, et al. "Embryogenesis in vitro: study of differentiation of embryonic stem cells." Biol Neonate. 67(2):77-83 (1995).
Eissens et al., Defining early human NK cell developmental stages in primary and secondary lymphoid tissues. PLoS One. 2012;7(2):e30930.Epub Feb. 3, 2012.
Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Ende, et al., "Human Umbilical Cord Blood Cells Amerliorate Alzheimer's Disease in Transgenic Mice," J. Med. 32(3-4):241-7 (2001).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2001).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Esser et al., NK cells engineered to express a GD2 -specific antigen receptor display built-in ADCC-like activity against tumour cells of neuroectodermal origin. J Cell Mol Med. 16(3):569-81 (2012).
Evans, "Stem Cell Therapy: Moving towards Reality," Am. J. Obstet. Gynecol. 194:662-663 (2006).
Fasouliotis, et al., "Human umbilical cord blood banking and transplantation: a state of the art," Eur. J. Obstet. Gynecol. Reprod. Biol. 90(1):13-25 (2000).

(56) References Cited

OTHER PUBLICATIONS

Fauriat et al., "Deficient expression of NCR in NK cells from acute myeloid leukemia: evolution during leukemia treatment and impact of leukemia cells in NCRdull phenotype induction," Blood 109: 323-330 (2007).
Ferlazzo et al, PNAS USA 101(47):16606-11 (2004).
Fisher et al., "Adhesive and Degradatie Properties of Human Placental Cytotrophoblast Cells In Vitro," Journal od Cell Biology 109:891-902 (1989).
Frank H G, et al., "Cell culture models of human trophoblast: primary culture of trophoblast—a workshop report." Placent APR 2001, vol. 22 Suppl A, Apr. 2001, pp. S107-S109, XP002443188 ISSN: 0143-4004 (2001).
Freud et al., "Evidence for Discrete Stages of Human Natural Killer Cell Differentiation In Vivo," Journal of Eperimental Medicine 203(4):1033-1043(2006).
Garcia-Olmo et al., "Autologous Stem Cell Transplantation for Treatment of Rectovaginal Fistula in Perianal Crohn's Disease: A New Cell-based Therapy", Int. J. Colorectal Dis. 18:451-454 (2003).
Genbacev et al., "Regulation of Human Placental Development by Oxygen Tension," 277(5332):1669-1672 (1997).
Gluckman, et al., "Cord Blood Heamatopoietic Stem Cells: Biology and Transplantation," In: Hematology, American Society of Hematology Education Program Book p. 1-14 (1998).
Gluckman, et al., "Results of Unrelated Umbilical Cord Blood Hematipoeietic Stem Cell Transplant," Transfusion Cinique et Biologique 8(3):146-154 (2001).
Greenwood et al., "Membrane Potential Difference and Intracellular Cation Concentrations in Human Placental Trophoblast Cells in Culture," Journal of Physiology 492.3:629-640 (1996).
Guimaraes et al., "Evaluation of ex vivo expanded human NK cells on antileukemia activity in SCID-beige mice," Leukemia. 20(5):833-9 (2006).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Herrera, et al., "Mesenchymal Stem Cells Contribute to the Renal Repair of Acute Tubular Epithelial Injury,"• Int. J. Mol. Med.: 14(6):1035-41 (2004).
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirano et al., "CD9 is Expressied in Extravillous Trophoblasts in Association with Integrin α3 and integrin α5," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075 (2000).
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells,"• Biochemical and Biophysical Research Communications; 362:347-53 (2007).
Huss, "Isolation of Primary and Immortalized CD34— Hematopoietic and Mesenchymal Stem Cells from Various Sources," Stem Cells 18:1-9 (2000).
Huss, "Perspectives on the Morphology and Biology of CD34-Negative Stem Cells," J. Hematother. Stem. Cell Res. 9(6):783-793 (2000).
Igura, et al., "Isolation and Characterization of Mesencymal Progenitor Cells from Chorionic Villi of Human Placenta," Cytotherapy 6(6): 543-553 (2004).
Imai et al., Genetic modification of T cells for cancer therapy. J Biol Regul Homeost Agents. Jan.-Mar.;18(1):62-71 (2004).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
International Preliminary Report on Patentability from PCT/US2006/049491 dated Jan. 14, 2008.
International Search Report and Written Opinion from PCT/US2006/049491 dated Sep. 26, 2007.
Iwasaki, "Recent Advances in the Treatment of Graft-Versus-Host Disease,"• Clin. Med. Res.; 2(4):243-52 (2004).
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in The Human Placenta," Trophoblast Research 10:21-65 (1997).
Kawata, et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Kliman et al., "Purification, Characterization, and In Vitro Differentiation of Cytotropholblasts from Human Term Placentae," Endocrinology 118(4):1567-1582 (1986).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81 (2004).
Korbling, et al., "Hepatocytes and Epithelial Cells of Donor Origin in Recipients of Peripheral-Blood Stem Cells," N. Engl. J. Med. 346(10):738-746 (2002).

(56) References Cited

OTHER PUBLICATIONS

Kurtzberg, "Placental Bood as a Surce of Hmatopoietic Sem Cells for Transplantation into Unrelated Recipients," N. Engl. J. Med. 335:157-166 (1996).
Landon et al., "The Effects of Ethanol Methotrexate and Diphenylhydantoin on [$^{14}$C] Leucine Incorporation by Human Trophoblasst Cells Cultured In Vitro," British Journal of Obstetrics and Gynaecology 94:252-255 (1987).
Law, E., et al., "Enhanced ex vivo expansion of cord blood CD34+ cells by novel immunomodulatory agents (IMiD)," Stem Cell Symposium, State of New Jersey Commission on Science & Technology (Abstract) (2005).
Lazarus, et al., "Cotransplantation of HLA-Identical Sibling Culture-Expanded Mesenchymal Stem Cells and Hematopoietic Stem Cells in Hematologic Malignancy Patients, Biol Blood Marrow Transplant," 11(5):389-398 (2005).
Le Blanc, et al., "Treatment of Severe Acute Graft-Versus-Host Disease With Third Party Haploidentical Mesenchvmal Stem Cells,"• Lancet; 363(9419):1439-41 (2004).
Lebkowski, et al., "Serum and Plasma Levels of FGF-2 and VEGF in Healthy Blood Donors," Cancer J. 7(Suppl 2):S83-S93 (2001).
Lee-Macary et al, J Immunol Methods 252(1-2):83-92 (2001).
Lehmann et al., Ex Vivo Generated Natural Killer Cells Acquire Typical Natural Killer Receptors and Display a Cytotoxic Gene Expression Profile Similar to Peripheral Blood Natural Killer Cells. Stem Cells Dev. 21(16):2926-2938 (2012).
Leonard, et al., "The Role of ABC Transporters in Clinical Practice," Oncologist. 8:411-424 (2003).
Li, et al., "Mesenchymal Stem Cells Derived from Human Placenta Suppress Allogenic Umbilical Cord Blood Lymphocyte Proliferation." Cell Res. 15: 539-547 (2005).
Lin, et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626 (2005).
Lipinski et al., "Human Trophoblast Cell-Surface Antigen Defined by Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Luedke et al., Cetuximab therapy in head and neck cancer: Immune modulation with interleukin-12 and other natural killer cell-activating cytokines. Surgery. Jul. 6, 2012.
Ma, et al., "Development of an in vitro Human Placenta Model by the Cultivation of Human Trophoblasts in a Fiber-Based Bioreactor System," Tissue Engineering 5, 91-102 (1999).
Ma, et al., "Human Umbilical Cord Wharton's Jelly-Derived Mesenchymal Stem Cells Differentiation into Nerve-Like Cells," Chinese Med. Jour., 118(23):1987-93 (2005).
Mackay, et al., "Chondrogenic Differentiation of Cultured Human Mesenchymal Stem Cells from Marrow," Tissue Engineering; 4(4):415-28 (1998).
Malmberg et al., "NK cell-mediated targeting of human cancer and possibilities for new means of immunotherapy," Cancer Immunol Immunother. 57(10):1541-52 (2008).
McMaster et al, "Human Placental HLA-G Expression is Restricted to Differentiated Cytotrophoblasts," J. Immunol 154(8):3771-3778 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki, et al., "Isolation of Multipotent Stem Cells from Placenta." AASLD Abstracts, Hepatology, Oct. 2003, Abstract 279, p. 290A (2003).
Miki, et al., "Production of Hepatocytes from Human Amniotic Stem Cells." Hepatology, Abstract 20, vol. 36, No. 4, Pt. 2 (2002).
Miki, et al., "Stem Cell Characteristics of Amniotic Epithelial Cells." Stem Cells Express, published online Aug. 9, 2005; doi:10. 1634/stemcells.2004-0357 (2005).
Miller et al., "Successful adoptive transfer and in vivo expansion of human haploidentical NK cells in patients with cancer," Blood 105:3051-3057 (2005).
Minguell, et al., "Mesenchymal Stem Cells," Exp. Biol. Med. 226:507-520 (2001).
Moore, et al., "A Simple Perfusion Technique for Isolation of Maternal Intervillous Blood Mononuclear Cells from Human Placentae," J. Immunol Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Morgan et al., "Human Placental Cell Culture," Biochemical Society Transactions 12: 317-318 (1984).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol.; 15(7):1794-1804 (2004).
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood; 99(11):4200-06 (2002).
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 16:367-373 (1995).
Müller et al., Expression of a CD20-specific chimeric antigen receptor enhances cytotoxic activity of NK cells and overcomes NK-resistance of lymphoma and leukemia cells. Cancer Immunol Immunother. 57(3):411-23 (2008).
Myllynen "In Search of Models for Hepatic and Placental Pharmacokinetics," [Dissertation] University of Oulu, (2003).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int.; 70(1):121-29 (2006).
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. to corresponding claims filed in Peru; English translation Jan. 18, 2008.
Oda et al., "Trophoblast Stem Cells," Methods in Enxymology 419(15):387-400 (2006).
Paludan, et al , "Immune Suppression by Placenta Derived Adherent Cells (PDAC) Correlate with Monocyte Chemoattractant Protein-1 and 1L-2 Secretion," Blood 108 (abstract only) 48B (2006).
Paludan, et al., "Placental Derived Stem Cells (PDAC) Suppress the Allo-MLR and the EBV Regression Assay," http://www.call4abstract.com/hem/finalpreview.php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchvmal Stem Cells," Stem Cells; 22(7):1263-78 (2004).

(56) References Cited

OTHER PUBLICATIONS

Papaioannou, et al., "Stem Cells from Early Mammalian Embryos" Stem Cells Handbook:19-31 (2004).
Pegram et al., Adoptive transfer of gene-modified primary NK cells can specifically inhibit tumor progression in vivo. J Immunol. 181(5):3449-55 (2008).
Pellegrini, et al., "FADD and Caspase-8 Are Required for Cytokine-Induced Proliferation of Hemopoietic Progenitor Cells," Blood 106(5):1581-1589 (2005).
Pende et al., "Analysis of the receptor-ligand interaction in the natural killer-mediated lysis of freshly isolated myeloid or lymphoblastic leukemias: evidence for the involvement of the poliovirus receptor (CD155) and Nectin-2 (CD112)," Blood 105: 2066-2073 (2004).
Pera, et al., "Human Embryonic Stem Cells," J. Cell. Sci. 113:5-10 (2000).
Petroff et al., "Isolation and Culture of Term Human Trophoblast Cells," Methods in Molecular Medicine, Placenta and Trophoblast, 1(16):203-217 (2006).
Pinho et al., "Ex vivo differentiation of natural killer cells from human umbilical cord blood CD34+ progenitor cells," Cell Commun Adhes 18(3):45-55. Epub Sep. 12, 2011.
Pinho et al., "Genetic regulation of ex vivo differentiated natural killer cells from human umbilical cord blood CD34+ cells," J Recept Signal Transduct Res. Jul. 4, 2014 published online.
Pittenger., et al. "Multilineage Potential of Adult Human Mesenchymal Stem Cells." Science 284(5411):143-147 (1999).
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133-A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured; 38(Supp. 4):523-33 (2007).
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Ringler et al., "In Vitro Systems for the Study of Human Placental Endocrine Function," Endocrine Reviews 11(1):105-123 (1990).
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Roussev et al., "Phenotypic Characterization of Normal Human Placental Mononuclear Cells", Journal of Reproductive Immunology, Elsevier Science Ireland Ltd., IE, vol. 25, No. 1, pp. 15-29 (Sep. 1993).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Rubnitz et al, 2010, NKAML: A Pilot Study to Determine the Safety and Feasibility of Haploidentical Natural Killer Cell Transplantation in Childhood Acute Myeloid Leukemia, J. Clin Oncol 28, published ahead of print on Jan. 19, 2010 as 10.1200/JCO.2009.24.4590.
Ruggeri et al., "Effectiveness of donor natural killer cell alloreactivity in mismatched hematopoietic transplants," Science 295:2097-2100 (2002).
Russo, "Fighting Darwin's Battles. Symposium Marks Evolutionist Victory, Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Sapin, "Esterification of Vitamin A by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(Suppl A): S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
ScienCell—Human Amniotic Epithelial Cells. http://www.sciencellonline.com/products/7100.htm.
Shamblott, et al., "Derivation of Pluripotent Stem Cells from Cultured Human Primordial Germ Cells," Proc. Natl. Acad. Sci. USA 95(23):13726-13731 (1998).
Sherley, "Asymmetric Cell Kinetics Genes: The Key to Expansion of Adult Stem Cells in Culture", Stem Cell 20:561-72 (2002).
Shook et al., Natural killer cell engineering for cellular therapy of cancer. Tissue Antigens. Dec;78(6):409-15 (2011).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Southard et al., "Important contents of the UW solution," Transplantation 49(2):251-257 (1990).
Spanholtz et al., High log-scale expansion of functional human natural killer cells from umbilical cord blood CD34-positive cells for adoptive cancer immunotherapy. PLoS One Feb. 15;5(2):e9221 (2010).
Spanholtz et al., Clinical-grade generation of active NK cells from cord blood hematopoietic progenitor cells for immunotherapy using a closed-system culture process. PLoS One 6(6):e20740. Epub Jun. 16, 2011.
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," In Vitro 14(7):6331-638 (1978).
Sunderland et al., "HLA A, B, C Antigens Are Expressed on Nonvillous Trophoblast of the Early Human Placenta," Journal of Immunology 127(6):2614-2615 (1981).
Tabiasco, et al., "Human decidual NK cells: Unique phenotype and functional properties—a review," Placenta, W.B. Saunders, 27:34-39 (2006).

(56) References Cited

OTHER PUBLICATIONS

Takahashi et al., "Induction fo CD16(+) CD56(bright) NK cells with antitumour cytotoxicity not only from CD16(-) CD56(bright) NK cells but also from CD16(+) CD56(dim) NK cells", Scandinavian Journal of Immunology, pp. 126-138, XP002528954 (2007).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-7 (1998).
Toma, et al., "Human Mesenchymal Stem Cells Differentiate to a Cardiomyocyte Phenotype in the Adult Murine Heart," Circulation; 105:93-98 (2002).
Triulzi et al., Antibody-dependent natural killer cell-mediated cytotoxicity engendered by a kinase-inactive human HER2 adenovirus-based vaccination mediates resistance to breast tumors. Cancer Res. Oct. 1;70(19):7431-41 (2010).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering; 100(1):12-27 (2005).
Verneris et al., 2010, Natural Killer Cell Consolidation for Acute Myelogeous Leukemia: A Cel Therapy Ready for Prime Time?, J Clin Oncol, vol. 28, No. 210, published ahead of print on Jan. 19, 2010 as 10.1200/JCO.2009.26.4002.
Viacord, Umblicical cord blood can save lives (Informational brochure), Boston: ViaCell CENTR-BRO R1 Oct. 2001.
Wang, et al., "Enhanced Recovery of Hematopoietic Progenitor and Stem Cells from Cultivated, Postpartum Human Placenta," Blood 98(11/1):183a Abstract No. 769 (2001).
Wang, et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe, et al, "Multilineage Potential of Human Placenta-Derived Mesenchymal Cells," Blood 100(11):517a, Abstract 2022 (2002).
Weiss et al., "Human Umbilical Cord Matrix Stem Cells: Preliminary Characterization and Effect of Transplantation in a Rodent Model of Parkinson's Disease", 24, 781-792 (2006).
Weissman et al., "Stem and Progenitor Cells: Origins, Phenotypes, Lineage Commitments, and Transdifferentiations", Annu. Rev. Cell Dev. Biol. 17:387-403 (2001).
Wiesmann, et al., "Effects of Caspase Inhibitors on Hematopoietic Engraftment After Short-Term Culture," Cell. Transplant. 11(4):351-358 (2002).
Woods, et al., "Osomometric and permeability characteristics of human placental/umbilical cord blood CD34+ cells and their application to cryopreservation," J. Hematother. Stem Cell Res. 9(2):161-173 (2000).
Wulf et al., "Mesengenic Progenitor Cells Derived from Human Placenta," Tissue Engineering 10(7/8): 1136-1147 (2004).
Xu et al., "BMP4 Initiates Human Embryonic Stem Cell Differentiation to Trophoblast," Nature Biology 20:1261-1264 (2002).
Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).
Ye, et al., "Recovery of Placental-Derived Adherent Cells with Mesenchymal Stem Cell Characteristics," Blood 98(11/1):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen, B. Linju et al, "Isolation of multipotent cells from human term placenta" Stem Cells (Dayton, Ohio) vol. 23, No. 1, Jan. 2005, pp. 3-9, XP002443187 ISSN: 1065-5099 (2005).
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Yu et al., "FLT3 Ligand Promotes the Generation of a Distinct CD34+ Human Natural Killer Cell Progenitor That Responds to Interleukin-15," Blood 92(10):3647-3657 (1998).
Yui et al., "Functional, Long-term Cultures of Human Term Trophoblasts Purified by Column-elimination of CD9 Expressing Cells," Placenta 15:231-246 (1994).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol , 47(1):109-16 (2003).
Zhang, et al., "Human Placenta-Derived Mesenchymal Progenitor Cells Support Culture Expansion of Long-Term Culture-Initiating Cells from Cord Blood CD34+ Cells." Exp. Hematol. 32: 657-664 (2004).
Roussev et al., 1993, "Phenotypic characterization of normal human placental mononuclear cells," J Reproductive Immunol, 25:15-29.
Keskin et al., 2007, "TGFβ promotes conversion of $CD16^+$ peripheral blood NK cells into $CD16^-$ NK cells with similarities to decidual NK cells," Proc Natl Acad Sci USA, 104(9):3378-3383.
Möller et al., 1998, "A distinct distribution of natural killer cell subgroups in human tissues and blood," Int J Cancer, 78:533-538.
Takahashi et al., 2007, "Induction of $CD16^+ CD56^{bright}$ NK cells with antitumour cytotoxicity not only from $CD16^- CD56^{bright}$ NK cells but also from $CD16^- CD56^{dim}$ NK cells," Scand J Immunol, 65:126-138.
Sudo et al., 2003, Japanese Journal of Cancer and Chemotherapy, 30(11):1817-1820.
Okoshi and Shibuya, Hematology & Oncology, 2005, vol. 51, No. 2, p. 225-230. [With English Translation of Relevant Part, as circled.].
Van Den Brink et al., 1990, "The generation of natural killer (NK) cells from NK precursor cells in rat long-term bone marrow cultures", J Exp Med; 172:303-313.
Mrozek et al., 1996, "Role of interleukin-15 in the development of human CD56+ natural killer cells from CD34+ hematopoietic progenitor cells", 87(7):2632-2640.
Kabilova and Chernolovskaya, 2006, "Inhibition of Cancer Cells Proliferation by Double Stranded RNA Targeted to mRNA of MYC Oncogenes," Newsletter of VOGiS 10(2): 373-381 (with English Abstract).

* cited by examiner

A

B

TUMOR SUPPRESSION USING HUMAN PLACENTAL PERFUSATE AND HUMAN PLACENTA-DERIVED INTERMEDIATE NATURAL KILLER CELLS

This application is a continuation application of U.S. application Ser. No. 12/240,956, filed Sep. 29, 2008, which claims benefit of U.S. Provisional Patent Application No. 60/995,763, filed Sep. 28, 2007, and U.S. Provisional Patent Application No. 61/090,555, filed Aug. 20, 2008, the disclosures of which are hereby incorporated by reference in their entireties.

1. FIELD

Presented herein are methods of suppressing the growth or proliferation of tumor cells by contacting the tumor cells with placental perfusate, placental perfusate-derived cells, natural killer cells from placenta, e.g., from placental perfusate, and/or combined natural killer cells comprising natural killer cells from placenta, e.g., from placental perfusate and natural killer cells from umbilical cord blood. Also provided herein are methods of producing a unique population of natural killer cells from placenta, e.g., from placental perfusate, e.g., human placental perfusate. Further provided herein are methods of using the placental perfusate, and the natural killer cells therefrom, to suppress the proliferation of tumor cells.

2. BACKGROUND

Placental perfusate comprises a collection of placental cells obtained by passage of a perfusion solution through the placental vasculature, and collection of the perfusion fluid from the vasculature, from the maternal surface of the placenta, or both. Methods of perfusing mammalian placentas are described, e.g., in U.S. Pat. No. 7,045,146 and U.S. Pat. No. 7,255,879. The population of placental cells obtained by perfusion is heterogenous, comprising hematopoietic ($CD34^+$) cells, nucleated cells such as granulocytes, monocytes and macrophages, a small percentage (less than 1%) tissue culture substrate-adherent placental stem cells, and natural killer cells. No one to date has described the use of placental perfusate, or populations of placental cells from perfusate, in the suppression of tumor cell proliferation.

Natural killer (NK) cells are cytotoxic lymphocytes that constitute a major component of the innate immune system. NK cells do not express T-cell antigen receptors (TCR), CD3 or surface immunoglobulins (Ig) B cell receptor, but usually express the surface markers CD16 (FcγRIII) and CD56 in humans. NK cells are cytotoxic; small granules in their cytoplasm contain special proteins such as perforin and proteases known as granzymes. Upon release in close proximity to a cell slated for killing, perforin forms pores in the cell membrane of the target cell through which the granzymes and associated molecules can enter, inducing apoptosis. One granzyme, granzyme B (also known as granzyme 2 and cytotoxic T-lymphocyte-associated serine esterase 1), is a serine protease crucial for rapid induction of target cell apoptosis in the cell-mediated immune response.

NK cells are activated in response to interferons or macrophage-derived cytokines. Activated NK cells are referred to as lymphokine activated killer (LAK) cells. NK cells possess two types of surface receptors, labeled "activating receptors" and "inhibitory receptors," that control the cells' cytotoxic activity.

Among other activities, NK cells play a role in the host rejection of tumors. Because cancer cells have reduced or no class I MHC expression, they can become targets of NK cells. Accumulating clinical data suggest that haploidentical transplantation of human NK cells isolated from PBMC or bone marrow mediate potent anti-leukemia effects without possessing detectable graft versus host disease (GVHD). See Ruggeri et al., *Science* 295:2097-2100 (2002)). Natural killer cells can become activated by cells lacking, or displaying reduced levels of, major histocompatibility complex (MHC) proteins. Activated and expanded NK cells and LAK cells have been used in both ex vivo therapy and in vivo treatment of patients having advanced cancer, with some success against bone marrow related diseases, such as leukemia; breast cancer; and certain types of lymphoma. LAK cell treatment requires that the patient first receive IL-2, followed by leukopheresis and then an ex vivo incubation and culture of the harvested autologous blood cells in the presence of IL-2 for a few days. The LAK cells must be reinfused along with relatively high doses of IL-2 to complete the therapy. This purging treatment is expensive and can cause serious side effects. These include fluid retention, pulmonary edema, drop in blood pressure, and high fever.

In spite of the advantageous properties of NK cells in killing tumor cells and virus-infected cells, they remain difficult to work with and to apply in immunotherapy, primarily due to the difficulty in maintaining their tumor-targeting and tumoricidal capabilities during culture and expansion. Thus, there is a need in the art for a ready supply of natural killer cells.

3. SUMMARY

Provided herein is the use of placental perfusate; cells from placental perfusate, e.g., total nucleated cells from placental perfusate; combinations of placental perfusate cells and cord blood cells; and/or natural killer cells from placenta, e.g., natural killer cells from placental perfusate or natural killer cells obtained by digestion of placental tissue, to suppress tumor cell proliferation.

In one aspect, provided herein is a method of suppressing the proliferation of a tumor cell, or population of tumor cells, comprising contacting the tumor cell or population of tumor cells with human placental perfusate. In a specific embodiment of this method, the tumor cell is a blood cancer cell. In another specific embodiment, the tumor cells are blood cancer cells. In another specific embodiment, the tumor cell is a solid tumor cell. In another specific embodiment, the tumor cells are solid tumor cells. In another embodiment, the tumor cell is a primary ductal carcinoma cell, a leukemia cell, an acute T cell leukemia cell, a chronic myeloid lymphoma (CML) cell, an acute myelogenous leukemia cell, a chronic myelogenous leukemia (CML) cell, a lung carcinoma cell, a colon adenocarcinoma cell, a histiocytic lymphoma cell, multiple myeloma cell, a retinoblastoma cell, a colorectal carcinoma cell, or a colorectal adenocarcinoma cell. In another specific embodiment, said contacting takes place in vitro. In another specific embodiment, said contacting takes place in vivo. In a more specific embodiment, said in vivo contacting takes place in a human.

In another specific embodiment, said placental perfusate is perfusate that has been passed through placental vasculature, e.g., only through placental vasculature. In another specific embodiment, said placental perfusate has been passed through the placental vasculature and collected from the maternal face of the placenta. In another specific embodiment, all, or substantially all (e.g., greater than 90%, 95%, 98% or 99%) of cells in said placental perfusate are fetal cells. In another specific embodiment, the placental perfusate comprises fetal and maternal cells. In a more specific embodiment, the fetal cells in said placental perfusate comprise less than about 90%, 80%, 70%, 60% or 50% of the cells in said perfusate. In another specific embodiment, said perfusate is obtained by passage of a 0.9% NaCl solution through the placental vasculature. In another specific embodiment, said perfusate comprises a culture medium. In another specific embodiment, said perfusate has been treated to remove a plurality of erythrocytes.

In another aspect, provided herein is a method of suppressing the proliferation of a tumor cell or plurality of tumor cells comprising contacting the tumor cell or plurality of tumor cells with a plurality of placental perfusate cells. In another specific embodiment, said plurality of placental perfusate cells are, or comprise, total nucleated cells from placental perfusate. In another specific embodiment, said placental perfusate or placental perfusate cells, e.g., total nucleated cells from placental perfusate, have been treated to remove at least one type of cell. In another specific embodiment, said contacting takes place in vitro. In another specific embodiment, said contacting takes place in vivo. In a more specific embodiment, said in vivo contacting takes place in a mammal, e.g., a human. In another specific embodiment, said placental perfusate cells have been treated to enrich for at least one type of cell, e.g., $CD56^+$ cells. In another specific embodiment, said placental perfusate cells are $CD56^+$ placental cells. In a more specific embodiment, the $CD56^+$ cells are $CD56^+CD16^-$ natural killer cells, e.g., placental intermediate natural killer (PINK) cells, e.g., obtained from placental perfusate cells or placental cells obtained by mechanical or enzymatic disruption of placental tissue. In another specific embodiment, said $CD56^+$ cells are selected by CD56-conjugated microbeads. In another specific embodiment, said $CD56^+$ cells comprise cells that exhibit detectably lower expression of NKG2D, NKp46 or CD94 than an equivalent number of $CD56^+CD16^+$ natural killer cells. In another specific embodiment, the PINK cells are $CD3^-$. In a more specific embodiment, at least 50% of the cells in said placental perfusate cells are said $CD56^+$ cells. In a more specific embodiment, wherein the $CD56^+$ cells are at least 50% of said placental perfusate cells, the tumor cell is a primary ductal carcinoma cell, a leukemia cell, an acute T cell leukemia cell, a chronic myeloid lymphoma (CML) cell, an acute myelogenous leukemia cell, a chronic myelogenous leukemia (CML) cell, a lung carcinoma cell, a colon adenocarcinoma cell, a histiocytic lymphoma cell, multiple myeloma cell, a retinoblastoma cell, a colorectal carcinoma cell or a colorectal adenocarcinoma cell. In specific embodiments, said contacting is contacting in vitro. In another embodiment, said contacting is contacting in vivo, e.g., in a mammal, e.g., a human.

In another aspect, provided herein is a method of suppressing the proliferation of a tumor cell or plurality of tumor cells comprising contacting the tumor cell or plurality of tumor cells with a plurality of natural killer cells from placenta, e.g., PINK cells. In a specific embodiment, the natural killer cells from placenta are natural killer cells obtained from placental perfusate. In another specific embodiment, the natural killer cells are natural killer cells obtained by physical disruption and/or enzymatic digestion of placental tissue. In another specific embodiment, the natural killer cells are $CD56^+$ $CD16^-$ natural killer cells, e.g., PINK cells. In another specific embodiment, said natural killer cells are selected, e.g., from placental perfusate cells or cells obtained by physical disruption and/or enzymatic digestion of placental tissue, by CD56-conjugated microbeads. In another specific embodiment, the natural killer cells are $CD3^-$. In a specific embodiment, the plurality of natural killer cells is at least 80% of the cells in a population of cells that comprises the natural killer cells. In another specific embodiment, said contacting takes place in vitro. In another specific embodiment, said contacting takes place in vivo. In a more specific embodiment, said in vivo contacting takes place in a mammal, e.g., a human.

In another specific embodiment of the method, said plurality of natural killer cells comprises cells that exhibit detectably lower expression of NKG2D, NKp46 or CD94 than an equivalent number of $CD56^+CD16^+$ natural killer cells. In another specific embodiment, said plurality of natural killer cells, e.g., PINK cells, expresses one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p, hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, and/or hsa-miR-99a at a detectably higher level than peripheral blood natural killer cells.

In another specific embodiment, said plurality of natural killer cells, e.g., PINK cells, are contacted with an immunomodulatory compound in an amount and for a time sufficient for said plurality of natural killer cells to express detectably more granzyme B than an equivalent number of said natural killer cells not contacted with said immunomodulatory compound. In a more specific embodiment, said immunomodulatory compound is lenalidomide or pomalidomide. In another specific embodiment, said plurality of natural killer cells, e.g., PINK cells, are contacted with an immunomodulatory compound in an amount and for a time sufficient for said natural killer cells to exhibit detectably more cytotoxicity towards said tumor cells than an equivalent number of said natural killer cells not contacted with said immunomodulatory compound, e.g., lenalidomide or pomalidomide. In another specific embodiment, said plurality of natural killer cells, e.g., PINK cells, express one or more of BAX, CCL5, CCR5, CSF2, FAS, GUSB, IL2RA, or TNFRSF18 at a higher level than an equivalent number of said natural killer cells not contacted with said immunomodulatory compound. In another specific embodiment, said plurality of natural killer cells, e.g., PINK cells, express one or more of ACTB, BAX, CCL2, CCL3, CCL5, CCR5, CSF1, CSF2, ECE1, FAS, GNLY, GUSB, GZMB, IL1A, IL2RA, IL8. IL10, LTA, PRF1, PTGS2, SKI, and TBX21 at a higher level than an equivalent number of said natural killer cells not contacted with said immunomodulatory compound.

In another embodiment, the natural killer cells from placenta are combined with natural killer cells from another source, e.g., placental blood and/or umbilical cord blood, e.g., to form combined natural killer cells. As used herein, the phrase "natural killer cell(s) from placenta" does not include natural killer cells from umbilical cord blood or placental blood. In more specific embodiments, the natural killer cells from placenta are combined with natural killer cells from another source in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In specific embodiments, the combined natural killer cells are not cultured, and comprise: a detectably higher number of $CD3^-CD56^+CD16^-$ natural killer cells than an equivalent number of natural killer cells from peripheral blood; a detectably lower number of $CD3^-CD56^+CD16^+$ natural killer cells than an equivalent number of natural killer cells from peripheral blood; a detectably higher number of $CD3^-CD56^+$ $KIR2DL2/L3^+$ natural killer cells than an equivalent number of natural killer cells from peripheral blood; a detectably lower number of $CD3^-CD56^+NKp46^+$ natural killer cells than an equivalent number of natural killer cells from peripheral blood; a detectably higher number of $CD3^-CD56^+$ $NKp30^+$ natural killer cells than an equivalent number of natural killer cells from peripheral blood; a detectably higher number of $CD3^-CD56^+2B4^+$ natural killer cells than an equivalent number of natural killer cells from peripheral blood; or a detectably higher number of $CD3^-CD56^+CD94^+$ natural killer cells than an equivalent number of natural killer cells from peripheral blood. In other specific embodiments, the combined natural killer cells are cultured and comprise: a detectably lower number of $CD3^-CD56^+KIR2DL2/L3^+$ natural killer cells than an equivalent number of natural killer cells from peripheral blood; a detectably higher number of $CD3^-CD56^+NKp46^+$ natural killer cells than an equivalent number of natural killer cells from peripheral blood; a detectably higher number of $CD3^-CD56^+NKp44^+$ natural killer cells than an equivalent number of natural killer cells from peripheral blood; a detectably higher number of $CD3^-CD56^+$ $NKp30^+$ natural killer cells than an equivalent number of natural killer cells from peripheral blood.

In a specific embodiment of any of the above methods, the tumor cell is a solid tumor cell. In another specific embodiment, the tumor cell is a liquid tumor cell, e.g., a blood tumor cell. In more specific embodiments, the tumor cell is a primary ductal carcinoma cell, a leukemia cell, an acute T cell leukemia cell, a chronic myeloid lymphoma (CML) cell, an acute myelogenous leukemia cell, a chronic myelogenous leukemia (CML) cell, a lung carcinoma cell, a colon adenocarcinoma cell, a histiocytic lymphoma cell, multiple myeloma cell, a retinoblastoma cell, a colorectal carcinoma cell or a colorectal adenocarcinoma cell.

In another aspect, provided herein is a composition comprising isolated placental $CD56^+$, $CD16^-$ natural killer cells, e.g., PINK cells. In a specific embodiment, said placental natural killer cells are isolated from placental perfusate. In another specific embodiment, said placental natural killer cells are isolated from placenta by physical disruption and/or enzymatic digestion of placental tissue. In another specific embodiment, said natural killer cells comprise at least 50% of cells in the composition. In a specific embodiment, said natural killer cells comprise at least 80% of cells in the composition. In another specific embodiment, said composition comprises isolated $CD56^+$, $CD16^+$ natural killer cells. In a more specific embodiment, said $CD56^+$, $CD16^+$ natural killer cells are from a different individual than said $CD56^+$, $CD16^-$ natural killer cells. In another specific embodiment, said isolated $CD56^+$, $CD16^-$ natural killer cells are from a single individual. In a more specific embodiment, said isolated $CD56^+$, $CD16^-$ natural killer cells comprise natural killer cells from at least two different individuals. In another specific embodiment, said placental natural killer cells, e.g., said PINK cells, are expanded.

In a more specific embodiment, the composition comprises placental natural killer cells and natural killer cells from another source. In a specific embodiment, said other source is cord blood and/or umbilical cord blood. In another specific embodiment, said other source is peripheral blood. In more specific embodiments, the natural killer cells from placenta are combined with natural killer cells from another source in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another specific embodiment, the composition comprises isolated placental perfusate. In a more specific embodiment, said placental perfusate is from the same individual as said natural killer cells. In another more specific embodiment, said placental perfusate comprises placental perfusate from a different individual than said natural killer cells. In another specific embodiment, all, or substantially all (e.g., greater than 90%, 95%, 98% or 99%) of cells in said placental perfusate are fetal cells. In another specific embodiment, the placental perfusate comprises fetal and maternal cells. In a more specific embodiment, the fetal cells in said placental perfusate comprise less than about 90%, 80%, 70%, 60% or 50% of the cells in said perfusate. In another specific embodiment, said perfusate is obtained by passage of a 0.9% NaCl solution through the placental vasculature. In another specific embodiment, said perfusate comprises a culture medium. In another specific embodiment, said perfusate has been treated to remove a plurality of erythrocytes.

In another specific embodiment, the composition comprises placental perfusate cells. In a more specific embodiment, said placental perfusate cells are from the same individual as said natural killer cells. In another more specific embodiment, said placental perfusate cells are from a different individual than said natural killer cells. In another specific embodiment, the composition comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals. The composition can additionally comprise isolated PINK cells, wherein the PINK cells are from a different individual than said placental perfusate or said perfusate cells.

In another aspect, provided herein is a method of isolating placental natural killer cells, comprising obtaining a plurality of placental cells, and isolating natural killer cells from said plurality of placental cells. In a specific embodiment, the placental cells are, or comprise, placental perfusate cells, e.g., total nucleated cells from placental perfusate. In another specific embodiment, said plurality of placental cells are, or comprise, placental cells obtained by mechanical and/or enzymatic digestion of placental tissue. In another embodiment, said isolating is performed using one or more antibodies. In a more specific embodiment, said one or more antibodies comprises one or more of antibodies to CD3, CD16 or CD56. In a more specific embodiment, said isolating comprises isolating $CD56^+$ cells from $CD56^-$ cells in said plurality of placental cells. In a more specific embodiment, said isolating comprises isolating $CD56^+$, $CD16^-$ placental cells from placental cells that are $CD56^-$ or $CD16^+$. In a more specific embodiment, said isolating comprises isolating $CD56^+$, $CD16^-$, $CD3^-$ placental cells from placental cells that are $CD56^-$, $CD16^+$, or $CD3^+$. In another embodiment, said method of isolating placental natural killer cells results in a population of placental cells that is at least 50%, 55%, 60%, 65%, 70%, 75%, 80%, 85%, 90%, 95%, 98% or at least 99% $CD56^+$, $CD16^-$ natural killer cells.

In certain embodiments of the above methods, the placental perfusate cells have been expanded in culture. In various embodiments, the cells have been expanded for at least, about, or no more than, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. In a specific embodiment, said placental perfusate cells have been expanded in the presence of a feeder layer and/or in the presence of at least one cytokine. In a more specific embodiment, said feeder layer comprises K562 cells or peripheral blood mononuclear cells. In another more specific embodiment, said at least one cytokine is interleukin-2.

In another embodiment, provided herein is a method of treating an individual having cancer, comprising administering to said individual a therapeutically effective amount of placental perfusate, placental perfusate cells, placental intermediate natural killer cells, combined natural killer cells, or combinations thereof, as described herein. In certain embodiments, said individual has a solid tumor. In certain other embodiments, the individual has a blood cancer. In specific embodiments, said individual has primary ductal carcinoma, a leukemia, acute T cell leukemia, chronic myeloid lymphoma (CML), acute myelogenous leukemia, chronic myelogenous leukemia (CML), lung carcinoma, colon adenocarcinoma, histiocytic lymphoma, multiple myeloma, retinoblastoma, colorectal carcinoma, or colorectal adenocarcinoma.

3.1. Definitions

As used herein, "combined natural killer cells" are natural killer cells, e.g., from matched umbilical cord and human placental perfusate, wherein placental perfusate is obtained from the same placenta as the cord blood. Natural killer cells from both are isolated separately or at the same time, and combined.

As used herein, "PINK" and "PINK cells" refer to placental intermediate natural killer cells that are obtained from human placenta, e.g., human placental perfusate or placental tissue that has been mechanically and/or enzymatically disrupted. The cells are CD56$^+$ and CD16$^-$, e.g., as determined by flow cytometry, e.g., fluorescence-activated cell sorting using antibodies to CD56 and CD16. PINK cells are not obtained from cord blood or peripheral blood.

As used herein, "placental perfusate" means perfusion solution that has been passed through at least part of a placenta, e.g., a human placenta, e.g., through the placental vasculature, including a plurality of cells collected by the perfusion solution during passage through the placenta.

As used herein, "placental perfusate cells" means nucleated cells, e.g., total nucleated cells, isolated from, or isolatable from, placental perfusate.

As used herein, "tumor cell suppression," "suppression of tumor cell proliferation," and the like, includes slowing the growth of a population of tumor cells, e.g., by killing one or more of the tumor cells in said population of tumor cells, for example, by contacting the population of tumor cells with PINK cells, a population of cells comprising PINK cells, combined natural killer cells, a population of cells comprising combined natural killer cells, human placental perfusate, or the like.

4. BRIEF DESCRIPTION OF THE FIGURES

FIG. 1 shows flow cytometry results using anti-CD3 antibodies and anti-CD56 antibodies for cells selected by CD56 microbeads from human placental perfusate (HPP). The majority of the isolated cells are CD56$^+$CD3$^-$.

Figure 2A:
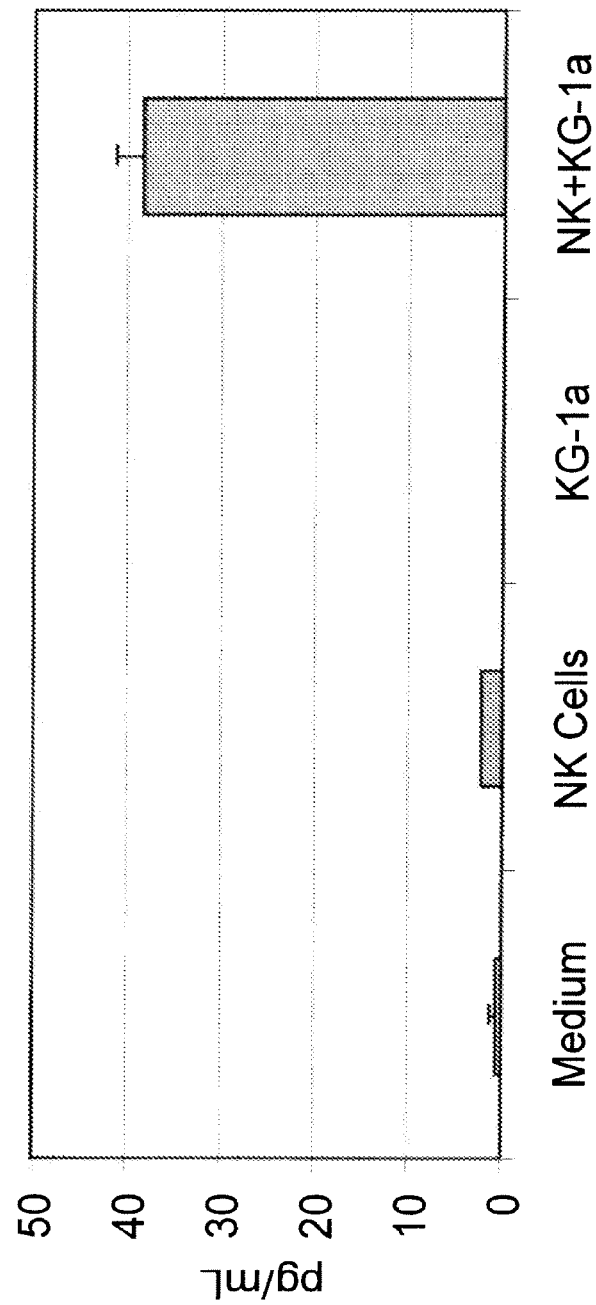
Figure 2B:
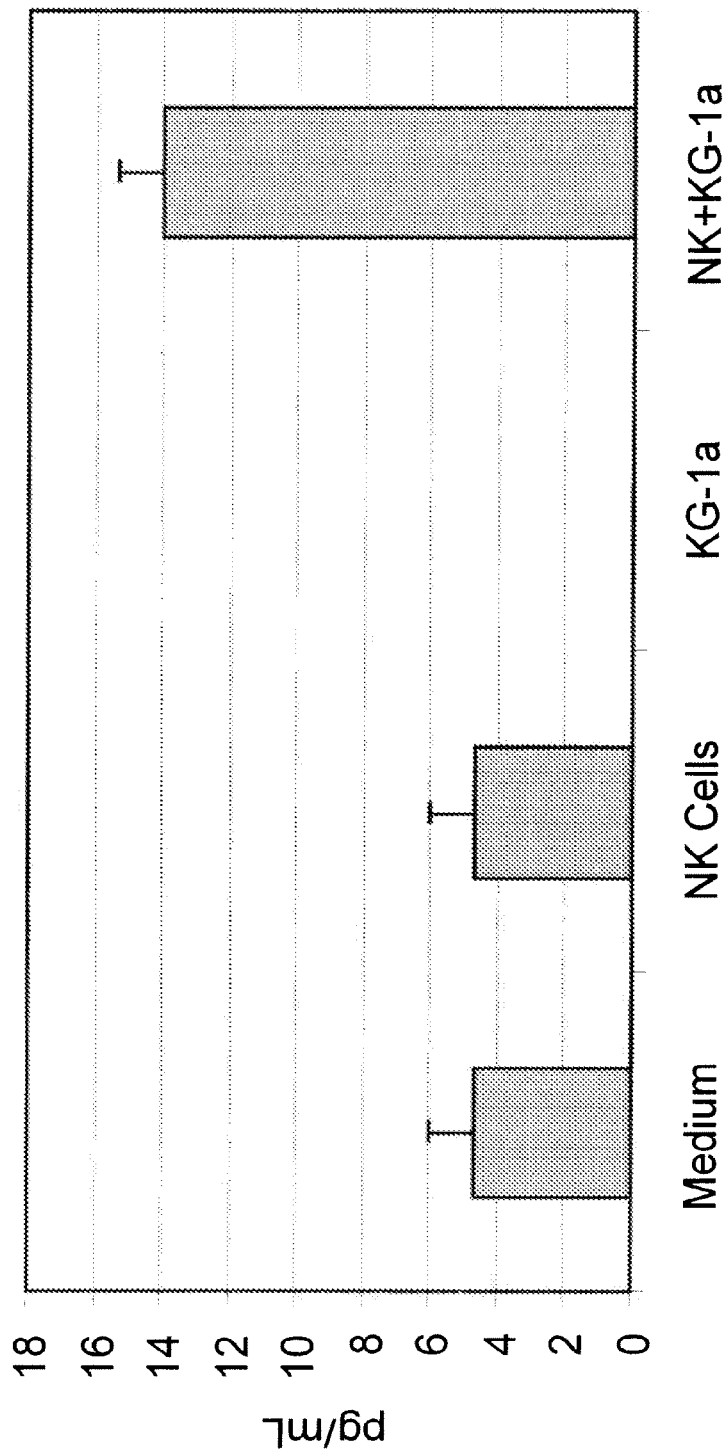

FIG. 2 depicts production of cytokines by PINK cells and/or tumor cells during 24 hour culture. FIG. 2A depicts secretion of interferon gamma (IFNγ) by placental perfusate-derived intermediate natural killer cells (PINK) cells alone or in the presence of KG-1a tumor cells. PINK cells and KG-1a cells were cultured alone or in combination at a ratio of 1:1. Y axis: picograms of IFNγ produced by the cultures. FIG. 2B depicts secretion of granulocyte-macrophage colony stimulating factor (GM-CSF) by PINK cells alone or in the presence of KG-1a tumor cells. PINK cells and KG-1a cells were cultured alone or in combination at a ratio of 1:1. Y axis: picograms of GM-CSF produced by the cultures.

Figure 3:
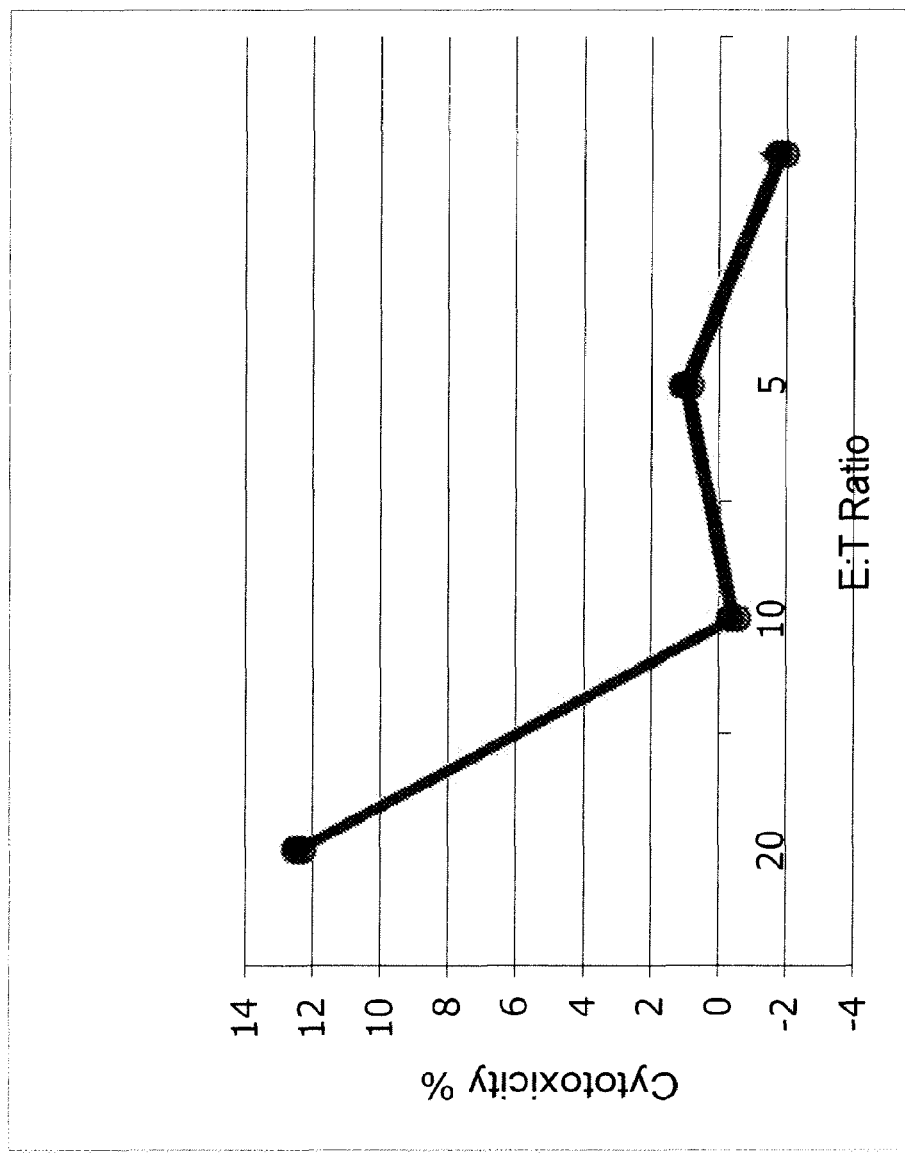

FIG. 3 depicts cytotoxicity of PINK cells to KG-1a tumor cells in 24 hour co-culture at a ratio of 1:1, 5:1, 10:1 or 20:1 PINK cells to tumor cells. X axis: ratio of PINK cells to tumor cells. Y axis: percentage of dead tumor cells compared to tumor cells without PINK cells.

Figure 4:
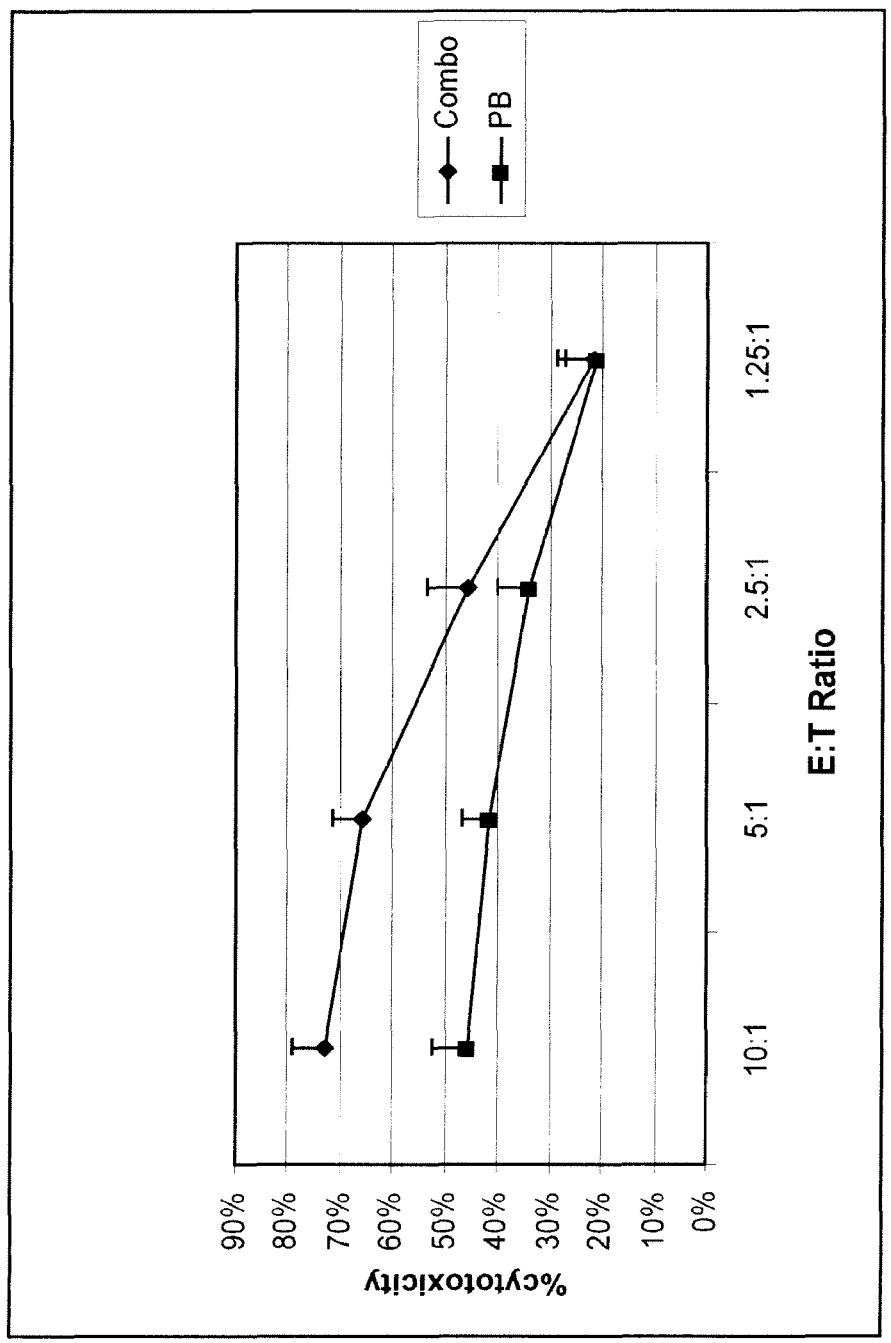

FIG. 4 depicts cytotoxicity of placental NK cells and peripheral blood (PB) NK cells cultured for 21 days towards K562 cells. Error bars stand for standard deviation of 4 units of cultured placental NK cells or 3 units of cultured peripheral blood NK cells.

Figure 5:
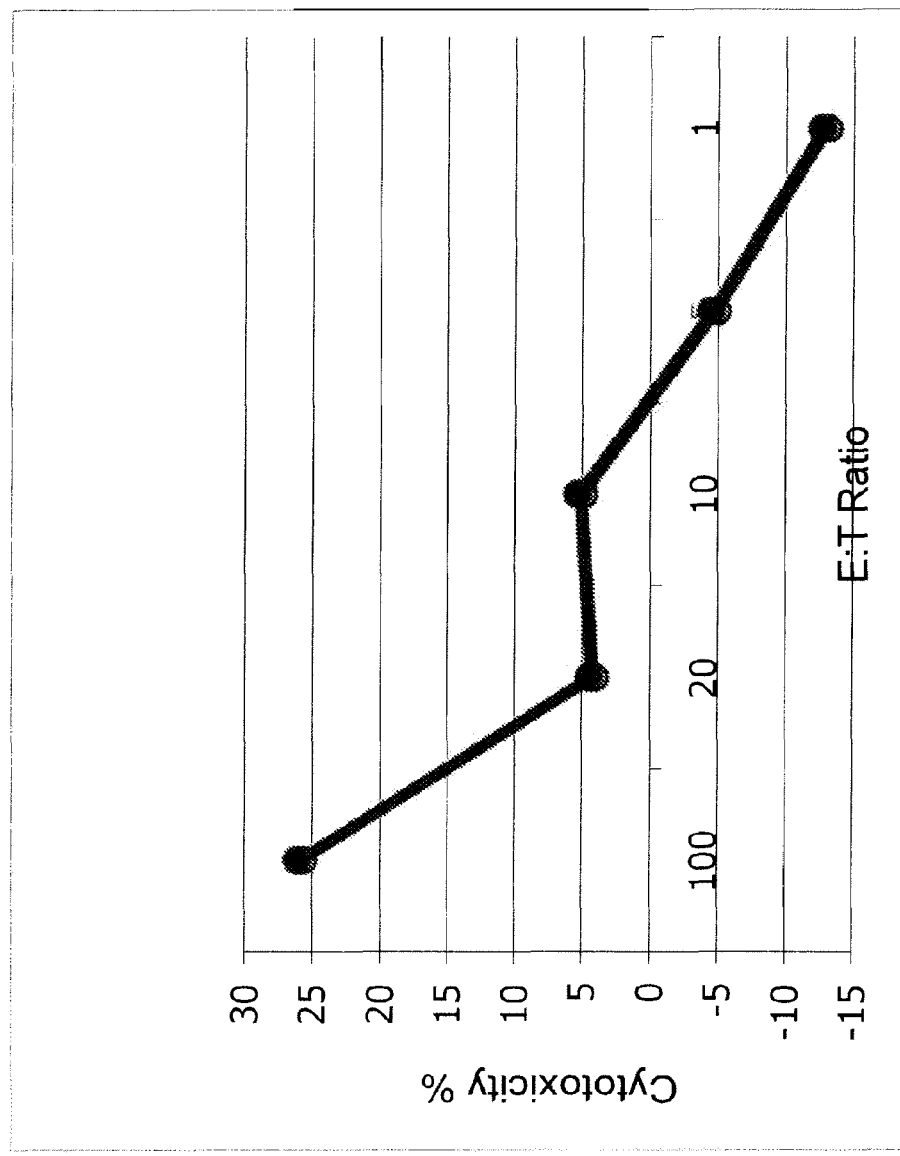

FIG. 5 depicts cytotoxicity of whole human placental perfusate, as obtained from the placenta, to KG-1a tumor cells in 24 hour co-culture at a ratio of 1:1, 5:1, 10:1 or 20:1 or 100:1 HPP cells to tumor cells. X axis: ratio of HPP cells to tumor cells. Y axis: percentage of dead tumor cells compared to tumor cells without HPP cells.

Figure 6:
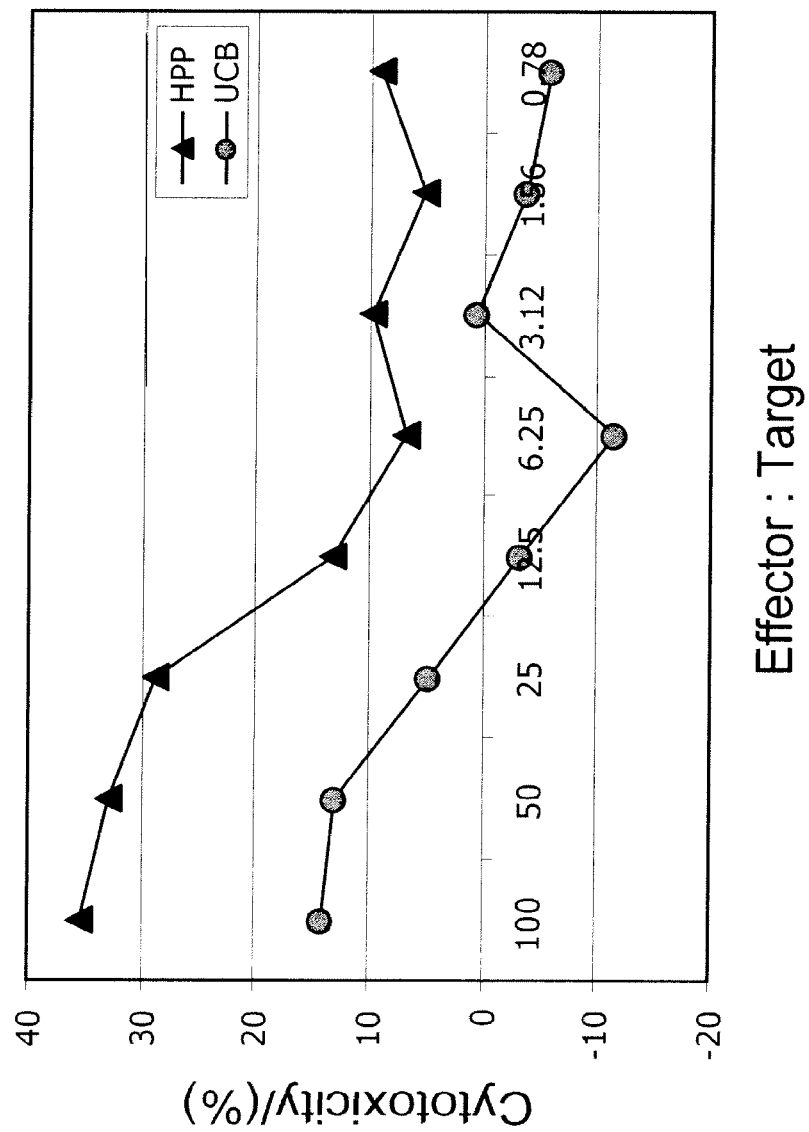

FIG. 6 depicts cytotoxicity of whole human placental perfusate, as obtained from the placenta, and umbilical cord blood, to KG-1a tumor cells in 48 hour co-culture in serial dilutions of 100:1, 50:1, 25:1, 12.5:1, 6.25:1, 3.12:1, 1.56:1 or 0.78:1 HPP cells or UCB cells to tumor cells. X axis: ratio of HPP cells or umbilical cord cells to tumor cells. Y axis: percentage of dead tumor cells after 48 hours culture time compared to tumor cells without HPP cells or umbilical cord cells.

Figure 7:
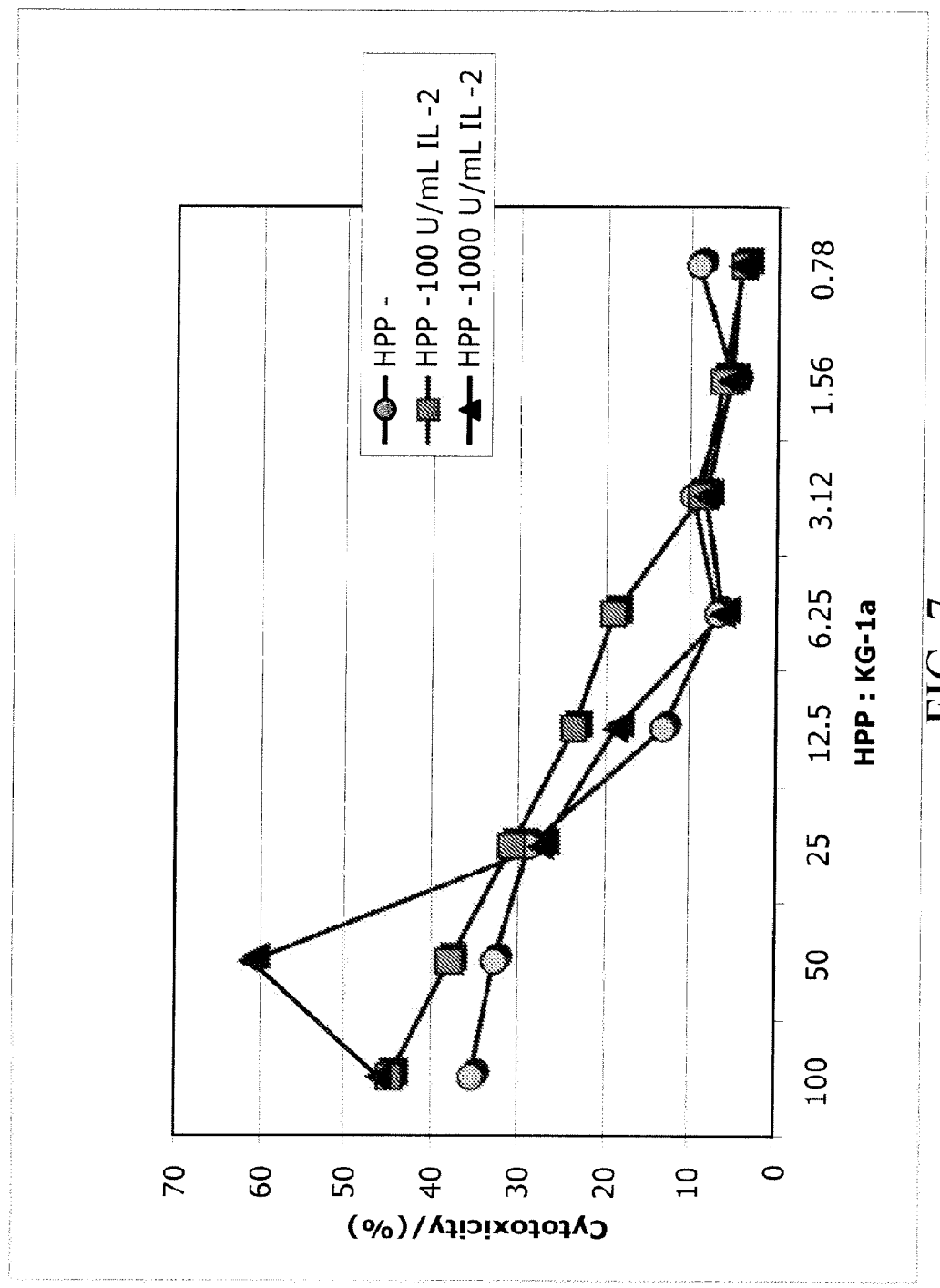

FIG. 7 depicts cytotoxicity of whole human placental perfusate, as obtained from the placenta to KG-1a tumor cells in 48 hour co-culture in serial dilutions of 100:1, 50:1, 25:1, 12.5:1, 6.25:1, 3.12:1, 1.56:1 or 0.78:1 HPP cells to tumor cells. Perfusate was either used as collected, or stimulated for 24 hours with 100 U/mL or 1000 U/mL interleukin-2 (IL-2). X axis: ratio of HPP cells to tumor cells. Y axis: percentage of dead tumor cells after 48 hours culture time compared to tumor cells without HPP cells.

Figure 8A:
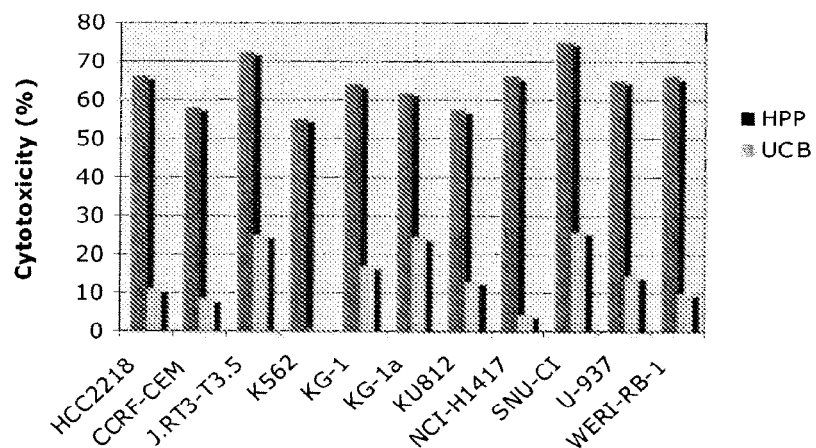
Figure 8B:
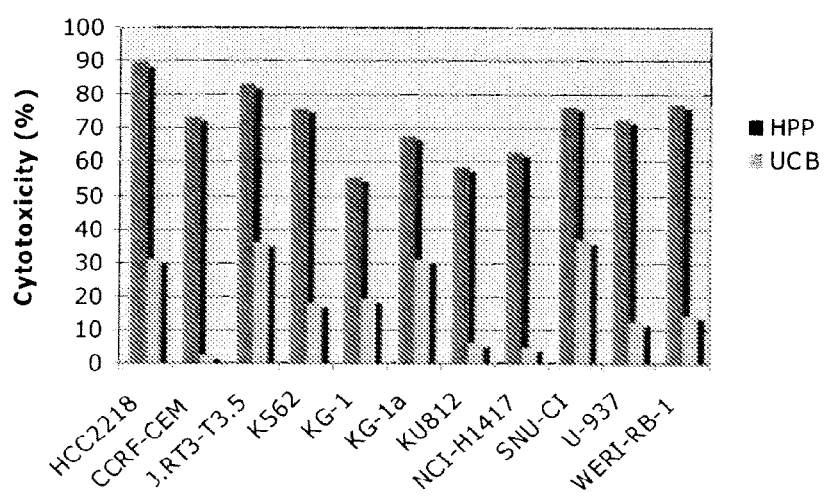

FIG. 8 depicts the cytotoxic effect of human placental perfusate towards a panel of tumor cell lines after culture with HPP or UCB cells at a 50:1 ratio to the tumor cells. FIG. 8A: co-culture for 24 hours. FIG. 8B: co-culture for 48 hours. X axis: tumor cell line tested. Y axis: percentage of dead tumor cells after co-culture, compared to the number of tumor cells in the absence of tumor cells.

Figure 9:
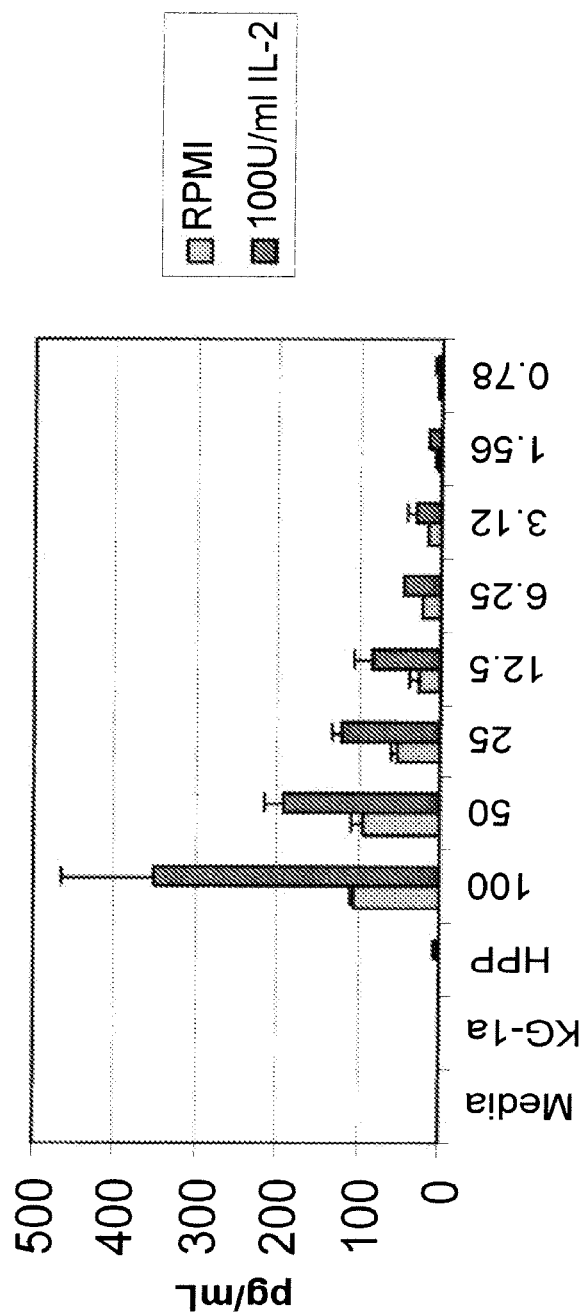

FIG. 9 depicts IFNγ production by HPP cells co-cultured with KG-1a tumor cells at different ratios of HPP cells to tumor cells. X axis: Experimental conditions, including ratio of HPP cells to tumor cells Y axis: IFNγ levels per milliliter after 24 hours co-culture.

Figures 10A, 10B:
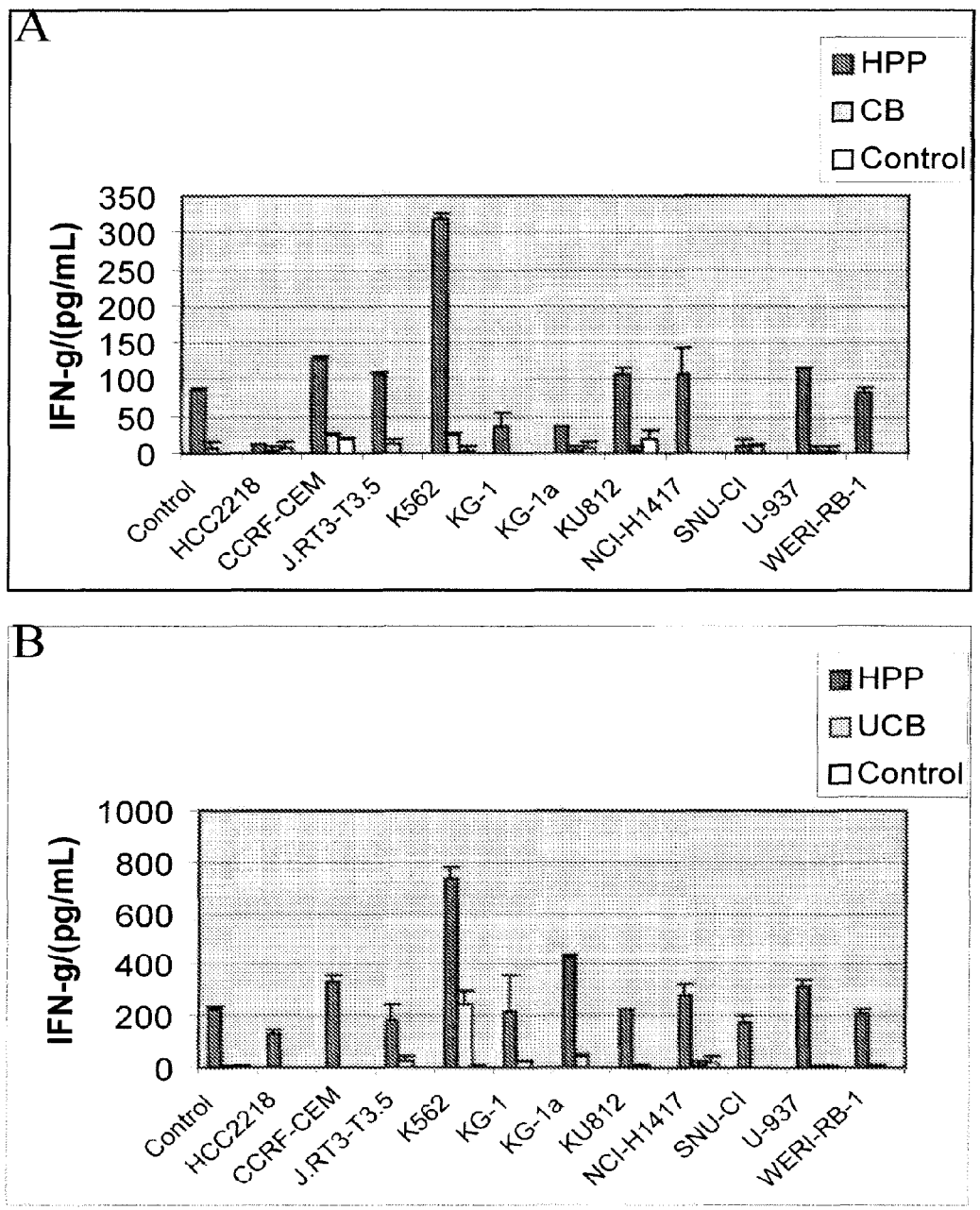

FIG. 10 Production of IFNγ by HPP or UCB cells in co-culture with a panel of tumor cells. HPP or UCB cells were co-cultured at a ratio of 50:1 with tumor cell lines for 24 hours (FIG. 10A) or 48 hours (FIG. 10B). IFNγ levels were determined by Luminex assay (HCYTO-60K-03, Millipore). X axis: tumor cell line tested. Y axis: picograms of IFNγ produced by HPP or UCB cells, compared to picograms of IFNγ produced in the absence of tumor cells.

Figure 11:
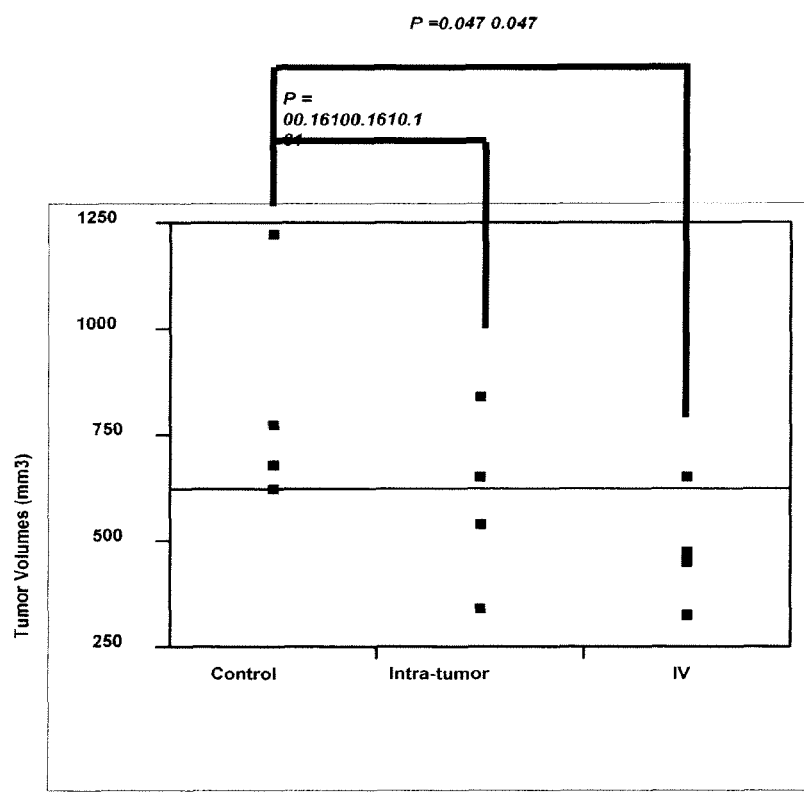

FIG. 11 depicts the reduction in tumor size upon administration of 2×10$^7$ human placental perfusate (HPP) cells to mice having KG-1 cell tumors approximately 332 mm$^3$ in volume. Intra-tumor—HPP cells were injected directly into the subcutaneous tumor site. IV—HPP cells administered intravenously. Control—vehicle administration only. Tumor volumes in mm$^3$.

5. DETAILED DESCRIPTION

Provided herein is the use of placental perfusate, placental perfusate cells, and/or placental perfusate-derived natural killer ("PINK") cells obtained from placenta to suppress the growth or proliferation of a tumor cell or plurality of tumor cells. In particular, provided herein are natural killer (NK) cells, and populations of NK cells, isolated from placental perfusate, e.g., human placental perfusate, or isolated from placental tissue that has been disrupted mechanically and/or enzymatically, methods of obtaining the NK cells, and methods of using the cells. Provided herein are also populations of cells, e.g., populations of placental cells, comprising natural killer cells. Methods of obtaining placental perfusate, and obtaining cells from placental perfusate, are described in Section 5.1, below. Placental perfusate-derived natural killer cells, and methods of obtaining the cells, are described in Section 5.2, below. Methods of using the placental perfusate, placental perfusate-derived cells or placental perfusate-derived natural killer cells, e.g., intermediate natural killer cells, to suppress the proliferation of tumor cells, are described in Section 5.3, below.

5.1. Placental Perfusate
5.1.1. Cell Collection Composition

The placental perfusate, perfusate cells and placental perfusate-derived natural killer cells provided herein can be collected by perfusion of a mammalian, e.g., human post-partum placenta using a placental cell collection composition. Perfusate can be collected from the placenta by perfusion of the placenta with any physiologically-acceptable solution, e.g., a saline solution, culture medium, or a more complex cell collection composition. A cell collection composition suitable for perfusing a placenta, and for the collection and preservation of perfusate cells, e.g., total nucleated placental perfusate cells or PINK cells, is described in detail in related U.S. Application Publication No. 2007/0190042, which are incorporated herein by reference in their entireties.

The cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve placental cells, that is, prevent the placental cells from dying, or delay the death of the placental cells, reduce the number of placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, a hyaluronidase, an RNase, or a DNase, or the like. Such enzymes include, but are not limited to, collagenases (e.g., collagenase I, II, III or IV, a collagenase from Clostridium histolyticum, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., Pseudomonas aeruginosa, Staphylococcus aureus, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.1.2. Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the cells harvested therefrom. For example, human placental cells can be used, in light of the medical history, for personalized medicine for the infant associated with the placenta, or for parents, siblings or other relatives of the infant.

Prior to recovery of perfusate, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415, 665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and CryoCell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of perfusate. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to collection of the perfusate, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5° C. to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental perfusate is collected.

5.1.3. Placental Perfusion

Methods of perfusing mammalian placentae are disclosed, e.g., in Hariri, U.S. Pat. Nos. 7,045,148 and 7,255,879, and in U.S. Application Publication No. 2007/0190042, entitled "Improved Composition for Collecting and Preserving Organs", the disclosures of which are hereby incorporated by reference herein in their entireties.

Perfusate can be obtained by passage of perfusion solution, e.g., saline solution, culture medium or cell collection compositions described above, through the placental vasculature. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented in such a manner that the umbilical artery and umbilical vein are located at the highest point of the placenta. The placenta can be perfused by passage of a perfusion solution through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins, that is, is passed through only the placental vasculature (fetal tissue).

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoirs) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 mL of perfusion fluid is adequate to initially flush blood from the placenta, but more or less perfusion fluid may be used depending on the observed results.

The volume of perfusion liquid used to perfuse the placenta may vary depending upon the number of placental cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with a cell collection composition, or a standard perfusion solution (e.g., a normal saline solution such as phosphate buffered saline ("PBS") with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., placental cell collection composition, is repeated until the number of recovered nucleated cells falls below 100 cells/ml. The perfusates at different time points can be further processed individually to recover time-dependent populations of cells, e.g., total nucleated cells. Perfusates from different time points can also be pooled.

5.1.4. Placental Perfusate and Placental Perfusate Cells

Placental perfusate comprises a heterogeneous collection of cells. Typically, placental perfusate is depleted of erythrocytes prior to use. Such depletion can be carried out by known methods of separating red blood cells from nucleated blood cells. In certain embodiment, the perfusate or perfusate cells are cryopreserved. In certain other embodiments, the placental perfusate comprises, or the perfusate cells comprise, only fetal cells, or a combination of fetal cells and maternal cells.

Typically, placental perfusate from a single placental perfusion comprises about 100 million to about 500 million nucleated cells. In certain embodiments, the placental perfusate or perfusate cells comprise $CD34^+$ cells, e.g., hematopoietic stem or progenitor cells. Such cells can, in a more specific embodiment, comprise $CD34^+CD45^-$ stem or progenitor cells, $CD34^+CD45^+$ stem or progenitor cells, myeloid progenitors, lymphoid progenitors, and/or erythroid progenitors. In other embodiments, placental perfusate and placental perfusate cells comprise adherent placental stem cells, e.g., $CD34^-$ stem cells. In other embodiment, the placental perfusate and placental perfusate cells comprise, e.g., endothelial progenitor cells, osteoprogenitor cells, and natural killer cells. In certain embodiments, placental perfusate as collected from the placenta and depleted of erythrocytes, or perfusate cells isolated from such perfusate, comprise about 6-7% natural killer cells ($CD3^-$, $CD56^+$); about 21-22% T cells ($CD3^+$); about 6-7% B cells ($CD19^+$); about 1-2% endothelial progenitor cells ($CD34^+$, $CD31^+$); about 2-3% neural progenitor cells (nestin$^+$); about 2-5% hematopoietic progenitor cells ($CD34^+$); and about 0.5-1.5% adherent placental stem cells (e.g., $CD34^-$, $CD117^-$, $CD105^+$ and $CD44^+$), as determined, e.g. by flow cytometry, e.g., by FACS analysis.

5.2. Disruption and Digestion of Placental Tissue to Obtain PINK Cells

Placental natural killer cells, e.g., PINK cells, can be obtained from placental tissue that has been mechanically and/or enzymatically disrupted.

Placental tissue can be disrupted using one or more tissue-degrading enzymes, e.g., a metalloprotease, a serine protease, a neutral protease, an RNase, or a DNase, or the like. Such enzymes include, but are not limited to, collagenases (e.g. collagenase I, II, III or IV, a collagenase from *Clostridium histolyticum*, etc.); dispase, thermolysin, elastase, trypsin, LIBERASE, hyaluronidase, and the like. Typically after digestion, the digested tissue is passed through a strainer or filter to remove partially-digested cell clumps, leaving a substantially single-celled suspension.

After a suspension of placental cells is obtained, natural killer cells can be isolated using, e.g., antibodies to CD3 and CD56. In a specific embodiment, placental natural killer cells are isolated by selecting for cells that are $CD56^+$ to produce a first cell population; contacting said first cell population with antibodies specific for CD3 and/or CD16; and removing cells from said first cell population that are $CD3^+$ or $CD56^+$, thereby producing a second population of cells that is substantially $CD56^+$ and $CD3^-$, $CD56^+$ and $CD16^-$, or $CD56^+$, $CD3^-$ and $CD16^-$.

In one embodiment, magnetic beads are used to isolate placental natural killer cells from a suspension of placental cells. The cells may be isolated, e.g., using a magnetic activated cell sorting (MACS) technique, a method for separating particles based on their ability to bind magnetic beads (e.g., about 0.5-100 µm diameter) that comprise one or more specific antibodies, e.g., anti-CD56 antibodies. A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

5.3. Placental Natural Killer Cells

In one aspect, provided herein is the isolation, characterization, and use of natural killer cells obtainable from placenta, e.g., from placental perfusate and/or from mechanically and/or enzymatically-disrupted placental tissue, and of compositions comprising such natural killer cells. In a specific embodiment, the placental natural killer cells are "placental intermediate natural killer cells," or "PINK" cells, are characterized as being $CD56^+CD16^-$, i.e., displaying the CD56 cellular marker and lacking the CD16 cellular marker, e.g., as determined by flow cytometry, e.g., fluorescence-activated cell sorting using antibodies against CD16 and CD56, as described above. As such, provided herein are isolated PINK cells and isolated pluralities of PINK cells. Also provided herein are isolated pluralities of cells comprising $CD56^+CD16^-$ PINK cells in combination with $CD56^+CD16^+$ natural killer cells. In more specific embodiments, the CD56+ CD16+ natural killer cells can be isolated from placenta, or from another source, e.g., peripheral blood, umbilical cord blood, bone marrow, or the like. Thus, in various other embodiments, PINK cells can be combined with CD56+ CD16+ natural killer cells, e.g., in ratios of, for example, about 1:10, 2:9, 3:8, 4:7:, 5:6, 6:5, 7:4, 8:3, 9:2, 1:10, 1:9, 1:8, 1:7, 1:6, 1:5, 1:4, 1:3, 1:2, 1:1, 2:1, 3:1, 4:1, 5:1, 6:1, 7:1, 8:1 or about 9:1. As used in this context, "isolated" means that the cells have been removed from their normal environment, e.g., the placenta.

In certain embodiments, the PINK cells are CD3−.

In other embodiments, the PINK cells do not exhibit one or more cellular markers exhibited by fully mature natural killer cells (e.g., CD16), or exhibit such one or more markers at a detectably reduced level compared to fully mature natural killer cells, or exhibit one or more cellular markers associated with natural killer cell precursors but not fully mature natural killer cells. In a specific embodiment, a PINK cell provided herein expresses NKG2D, CD94 and/or NKp46 at a detectably lower level than a fully mature NK cell. In another specific embodiment, a plurality of PINK cells provided herein expresses, in total, NKG2D, CD94 and/or NKp46 at a detectably lower level than an equivalent number of fully mature NK cells.

In certain embodiments, PINK cells express one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p, hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, and/or hsa-miR-99a at a detectably higher level than peripheral blood natural killer cells.

In certain embodiments, the placental natural killer cells, e.g., PINK cells, have been expanded in culture. In certain other embodiments, the placental perfusate cells have been expanded in culture. In a specific embodiment, said placental perfusate cells have been expanded in the presence of a feeder layer and/or in the presence of at least one cytokine. In a more specific embodiment, said feeder layer comprises K562 cells or peripheral blood mononuclear cells. In another more specific embodiment, said at least one cytokine is interleukin-2.

In another embodiment, provided herein is an isolated plurality (e.g., population) of PINK cells. In another specific embodiment, the isolated population of cells is produced by CD56-microbead isolation of cells from placental perfusate. In various specific embodiments, the population comprises at least about 50%, 55%, 60%, 65%, 70%, 75%, 80%, 85%, 90%, 95%, 98% or at least about 99% PINK cells. In another embodiment, the plurality of PINK cells comprises, or consists of, PINK cells that have not been expanded; e.g., are as collected from placental perfusate. In another embodiment, the plurality of PINK cells comprise, or consist of, PINK cells that have been expanded. Methods of expanding natural killer cells have been described, e.g., in Ohno et al., U.S. Patent Application Publication No. 2003/0157713; see also Yssel et al., *J. Immunol. Methods* 72(1):219-227 (1984) and Litwin et al., J. Exp. Med. 178(4):1321-1326 (1993) and the description of natural killer cell expansion in Example 1, below.

In other embodiments, the isolated plurality of PINK cells does not exhibit one or more cellular markers exhibited by fully mature natural killer cells (e.g., CD16), or exhibits such one or more markers at a detectably reduced level compared to fully mature natural killer cells, or exhibits one or more cellular markers associated with natural killer cell precursors but not associated with fully mature natural killer cells. In a specific embodiment, a PINK cell provided herein expresses NKG2D, CD94 and/or NKp46 at a detectably lower level than a fully mature NK cell. In another specific embodiment, a plurality of PINK cells provided herein expresses, in total, NKG2D, CD94 and/or NKp46 at a detectably lower level than an equivalent number of fully mature NK cells.

In certain specific embodiments, the population of PINK cells expresses one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p, hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, and/or hsa-miR-99a at a detectably higher level than peripheral blood natural killer cells. In another specific embodiment, the population of PINK cells expresses a detectably higher amount of granzyme B than an equivalent number of peripheral blood natural killer cells.

In other embodiments, the PINK cells provided herein have been expanded in culture. In specific embodiments, the PINK cells have been cultured, e.g., expanded in culture, for at least, about, or at most 1, 2, 3, 4, 5, 6, 7, 8, 9, 10, 11, 12, 13, 14, 15, 16, 17, 18, 19, 20, 21, 22, 23, 24, 25, 26, 27 or 28 days. In a specific embodiment, the PINK cells are cultured for about 21 days.

In another embodiment, provided herein is an isolated population of cells, e.g., placental cells, comprising PINK cells. In a specific embodiment, the isolated population of cells is total nucleated cells from placental perfusate, e.g., placental perfusate cells, comprising autologous, isolated PINK cells. In another specific embodiment, the population of cells is an isolated population of cells produced by CD56-microbead isolation of cells from placental perfusate. In various specific embodiments, the population comprises at least about 50%, 55%, 60%, 65%, 70%, 75%, 80%, 85%, 90%, 95%, 98% or at least about 99% PINK cells.

Because the post-partum placenta comprises tissue and cells from the fetus and from the mother placental perfusate, depending upon the method of collection, can comprise fetal cells only, or a substantial majority of fetal cells (e.g., greater than about 90%, 95%, 98% or 99%), or can comprise a mixture of fetal and maternal cells (e.g., the fetal cells comprise less than about 90%, 80%, 70%, 60%, or 50% of the total nucleated cells of the perfusate). In one embodiment, the PINK cells are derived only from fetal placental cells, e.g., cells obtained from closed-circuit perfusion of the placenta (see above) wherein the perfusion produces perfusate comprising a substantial majority, or only, fetal placental cells. In another embodiment, the PINK cells are derived from fetal and maternal cells, e.g., cells obtained by perfusion by the pan method (see above), wherein the perfusion produced perfusate comprising a mix of fetal and maternal placental cells. Thus, in one embodiment, provided herein is a population of placenta-derived intermediate natural killer cells, the substantial majority of which have the fetal genotype. In another embodiment, provided herein is a population of placenta-derived intermediate natural killer cells that comprise natural killer cells having the fetal genotype and natural killer cells having the maternal phenotype.

Also provided herein are populations of placenta-derived intermediate natural killer cells that comprise natural killer cells from a non-placental source. For example, in one embodiment, provided herein is population of PINK cells that also comprises natural killer cells from umbilical cord blood, peripheral blood, bone marrow, or a combination of two or more of the foregoing. The populations of natural killer cells comprising PINK cells and natural killer cells from a non-placental source can comprise the cells in, e.g., a ratio of about 1:10, 2:9, 3:8, 4:7:, 5:6, 6:5, 7:4, 8:3, 9:2, 10:1, 1:9, 1:8, 1:7, 1:6, 1:5, 1:4, 1:3, 1:2, 1:1, 2:1, 3:1, 4:1, 5:1, 6:1, 7:1, 8:1, 9:1, 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or about 1:100, or the like.

Further provided herein are combinations of umbilical cord blood and isolated PINK cells. In various embodiments, cord blood is combined with PINK cells at about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, or $5 \times 10^8$, or more, PINK cells per milliliter of cord blood.

Also provided herein are methods of isolating PINK cells. In one embodiment, PINK cells are collected by obtaining placental perfusate, then contacting the placental perfusate with a composition that specifically binds to $CD56^+$ cells, e.g., an antibody against CD56, followed by isolating of $CD56^+$ cells on the basis of said binding to form a population of $CD56^+$ cells. The population of $CD56^+$ cells comprises an isolated population of natural killer cells. In a specific embodiment, $CD56^+$ cells are contacted with a composition that specifically binds to $CD16^+$ cells, e.g., an antibody against CD16, and the $CD16^+$ cells from the population of $CD56^+$ cells. In another specific embodiment, $CD3^+$ cells are also excluded from the population of $CD56^+$ cells.

In one embodiment, PINK cells are obtained from placental perfusate as follows. Post-partum human placenta is exsanguinated and perfused, e.g., with about 200-800 mL of perfusion solution, through the placental vasculature only. In a specific embodiment, the placenta is drained of cord blood and flushed, e.g., with perfusion solution, through the placental vasculature to remove residual blood prior to said perfusing. The perfusate is collected and processed to remove any residual erythrocytes. Natural killer cells in the total nucleated cells in the perfusate can be isolated on the basis of expression of CD56 and CD16. In certain embodiments, the isolation of PINK cells comprises isolation using an antibody to CD56, wherein the isolated cells are $CD56^+$. In another embodiment, the isolation of PINK cells comprises isolation using an antibody to CD16, wherein the isolated cells are CD16. In another embodiment, the isolation of PINK cells comprises isolation using an antibody to CD56, and exclusion of a plurality of non-PINK cells using an antibody to CD16, wherein the isolated cells comprise $CD56^+$, $CD16^-$ cells.

Cell separation can be accomplished by any method known in the art, e.g., fluorescence-activated cell sorting (FACS), or, preferably, magnetic cell sorting using microbeads conjugated with specific antibodies. Magnetic cell separation can be performed and automated using, e.g, an AUTOMACS™ Separator (Miltenyi).

In another aspect, provided herein is a method of isolating placental natural killer cells, comprising obtaining a plurality of placental cells, and isolating natural killer cells from said plurality of placental cells. In a specific embodiment, the placental cells are, or comprise, placental perfusate cells, e.g., total nucleated cells from placental perfusate. In another specific embodiment, said plurality of placental cells are, or comprise, placental cells obtained by mechanical and/or enzymatic digestion of placental tissue. In another embodiment, said isolating is performed using one or more antibodies. In a more specific embodiment, said one or more antibodies comprises one or more of antibodies to CD3, CD16 or CD56. In a more specific embodiment, said isolating comprises isolating $CD56^+$ cells from $CD56^-$ cells in said plurality of placental cells. In a more specific embodiment, said isolating comprises isolating $CD56^+$, $CD16^-$ placental cells, e.g., placental natural killer cells, e.g., PINK cells, from placental cells that are $CD56^-$ or $CD16^+$. In a more specific embodiment, said isolating comprises isolating $CD56^+$, $CD16^-$, $CD3^-$ placental cells from placental cells that are $CD56^-$, $CD16^+$, or $CD3^+$. In another embodiment, said method of isolating placental natural killer cells results in a population of placental cells that is at least 50%, 55%, 60%, 65%, 70%, 75%, 80%, 85%, 90%, 95%, 98% or at least 99% $CD56^+$, $CD16^-$ natural killer cells.

5.4. Placental Natural Killer Cells from Matched Perfusate and Cord Blood

Further provided herein are natural killer cells obtained, and obtainable from, combinations of matched units of placental perfusate and umbilical cord blood, referred to herein as combined natural killer cells. "Matched units," as used herein, indicates that the NK cells are obtained from placental perfusate cells, and umbilical cord blood cells, wherein the umbilical cord blood cells are obtained from umbilical cord blood from the placenta from which the placental perfusate is obtained, i.e., the placental perfusate cells and umbilical cord blood cells, and thus the natural killer cells from each, are from the same individual.

In certain embodiments, the combined placental killer cells comprise only, or substantially only, natural killer cells that are $CD56^+$ and $CD16^-$. In certain other embodiments, the combined placental killer cells comprise NK cells that are $CD56^+$ and $CD16^-$, and NK cells that are $CD56^+$ and $CD16^+$. In certain specific embodiments, the combined placental killer cells comprise at least 50%, 60%, 70%, 80%, 90%, 95%, 96%, 97%, 98%, 99% or 99.5% $CD56^+CD16^-$ natural killer cells (PINK cells).

In one embodiment, the combined natural killer cells have not been cultured. In a specific embodiment, the combined natural killer cells comprise a detectably higher number of $CD3^-CD56^+CD16^-$ natural killer cells than an equivalent number of natural killer cells from peripheral blood. In another specific embodiment, the combined natural killer cells comprise a detectably lower number of $CD3^-CD56^+CD16^-$ natural killer cells than an equivalent number of natural killer cells from peripheral blood. In another specific embodiment, the combined natural killer cells comprise a detectably higher number of $CD3^-CD56^+K1R2DL2/L3^+$ natural killer cells than an equivalent number of natural killer cells from peripheral blood. In another specific embodiment, the combined natural killer cells comprise a detectably lower number of $CD3^-CD56^+$ $NKp46^+$ natural killer cells than an equivalent number of natural killer cells from peripheral blood. In another specific embodiment, the combined natural killer cells comprise a detectably lower number of $CD3^-CD56^+$ $NKp30^+$ natural killer cells than an equivalent number of natural killer cells from peripheral blood. In another specific embodiment, the combined natural killer cells comprise a detectably lower number of $CD3^-CD56^+2B4^+$ natural killer cells than an equivalent number of natural killer cells from peripheral blood. In another specific embodiment, the combined natural killer cells comprise a detectably lower number of $CD3^-CD56^+CD94^+$ natural killer cells than an equivalent number of natural killer cells from peripheral blood.

In another embodiment, the combined natural killer cells have been cultured, e.g., for 21 days. In a specific embodiment, the combined natural killer cells comprise a detectably lower number of $CD3^-CD56^+KIR2DL2/L3^+$ natural killer cells than an equivalent number of natural killer cells from peripheral blood. In another specific embodiment, the combined natural killer cells have not been cultured. In another specific embodiment, the combined natural killer cells comprise a detectably higher number of $CD3^-CD56^+NKp44^+$ natural killer cells than an equivalent number of natural killer cells from peripheral blood. In a specific embodiment, the combined natural killer cells comprise a detectably higher number of $CD3^-CD56^+NKp30^+$ natural killer cells than an equivalent number of natural killer cells from peripheral blood.

In another embodiment, the combined natural killer cells express a detectably higher amount of granzyme B than an equivalent number of peripheral blood natural killer cells.

Further provided herein are combinations of umbilical cord blood and combined natural killer cells. In various embodiments, cord blood is combined with combined natural killer cells at about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ combined natural killer cells per milliliter of cord blood.

5.5. Perfusate/Cell Combinations

In addition to placental perfusate, placental perfusate cells, combined natural killer cells, and placental natural killer cells, e.g., placental intermediate natural killer cells, provided herein are compositions comprising the perfusate or cells, for use in suppressing the proliferation of a tumor cell or plurality of tumor cells.

5.5.1. Combinations of Placental Perfusate, Perfusate Cells And Placenta-Derived Intermediate Natural Killer Cells Further provided herein are compositions comprising combinations of the placental perfusate, placental perfusate cells, placental intermediate natural killer cells, and/or combined natural killer cells described in Sections 5.1, 5.3, or 5.4 above. In one embodiment, for example, provided herein is a volume of placental perfusate supplemented with a plurality of placental perfusate cells and/or a plurality of placental natural killer cells, e.g., placental intermediate natural killer cells, for example, obtained from placental perfusate cells or placental tissue mechanically or enzymatically disrupted. In specific embodiments, for example, each milliliter of placental perfusate is supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental perfusate cells, placental intermediate natural killer cells, and/or combined natural killer cells. In another embodiment, a plurality of placental perfusate cells is supplemented with placental perfusate, placental intermediate natural killer cells, and/or combined natural killer cells. In another embodiment, a plurality of placental intermediate natural killer cells is supplemented with placental perfusate, placental perfusate cells, and/or combined natural killer cells. In certain embodiments, when perfusate is used for supplementation, the volume of perfusate is about, greater than about, or less than about, 50%, 45%, 40%, 35%, 30%, 25%, 20%, 15%, 10%, 8%, 6%, 4%, 2% or 1% of the total volume of cells (in solution) plus perfusate. In certain other embodiments, when placental perfusate cells are combined with a plurality of PINK cells and/or combined natural killer cells, the placental perfusate cells generally comprise about, greater than about, or fewer than about, 50%, 45%, 40%, 35%, 30%, 25%, 20%, 15%, 10%, 8%, 6%, 4%, 2% or 1% of the total number of cells. In certain other embodiments, when PINK cells are combined with a plurality of placental perfusate cells and/or combined natural killer cells, the PINK cells generally comprise about, greater than about, or fewer than about, 50%, 45%, 40%, 35%, 30%, 25%, 20%, 15%, 10%, 8%, 6%, 4%, 2% or 1% of the total number of cells. In certain other embodiments, when combined natural killer cells are combined with PINK cells and/or placental perfusate cells, the combined natural killer cells generally comprise about, greater than about, or fewer than about, 50%, 45%, 40%, 35%, 30%, 25%, 20%, 15%, 10%, 8%, 6%, 4%, 2% or 1% of the total number of cells. In certain other embodiments, when PINK cells, combined natural killer cells or placental perfusate cells are used to supplement placental perfusate, the volume of solution (e.g., saline solution, culture medium or the like) in which the cells are suspended comprises about, greater than about, or less than about, 50%, 45%, 40%, 35%, 30%, 25%, 20%, 15%, 10%, 8%, 6%, 4%, 2% or 1% of the total volume of perfusate plus cells, where the PINK cells are suspended to about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter prior to supplementation.

In other embodiments, any of the above combinations is, in turn, combined with umbilical cord blood or nucleated cells from umbilical cord blood.

Further provided herein is pooled placental perfusate that is obtained from two or more sources, e.g., two or more placentas, and combined, e.g., pooled. Such pooled perfusate can comprise approximately equal volumes of perfusate from each source, or can comprise different volumes from each source. The relative volumes from each source can be randomly selected, or can be based upon, e.g., a concentration or amount of one or more cellular factors, e.g., cytokines, growth factors, hormones, or the like; the number of placental cells in perfusate from each source; or other characteristics of the perfusate from each source. Perfusate from multiple perfusions of the same placenta can similarly be pooled.

Similarly, provided herein are placental perfusate cells, and placenta-derived intermediate natural killer cells, that are obtained from two or more sources, e.g., two or more placentas, and pooled. Such pooled cells can comprise approximately equal numbers of cells from the two or more sources, or different numbers of cells from one or more of the pooled sources. The relative numbers of cells from each source can be selected based on, e.g., the number of one or more specific cell types in the cells to be pooled, e.g., the number of $CD34^+$ cells, the number of $CD56^+$ cells, etc.

Pools can comprise, e.g., placental perfusate supplemented with placental perfusate cells; placental perfusate supplemented with placenta-derived intermediate natural killer (PINK) cells; placental perfusate supplemented with both placental perfusate cells and PINK cells; placental perfusate cells supplemented with placental perfusate; placental perfusate cells supplemented with PINK cells; placental perfusate cells supplemented with both placental perfusate and PINK cells; PINK cells supplemented with placental perfusate; PINK cells supplemented with placental perfusate cells; or PINK cells supplemented with both placental perfusate cells and placental perfusate.

Further provided herein are placental perfusate, placental perfusate cells, and placental intermediate natural killer cells, and pools of the same or combinations of the same, that have been assayed to determine the degree or amount of tumor suppression (that is, the potency) to be expected from, e.g., a given number of placental perfusate or PINK cells, or a given volume of perfusate. For example, an aliquot or sample number of cells is contacted with a known number of tumor cells under conditions in which the tumor cells would otherwise proliferate, and the rate of proliferation of the tumor cells in the presence of placental perfusate, perfusate cells, placental natural killer cells, or combinations thereof, over time (e.g., 1, 2, 3, 4, 5, 6, 7, 8, 9, or 10 weeks, or longer) is compared to the proliferation of an equivalent number of the tumor cells in the absence of perfusate, perfusate cells, placental natural killer cells, or combinations thereof. The potency of the placental perfusate, placental perfusate cells and/or PINK cells, or combinations or pools of the same, can be expressed, e.g., as the number of cells or volume of solution required to suppress tumor cell growth, e.g., by about 10%, 15%, 20%, 25%, 30%, 35%, 40%, 45%, 50%, or the like.

In certain embodiments, placental perfusate, placental perfusate cells, and PINK cells are provided as pharmaceutical grade administrable units. Such units can be provided in discrete volumes, e.g., 100 mL, 150 mL, 200 mL, 250 mL, 300 mL, 350 mL, 400 mL, 450 mL, 500 mL, or the like. Such units can be provided so as to contain a specified number of, e.g., placental perfusate cells, placental intermediate natural killer cells, or both, e.g., $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more cells per unit. Such units can be provided to contain specified numbers of any two, or all three, of placental perfusate, placental perfusate cells, and/or PINK cells.

In the above combinations of placental perfusate, placental perfusate cells and/or PINK cells, any one, any two, or all three of the placental perfusate, placental perfusate cells and/or PINK cells can be autologous to a recipient (that is, obtained from the recipient), or homologous to a recipient (that is, obtained from at last one other individual from said recipient).

Any of the above combinations or pools of PINK cells, placental perfusate cells and/or placental perfusate can comprise $CD56^+CD16^+$ natural killer cells from, e.g., placental perfusate, peripheral blood, umbilical cord blood, bone marrow, or the like. In specific embodiments, the combinations comprise about, at least about, or at most about $1\times10^4$, $5\times10^4$, $1\times10^5$, $5\times10^5$, $1\times10^6$, $5\times10^6$ or more such natural killer cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more cells per unit. The $CD56^+CD16^+$ natural killer cells can be used as isolated from a natural source, or can be expanded prior to inclusion in one of the above combinations or pools. The $CD56^+CD16^+$ NK cells can be autologous (that is, obtained from the same individual as the placental perfusate, placental perfusate cells and/or PINK cells; or obtained from a recipient) or homologous (that is, derived from an individual different from the placental perfusate, placental perfusate cells and/or PINK cells; or from an individual that is not recipient).

Preferably, each unit is labeled to specify volume, number of cells, type of cells, whether the unit has been enriched for a particular type of cell, and/or potency of a given number of cells in the unit, or a given number of milliliters of the unit, causes a measurable suppression of proliferation of a particular type or types of tumor cell.

Also provided herein are compositions comprising placental intermediate natural killer cells, alone or in combination with placental perfusate cells and/or placental perfusate. Thus, in another aspect, provided herein is a composition comprising isolated $CD56^+$, $CD16^-$ natural killer cells, wherein said natural killer cells are isolated from placental perfusate, and wherein said natural killer cells comprise at least 50% of cells in the composition. In a specific embodiment, said natural killer cells comprise at least 80% of cells in the composition. In another specific embodiment, said composition comprises isolated $CD56^+$, $CD16^+$ natural killer cells. In a more specific embodiment, said $CD56^+$, $CD16^+$ natural killer cells are from a different individual than said $CD56^+$, $CD16^-$ natural killer cells. In another specific embodiment, said natural killer cells are from a single individual. In a more specific embodiment, said isolated natural killer cells comprise natural killer cells from at least two different individuals. In another specific embodiment, the composition comprises isolated placental perfusate. In a more specific embodiment, said placental perfusate is from the same individual as said natural killer cells. In another more specific embodiment, said placental perfusate comprises placental perfusate from a different individual than said natural killer cells. In another specific embodiment, the composition comprises placental perfusate cells. In a more specific embodiment, said placental perfusate cells are from the same individual as said natural killer cells. In another more specific embodiment, said placental perfusate cells are from a different individual than said natural killer cells. In another specific embodiment, the composition additionally comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals.

5.5.2. Compositions Comprising Adherent Placental Stem Cells

In other embodiments, the placental perfusate, plurality of placental perfusate cells, and/or plurality of PINK cells, or a combination or pool of any of the foregoing, is supplemented with adherent placental stem cells. Such stem cells are described, e.g, in Hariri U.S. Pat. Nos. 7,045,148 and 7,255,879. Adherent placental stem cells are not trophoblasts.

The placental perfusate, plurality of placental perfusate cells, and/or plurality of PINK cells, or a combination or pool of any of the foregoing can be supplemented with, e.g., $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more adherent placental cells. The adherent placental stem cells in the combinations can be, e.g., adherent placental stem cells that have been cultured for, e.g., 1, 2, 3, 4, 5, 6, 7, 8, 9, 10, 12, 14, 16, 18, 20, 22, 24, 26, 28, 30, 32, 34, 36, 38, or 40 population doublings, or more.

Adherent placental stem cells, when cultured in primary cultures or in cell culture, adhere to the tissue culture substrate, e.g., tissue culture container surface (e.g., tissue culture plastic). Adherent placental stem cells in culture assume a generally fibroblastoid, stellate appearance, with a number of cytoplasmic processes extending from the central cell body. Adherent placental stem cells are, however, morphologically distinguishable from fibroblasts cultured under the same conditions, as the placental stem cells exhibit a greater number of such processes than do fibroblasts. Morphologically, placental stem cells are also distinguishable from hematopoietic stem cells, which generally assume a more rounded, or cobblestone, morphology in culture.

Adherent placental stem cells, and populations of placental stem cells, useful in the compositions and methods provided herein, express a plurality of markers that can be used to identify and/or isolate the stem cells, or populations of cells that comprise the stem cells. The adherent placental stem cells, and adherent stem cell populations useful in the compositions and methods provided herein include stem cells and stem cell-containing cell populations obtained directly from the placenta, or any part thereof (e.g., amnion, chorion, amnion-chorion plate, placental cotyledons, umbilical cord, and the like). The adherent placental stem cell population, in one embodiment, is a population (that is, two or more) of adherent placental stem cells in culture, e.g., a population in a container, e.g., a bag.

Adherent stem cells generally express the markers CD73, CD105, CD200, HLA-G, and/or OCT-4, and do not express CD34, CD38, or CD45. Adherent placental stem cells can also express HLA-ABC (MHC-1) and HLA-DR. These markers can be used to identify adherent placental stem cells, and to distinguish placental stem cells from other stem cell types. Because the placental stem cells can express CD73 and CD105, they can have mesenchymal stem cell-like characteristics. However, because the adherent placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the adherent placental stem cells as non-hematopoietic stem cells.

In one embodiment, the adherent placental stem cells are $CD200^+$, $HLA-G^+$, wherein the stem cells detectably suppress cancer cell proliferation or tumor growth. In a specific embodiment, said adherent stem cells are also $CD73^+$ and $CD105^+$. In another specific embodiment, said adherent stem cells are also $CD34^-$, $CD38^-$ or $CD45^-$. In a more specific embodiment, said adherent stem cells are also $CD34^-$, $CD38^-$, $CD45^-$, $CD73^+$ and $CD105^+$. In another embodiment, said adherent stem cells produce one or more embryoid-like bodies when cultured under conditions that allow the formation of embryoid-like bodies.

In another embodiment, the adherent placental stem cells are $CD73^+$, $CD105^+$, $CD200^+$, wherein said stem cells detectably suppress cancer cell proliferation or tumor growth. In a specific embodiment of said populations, said adherent stem cells are $HLA-G^+$. In another specific embodiment, said adherent stem cells are $CD34^-$, $CD38^-$ or $CD45^-$. In another specific embodiment, said adherent stem cells are $CD34^-$, $CD38^-$ and $CD45^-$. In a more specific embodiment, said adherent stem cells are $CD34^-$, $CD38^-$, $CD45^-$, and $HLA-G^+$. In another specific embodiment, said adherent placental stem cells produce one or more embryoid-like bodies when cultured under conditions that allow the formation of embryoid-like bodies.

In another embodiment, the adherent placental stem cells are $CD200^+$, $OCT-4^+$, wherein said stem cells detectably suppress cancer cell proliferation or tumor growth. In a specific embodiment, said adherent stem cells are $CD73^+$ and $CD105^+$. In another specific embodiment, said adherent stem cells are $HLA-G^+$. In another specific embodiment, said adherent stem cells are $CD34^-$, $CD38^-$ and $CD45^-$. In a more specific embodiment, said adherent stem cells are $CD34^-$, $CD38^-$, $CD45^-$, $CD73^+$, $CD105^+$ and $HLA-G^+$. In another specific embodiment, the adherent placental stem cells produce one or more embryoid-like bodies when cultured under conditions that allow the formation of embryoid-like bodies.

In another embodiment, the adherent placental stem cells are $CD73^+$, $CD105^+$ and $HLA-G^+$, wherein said adherent stem cells detectably suppress cancer cell proliferation or tumor growth. In a specific embodiment of the above plurality, said adherent stem cells are also $CD34^-$, $CD38^-$ or $CD45^-$. In another specific embodiment, said adherent stem cells are also $CD34^-$, $CD38^-$ and $CD45^-$. In another specific embodiment, said adherent stem cells are also $OCT-4^+$. In another specific embodiment, said adherent stem cells are also $CD200^+$. In a more specific embodiment, said adherent stem cells are also $CD34^-$, $CD38^-$, $CD45^-$, $OCT-4^+$ and $CD200^+$.

In another embodiment, the adherent placental stem cells are $CD73^+$, $CD105^+$ stem cells, wherein said stem cells produce one or more embryoid-like bodies under conditions that allow formation of embryoid-like bodies, and wherein said adherent stem cells detectably suppress cancer cell proliferation or tumor growth. In a specific embodiment, said adherent stem cells are also $CD34^-$, $CD38^-$ or $CD45^-$. In another specific embodiment, said adherent stem cells are also $CD34^-$, $CD38^-$ and $CD45^-$. In another specific embodiment, said adherent stem cells are also $OCT-4^+$. In a more specific embodiment, said adherent stem cells are also $OCT-4^+$, $CD34^-$, $CD38^-$ and $CD45^-$.

In another embodiment, the adherent placental stem cells are $OCT-4^+$ stem cells, wherein said adherent placental stem cells produce one or more embryoid-like bodies when cultured under conditions that allow the formation of embryoid-like bodies, and wherein said stem cells have been identified as detectably suppressing cancer cell proliferation or tumor growth.

In various embodiments, at least 10%, at least 20%, at least 30%, at least 40%, at least 50% at least 60%, at least 70%, at least 80%, at least 90%, or at least 95% of said isolated placental cells are $OCT4^+$ stem cells. In a specific embodiment of the above populations, said stem cells are $CD73^+$ and $CD105^+$. In another specific embodiment, said stem cells are $CD34^-$, $CD38^-$, or $CD45^-$. In another specific embodiment, said stem cells are $CD200^+$. In a more specific embodiment, said stem cells are $CD73^+$, $CD105^+$, $CD200^+$, $CD34^-$, $CD38^-$, and $CD45^-$. In another specific embodiment, said population has been expanded, for example, passaged at least once, at least three times, at least five times, at least 10 times, at least 15 times, or at least 20 times.

In a more specific embodiment of any of the above embodiments, the adherent placental cells express ABC-p (a placenta-specific ABC transporter protein; see, e.g., Allikmets et al., *Cancer Res.* 58(23):5337-9 (1998)).

In another embodiment, the adherent placental stem cells are $CD29^+$, $CD44^+$, $CD73^+$, $CD90^+$, $CD105^+$, $CD200^+$, $CD34^-$ and $CD133^-$. In another embodiment, the adherent placental stem cells, the placental stem cells constitutively secrete IL-6, IL-8 and monocyte chemoattractant protein (MCP-1).

Each of the above-referenced placental stein cells can comprise placental stem cells obtained and isolated directly from a mammalian placenta, or placental stem cells that have been cultured and passaged at least 1, 2, 3, 4, 5, 6, 7, 8, 9, 10, 12, 14, 16, 18, 20, 25, 30 or more times, or a combination thereof. Tumor cell suppressive pluralities of the adherent placental stem cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{19}$, $5\times10^{19}$, $1\times10^{11}$ or more adherent placental stem cells.

5.5.3. Compositions Comprising Placental Stem Cell Conditioned Media

Also provided herein is the use of a tumor-suppressive composition comprising PINK cells, placental perfusate and/or placental perfusate, and additionally conditioned medium. Adherent placental stem cells, placental perfusate cells and/or placental intermediate natural killer cells can be used to produce conditioned medium that is tumor cell suppressive, that is, medium comprising one or more biomolecules secreted or excreted by the stem cells that have a detectable tumor cell suppressive effect on a plurality of one or more types of immune cells. In various embodiments, the conditioned medium comprises medium in which placental cells (e.g., stein cells, placental perfusate cells, PINK cells) have grown for at least 1, 2, 3, 4, 5, 6, 7, 8, 9, 10, 11, 12, 13, 14 or more days. In other embodiments, the conditioned medium comprises medium in which placental cells have grown to at least 30%, 40%, 50%, 60%, 70%, 80%, 90% confluence, or up to 100% confluence. Such conditioned medium can be used to support the culture of a separate population of placental cells, or cells of another kind. In another embodiment, the conditioned medium provided herein comprises medium in which adherent placental stem cells and non-placental stem cells have been cultured.

Such conditioned medium can be combined with any of, or any combination of, placental perfusate, placental perfusate cells, and/or placental intermediate natural killer cells to form a tumor cell suppressive composition. In certain embodiments, the composition comprises less than half conditioned medium by volume, e.g., about, or less than about, 50%, 45%, 40%, 35%, 30%, 25%, 20%, 15%, 10%, 5%, 4%, 3%, 2%, or 1% by volume.

Thus, in one embodiment, provided herein is a composition comprising culture medium from a culture of placental stem cells, wherein said placental stem cells (a) adhere to a substrate; (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies; and (c) detectably suppress the growth or proliferation of a tumor cell or population of tumor cells. In a specific embodiment, the composition further comprises a plurality of said placental stem cells. In another specific embodiment, the composition comprises a plurality of non-placental cells. In a more specific embodiment, said non-placental cells comprise CD34+ cells, e.g., hematopoietic progenitor cells, such as peripheral blood hematopoietic progenitor cells, cord blood hematopoietic progenitor cells, or placental blood hematopoietic progenitor cells. The non-placental cells can also comprise other stem cells, such as mesenchymal stem cells, e.g., bone marrow-derived mesenchymal stem cells. The non-placental cells can also be one ore more types of adult cells or cell lines. In another specific embodiment, the composition comprises an anti-proliferative agent, e.g., an anti-MIP-1α or anti-MIP-1β antibody.

In a specific embodiment, placental cell-conditioned culture medium or supernatant is obtained from a plurality of placental stem cells co-cultured with a plurality of tumor cells at a ratio of about 1:1, about 2:1, about 3:1, about 4:1, or about 5:1 placental stem cells to tumor cells. For example, the conditioned culture medium or supernatant can be obtained from a culture comprising about $1\times10^5$ placental stem cells, about $1\times10^6$ placental stem cells, about $1\times10^7$ placental stem cells, or about $1\times10^8$ placental stem cells, or more. In another specific embodiment, the conditioned culture medium or supernatant is obtained from a co-culture comprising about $1\times10^5$ to about $5\times10^5$ placental stein cells and about $1\times10^5$ tumor cells; about $1\times10^6$ to about $5\times10^6$ placental stem cells and about $1\times10^6$ tumor cells; about $1\times10^7$ to about $5\times10^7$ placental stem cells and about $1\times10^7$ tumor cells; or about $1\times10^8$ to about $5\times10^8$ placental stem cells and about $1\times10^8$ tumor cells.

In a specific embodiment, the conditioned medium suitable for administration to a 70 kg individual comprises supernatant conditioned by about 70 million placental stem cells in about 200 mL culture medium.

Conditioned medium can be condensed to prepare an administrable pharmaceutical-grade product. For example, conditioned medium can be condensed to about 90%, 80%, 70%, 60%, 50%, 40%, 30%, 20%, 10% or more by removal of water, e.g., by evaporation, lyophilization, or the like. In a specific embodiment, for example, 200 mL conditioned medium from about 70 million placental stem cells can be condensed to a volume of about 180 mL, 160 mL, 140 mL, 120 mL, 100 mL, 80 mL, 60 mL, 40 mL, 20 mL or less. The conditioned medium can also be substantially dried, e.g., to a powder, e.g., by evaporation, lyophilization or the like.

5.6. Preservation of Perfusate and Placental Cells

Placental perfusate or placental cells, e.g., perfusate cells, combined natural killer cells, and PINK cells, can be preserved, that is, placed under conditions that allow for long-term storage, or under conditions that inhibit cell death by, e.g., apoptosis or necrosis.

Placental perfusate can be produced by passage of a placental cell composition through at least a part of the placenta, e.g., through the placental vasculature. The placental cell collection composition comprises one or more compounds that act to preserve the cells contained within the perfusate. Such a placental cell collection composition is described in Section 5.1, above, e.g., a composition comprising an apoptosis inhibitor, necrosis inhibitor and/or an oxygen-carrying perfluorocarbon, as described in related U.S. application Ser. No. 11/648,812, entitled "Improved Composition for Collecting and Preserving Placental Stem Cells and Methods of Using the Composition" filed on Dec. 28, 2006, In one embodiment, the placental cell collection composition, passed through the placenta or placental tissue, is the placental perfusate useful in the methods described in Section 5.4, below.

In one embodiment, placental perfusate and/or placental cells are collected from a mammalian, e.g., human, post-partum placenta by contacting the cells with a placental cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. For example, the placenta can be perfused with the placental cell collection composition, and placental cells, e.g., total nucleated placental cells, are isolated therefrom. In a specific embodiment, the inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another embodiment, the placental cell collection composition comprises said inhibitor of apoptosis and said oxygen-carrying perfluorocarbon in separate phases. In another embodiment, the placental cell collection composition comprises said inhibitor of apoptosis and said oxygen-carrying perfluorocarbon in an emulsion. In another embodiment, the placental cell collection composition additionally comprises an emulsifier, e.g., lecithin. In another embodiment, said apoptosis inhibitor and said perfluorocarbon are between about 0° C. and about 25° C. at the time of contacting the placental cells. In another more specific embodiment, said apoptosis inhibitor and said perfluorocarbon are between about 2° C. and 10° C., or between about 2° C. and about 5° C., at the time of contacting the placental cells. In another more specific embodiment, said contacting is performed during transport of said population of stem cells. In another more specific embodiment, said contacting is performed during freezing and thawing of said population of stem cells.

In another embodiment, placental perfusate and/or placental cells can be collected and preserved by contacting the perfusate and/or cells with an inhibitor of apoptosis and an organ-preserving compound, wherein said inhibitor of apoptosis is present in an amount and for a time sufficient to reduce or prevent apoptosis of the cells, as compared to perfusate or placental cells not contacted with the inhibitor of apoptosis.

In a specific embodiment, the organ-preserving compound is UW solution (described in U.S. Pat. No. 4,798,824; also known as VIASPAN™; see also Southard et al., *Transplantation* 49(2):251-257 (1990) or a solution described in Stern et al., U.S. Pat. No. 5,552,267. In another embodiment, said organ-preserving composition is hydroxyethyl starch, lactobionic acid, raffinose, or a combination thereof. In another embodiment, the placental cell collection composition additionally comprises an oxygen-carrying perfluorocarbon, either in two phases or as an emulsion.

In another embodiment of the method, placental perfusate and/or placental cells are contacted with a placental cell collection composition comprising an apoptosis inhibitor and oxygen-carrying perfluorocarbon, organ-preserving compound, or combination thereof, during perfusion. In another embodiment, placental cells are contacted with said stem cell collection compound after collection by perfusion.

Typically, during placental cell collection, enrichment and isolation, it is preferable to minimize or eliminate cell stress due to hypoxia and mechanical stress. In another embodiment of the method, therefore, placental perfusate, a placental cell, or population of placental cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of placental cells is exposed to said hypoxic condition for less than two hours during said preservation. In another more specific embodiment, said population of placental cells is exposed to said hypoxic condition for less than one hour, or less than thirty minutes, or is not exposed to a hypoxic condition, during collection, enrichment or isolation. In another specific embodiment, said population of placental cells is not exposed to shear stress during collection, enrichment or isolation.

The placental cells provided herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. Placental cells are preferably cooled at about 1° C./min during cryopreservation. A preferred cryopreservation temperature is about −80° C. to about −180° C., preferably about −125° C. to about −140° C. Cryopreserved placental cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.7. Use of Placental Perfusate, PINK Cells, and Combined Placental Natural Killer Cells to Suppress Tumor Cell Growth Also provided herein are methods of suppressing the growth, e.g., proliferation, of tumor cells using placental perfusate, cells isolated from placental perfusate, isolated combined natural killer cells, or isolated placental natural killer cells, e.g., placenta-derived intermediate natural killer cells.

In one embodiment, provided herein is a method of suppressing the proliferation of a tumor cell, or plurality of tumor cells, comprising contacting the tumor cell or plurality of tumor cells with placental perfusate, placental perfusate cells, isolated combined natural killer cells, and/or PINK cells, such that the proliferation of the tumor cell or plurality of tumor cells is detectably reduced compared to a tumor cell or plurality of tumor cells of the same type not contacted with the placental perfusate, perfusate cells, isolated combined natural killer cells, and/or PINK cells.

As used herein, "contacting," in one embodiment, encompasses direct physical, e.g., cell-cell, contact between placental perfusate, placental perfusate cells, placental natural killer cells, e.g., placental intermediate natural killer cells, and/or isolated combined natural killer cells; and a tumor cell or plurality of tumor cells. In another embodiment, "contacting" encompasses presence in the same physical space, e.g., placental perfusate, placental perfusate cells, placental natural killer cells, e.g., placental intermediate natural killer cells, and/or isolated combined natural killer cells are placed in the same container e.g., culture dish, multiwell place) as a tumor cell or plurality of tumor cells. In another embodiment, "contacting" placental perfusate, placental perfusate cells, combined natural killer cells or placental intermediate natural killer cells, and a tumor cell or plurality of tumor cells is accomplished, e.g., by injecting or infusing the placental perfusate or cells, e.g., placental perfusate cells, combined natural killer cells or placental intermediate natural killer cells into an individual, e.g., a human comprising a tumor cell or plurality of tumor cells, e.g., a cancer patient.

In certain embodiments, placental perfusate is used in any amount that results in a detectable therapeutic benefit to an individual comprising a tumor cell or plurality of tumor cells, e.g., a cancer patient. In certain other embodiments, placental perfusate cells, placental intermediate natural killer cells, and/or combined natural killer cells are used in any amount that results in a detectable therapeutic benefit to an individual comprising a tumor cell or plurality of tumor cells. Thus, in another embodiment, provided herein is a method of suppressing the proliferation of a tumor cell, or plurality of tumor cells, comprising contacting the tumor cell or plurality of tumor cells with placental perfusate, placental perfusate cells and/or a placenta-derived intermediate natural killer cell, or plurality of PINK cells, within an individual such that said contacting is detectably or demonstrably therapeutically beneficial to said individual.

As used herein, "therapeutic benefits" include, but are not limited to, e.g., reduction in the size of a tumor; lessening or cessation of expansion of a tumor; reduction in the number of cancer cells in a tissue sample, e.g., a blood sample, per unit volume; the clinical improvement in any symptom of the particular cancer said individual has, the lessening or cessation of worsening of any symptom of the particular cancer the individual has, etc. Contacting of placental perfusate, placental perfusate cells and/or PINK cells that accomplishes any one or more of such therapeutic benefits is said to be therapeutically beneficial.

In certain embodiments, placental perfusate cells, e.g., nucleated cells from placental perfusate, combined natural killer cells, and/or placental intermediate natural killer cells are used in any amount or number that results in a detectable therapeutic benefit to an individual comprising a tumor cell or plurality of tumor cells, e.g., a cancer patient. Placental perfusate cells, combined natural killer cells and/or placental natural killer cells, e.g., placental intermediate natural killer cells can be administered to such an individual by numbers of cells, e.g., said individual can be administered at about, at least about, or at most about, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, or $5\times10^{10}$ placental perfusate cells, combined natural killer cells and/or natural killer cells. In other embodiments, placental perfusate cells, combined natural killer cells, and/or placenta-derived intermediate natural killer cells can be administered to such an individual by numbers of cells, e.g., said individual can be administered at about, at least about, or at most about, $1\times10^5$, $5\times10^5$, $1\times10^6$, $5\times10^6$, $1\times10^7$, $5\times10^7$, $1\times10^8$, $5\times10^8$, $1\times10^9$ $5\times10^9$, $1\times10^{10}$, or $5\times10^{10}$ placental perfusate cells, combined natural killer cells, and/or natural killer cells per kilogram of the individual. Placental perfusate cells and/or placenta-derived intermediate natural killer cells can be administered to such an individual according to an approximate ratio between placental perfusate cells and/or placental natural killer cells, e.g., placental intermediate natural killer cells, and tumor cells in said individual. For example, placental perfusate cells and/or placental natural killer cells, e.g., placental intermediate natural killer cells, can be administered to said individual in a ratio of about, at least about or at most about 1:1, 1:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1 to the number of tumor cells in the individual. The number of tumor cells in such an individual can be estimated, e.g., by counting the number of tumor cells in a sample of tissue from the individual, e.g., blood sample, biopsy, or the like. In specific embodiments, e.g., for solid tumors, said counting is performed in combination with imaging of the tumor or tumors to obtain an approximate tumor volume.

Further provided herein is a method for the suppression of the proliferation of a tumor cell or plurality of tumor cells using combinations of placental perfusate, placental perfusate cells, combined natural killer cells, and/or placenta-derived intermediate natural killer cells. In various embodiments, provided herein is a method of suppressing the proliferation of a tumor cell or plurality of tumor cells comprising contacting said tumor cell or tumor cells with placental perfusate supplemented with a plurality of placental perfusate cells or PINK cells; placental perfusate cells supplemented with placental perfusate or a plurality of PINK cells; PINK cells supplemented with placental perfusate and placental perfusate cells a plurality of PINK cells and a plurality of combined natural killer cells; a plurality of combined natural killer cells and a plurality of placental perfusate cells; placental perfusate supplemented with combined natural killer cells; or a combination of all of placental perfusate, placental perfusate cells, combined natural killer cells, and PINK cells.

In one specific embodiment, for example, the proliferation of a tumor cell or plurality of tumor cells is suppressed by placental perfusate supplemented with a plurality of placental perfusate cells, combined natural killer cells and/or a plurality of placental intermediate natural killer cells. In specific embodiments, for example, each milliliter of placental perfusate is supplemented with about $1\times10^4$, $5\times10^4$, $1\times10^5$, $5\times10^5$, $1\times10^6$, $5\times10^6$ or more placental perfusate cells or placental intermediate natural killer cells. In other specific embodiments, placental perfusate, e.g., one unit (i.e., the collection from a single placenta), or about 100, 150, 200, 250, 300, 350, 400, 450, 500, 550, 600, 650, 700, 750, 800, 850, 900, 950 or 1000 mL of perfusate, is supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more PINK cells, combined natural killer cells, and/or placental perfusate cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more PINK cells, combined natural killer cells, and/or placental perfusate cells.

In another specific embodiment, the proliferation of a tumor cell or plurality of tumor cells is suppressed by a plurality of placental perfusate cells supplemented with placental perfusate, combined natural killer cells, and/or placental intermediate natural killer cells. In more specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental perfusate cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental perfusate cells, are supplemented with about, or at least about, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more PINK cells and/or combined natural killer cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more PINK cells. In other more specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental perfusate cells, PINK cells, and/or combined natural killer cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$ $1\times10^{10}$, $5\times10^{10}$, $1\times10^{11}$ or more placental perfusate cells, are supplemented with about, or at least about, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mL of perfusate, or about 1 unit of perfusate.

In another specific embodiment, the proliferation of a tumor cell or plurality of tumor cells is suppressed by a plurality of placental intermediate natural killer cells supplemented by placental perfusate, placental perfusate cells, and/or combined natural killer cells. In more specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental intermediate natural killer cells, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more PINK cells, are supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental perfusate cells and/or combined natural killer cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$ $5\times10^9$, $1\times10^{10}$, $5\times10^{10}$, $1\times10^{11}$ or more placental perfusate cells and/or combined natural killer cells. In other more specific embodiments, about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more placental perfusate cells and/or combined natural killer cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental intermediate natural killer cells and/or combined natural killer cells are supplemented with about, or at least about, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mL of perfusate, or about 1 unit of perfusate.

In another embodiment, the proliferation of a tumor cell or plurality of tumor cells is suppressed by contacting the tumor cell or tumor cells with placental perfusate, perfusate cells, PINK cells, and/or combined natural killer cells supplemented with adherent placental stem cells. In specific embodiments, the placental perfusate, perfusate cells, or PINK cells are supplemented with about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more adherent placental stem cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more adherent placental stem cells.

In another embodiment, the proliferation of a tumor cell or plurality of tumor cells is suppressed by contacting the tumor cell or tumor cells with placental perfusate, perfusate cells, combined natural killer cells, and/or PINK cells supplemented with adherent placental stem cell-conditioned medium, e.g., 0.1, 0.2, 0.3, 0.4, 0.5, 0.6, 0.1, 0.8, 0.9, 1, 2, 3, 4, 5, 6, 7, 8, 9, 10 mL of stem cell-conditioned culture medium per unit of perfusate, perfusate cells, combined natural killer cells, and/or PINK cells, or per $10^4$, $10^5$, $10^6$, $10^7$, $10^8$, $10^9$ or $10^{10}$ cells.

In other embodiments, the placental perfusate, placental perfusate cells, placental natural killer cells, e.g., PINK cells, combined natural killer cells, and combinations and pools comprising the same, are used as initially obtained, that is, perfusate as obtained during perfusion, placental perfusate cells as isolated from such perfusate, combined natural killer cells from such perfusate and matched umbilical cord blood, or PINK cells isolated from such perfusate or such placental perfusate cells. In other embodiments, the placental perfusate, placental perfusate cells, PINK cells, and combinations and pools of the same are processed prior to use. For example, placental perfusate can be used in its raw, unprocessed form as collected from the placenta. Placental perfusate can also be processed prior to use, e.g., by the negative selection of one or more types of cells, reduction in volume by dehydration; lyophilization and rehydration, etc. Similarly, populations of perfusate cells can be used as initially isolated from placental perfusate, e.g., as total nucleated cells from placental perfusate, or can be processed, e.g., to remove one or more cell types (e.g., erythrocytes). PINK cells can be used as initially isolated from placental perfusate, e.g., using CD56 microbeads, or can be processed, e.g., to remove one or more non-killer cell types.

In another embodiment, provided herein is a method of suppressing the proliferation of a tumor cell or tumor cells, comprising contacting the tumor cell or tumor cells with placental perfusate, placental perfusate cells, PINK cells, combined natural killer cells, or pools or combinations comprising the same, wherein said placental perfusate, placental perfusate cells, PINK cells, combined natural killer cells, or pools or combinations comprising the same have been contacted with interleukin-2 (IL-2) for a period of time prior to said contacting. In certain embodiments, said period of time is about, at least, or at most 1, 2, 3, 4, 5, 6, 7, 8, 9, 10, 12, 14, 16, 18, 20, 22, 24, 26, 28, 30, 32, 34, 36, 38, 40, 42, 44, 46 or 48 prior to said contacting.

The perfusate, perfusate cells, PINK cells, combined natural killer cells, or pools and/or combinations of the same can be administered once to an individual having cancer, or an individual having tumor cells during a course of anticancer therapy, or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy. The perfusate, perfusate cells, PINK cells, pools and/or combinations of the same can be administered without regard to whether the perfusate, perfusate cells, PINK cells, pools and/or combinations of the same have been administered to a person having cancer, or having tumor cells, in the past. Thus, the methods provided herein encompasses the administration to a person having cancer or having tumor cells any combination of placental perfusate, perfusate cells, PINK cells, pools and/or combinations comprising the same.

In a specific embodiment, the tumor cells are blood cancer cells. In various specific embodiments, the tumor cells are primary ductal carcinoma cells, leukemia cells, acute T cell leukemia cells, chronic myeloid lymphoma (CML) cells, acute myelogenous leukemia cells, chronic myelogenous leukemia (CML) cells, lung carcinoma cells, colon adenocarcinoma cells, histiocytic lymphoma cells, multiple myeloma cell, retinoblastoma cells, colorectal carcinoma cells or colorectal adenocarcinoma cells.

The placental perfusate, perfusate cells, PINK cells, combined natural killer cells, pools, and/or combinations comprising the same can be part of an anticancer therapy regimen that includes one or more other anticancer agents. Such anticancer agents are well-known in the art. Specific anticancer agents that may be administered to an individual having cancer, in addition to the perfusate, perfusate cells, PINK cells, pools and/or combinations of the same, include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomycin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth faetor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridinc; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

5.8. Treatment of Natural Killer Cells With Immunomodulatory Compounds

Isolated natural killer cells, e.g., PINK cells or combined natural killer cells, as described elsewhere herein, can be treated with an immunomodulatory compound, e.g., contacted with an immunomodulatory compound, to enhance the antitumor activity of the cell. Thus, provided herein is a method of increasing the cytotoxicity of a natural killer cell to a tumor cell comprising contacting the natural killer cell with an immunomodulatory compound for a time and in a concentration sufficient for the natural killer cell to demonstrate increased cytotoxicity towards a tumor cell compared to a natural killer cell not contacted with the immunomodulatory compound. In another embodiment, provided herein is a method of increasing the expression of granzyme B in a natural killer cell comprising contacting the natural killer cell with an immunomodulatory compound for a time and in a concentration sufficient for the natural killer cell to demonstrate increased expression of granzyme B compared to a natural killer cell not contacted with the immunomodulatory compound. The immunomodulatory compound can be any compound described below, e.g., lenalidomide or pomalidomide.

Also provided herein is a method of increasing the cyclotoxicity of a population of natural killer cells, e.g., PINK cells or combined natural killer cells, to a plurality of tumor cells comprising contacting the population of natural killer cells with an immunomodulatory compound for a time and in a concentration sufficient for the population of natural killer cells to demonstrate detectably increased cytotoxicity towards said plurality of tumor cells compared to an equivalent number of natural killer cells not contacted with the immunomodulatory compound. In another embodiment, provided herein is a method of increasing the expression of granzyme B in a population of natural killer cells comprising contacting the population of natural killer cells with an immunomodulatory compound for a time and in a concentration sufficient for the population of natural killer cells to express a detectably increased amount of granzyme B compared to an equivalent number of natural killer cells not contacted with the immunomodulatory compound. In a specific embodiment, said population of natural killer cells is contained within placental perfusate cells, e.g., total nucleated cells from placental perfusate.

In specific embodiments of the above embodiments, the natural killer cells are CD56$^+$, CD16$^-$ placental intermediate natural killer cells (PINK cells). In another specific embodiment of the above embodiments, the natural killer cells are combined natural killer cells, i.e., natural killer cells from matched placental perfusate and umbilical cord blood.

In another specific embodiment, said plurality of natural killer cells, e.g., PINK cells or combined natural killer cells, contacted with said immunomodulatory compound express one or more of BAX, CCL5, CCR5, CSF2, FAS, GUSB, IL2RA, or TNFRSF18 at a higher level than an equivalent number of said natural killer cells not contacted with said immunomodulatory compound. In another specific embodiment, said plurality of natural killer cells, e.g., PINK cells, contacted with said immunomodulatory compound express one or more of ACTB, BAX, CCL2, CCL3, CCL5, CCR5, CSF1, CSF2, ECE1, FAS, GNLY, GUSB, GZMB, IL1A. IL2RA, IL8, IL10, LTA, PRF1, PTGS2, SKI, and TBX21 at a higher level than an equivalent number of said natural killer cells not contacted with said immunomodulatory compound.

Also provided herein is a method of increasing the cyclotoxicity of a population of human placental perfusate cells, e.g., total nucleated cells from placental perfusate, towards a plurality of tumor cells, comprising contacting the placental perfusate cells with an immunomodulatory compound for a time and in a concentration sufficient for the placental perfusate cells to demonstrate detectably increased cytotoxicity towards said plurality of tumor cells compared to an equivalent number of placental perfusate cells not contacted with the immunomodulatory compound. In another embodiment, provided herein is a method of increasing the expression of granzyme B in a population of placental perfusate cells comprising contacting the population of placental perfusate cells with an immunomodulatory compound for a time and in a concentration sufficient for the population of placental perfusate cells to express a detectably increased amount of granzyme B compared to an equivalent number of placental perfusate cells not contacted with the immunomodulatory compound.

Immunomodulatory compounds can either be commercially purchased or prepared according to the methods described in the patents or patent publications referred to herein, all of which are incorporated by reference. Further, optically pure compositions can be asymmetrically synthesized or resolved using known resolving agents or chiral columns as well as other standard synthetic organic chemistry techniques. Immunomodulatory compounds may be racemic, stereomerically enriched or stereomerically pure, and may encompass pharmaceutically acceptable salts, solvates, and prodrugs thereof.

As used herein and unless otherwise indicated, the terms "immunomodulatory compounds" encompass small organic molecules that markedly inhibit TNF-α, LPS induced monocyte IL-1β and IL-12, and partially inhibit IL-6 production. In specific examples, the immunomodulatory compounds are lenalidomide, pomalidomide or thalidomide.

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874, 448 and 5,955,476; the tetra substituted 2-(2,6-dioxopiperidin-3-yl)-1-oxoisoindolines described in U.S. Pat. No. 5,798, 368; 1-oxo and 1,3-dioxo-2-(2,6-dioxopiperidin-3-yl) isoindolines (e.g., 4-methyl derivatives of thalidomide), including, but not limited to, those disclosed in U.S. Pat. Nos. 5,635,517, 6,476,052, 6,555,554, and 6,403,613; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380, 239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; and isoindole-imide compounds such as those described in U.S. patent publication no. 2003/0045552 A1, U.S. Pat. No. 7,091,353, and WO 02/059106. The entireties of each of the patents and patent applications identified herein are incorporated herein by reference. Immunomodulatory compounds do not include thalidomide.

In certain embodiments, the immunomodulatory compounds are 1-oxo- and 1,3 dioxo-2-(2,6-dioxopiperidin-3-yl) isoindolines substituted with amino in the benzo ring as described in U.S. Pat. No. 5,635,517, which is incorporated herein by reference in its entirety. These compounds have the structure I:

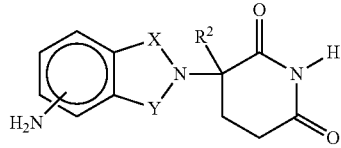

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline; and
1,3-dioxo-2-(2,6-dioxopiperidin-3-yl)-5-aminoisoindoline.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and WO 98/03502, each of which is incorporated herein by reference.

Representative compounds are of formula:
in which:

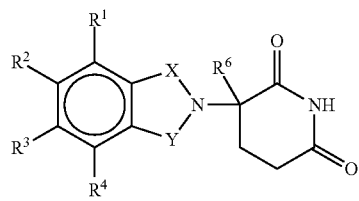

one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzyl, or halo;

provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

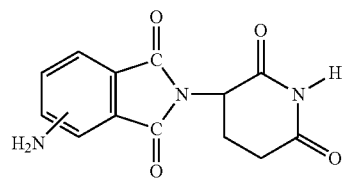

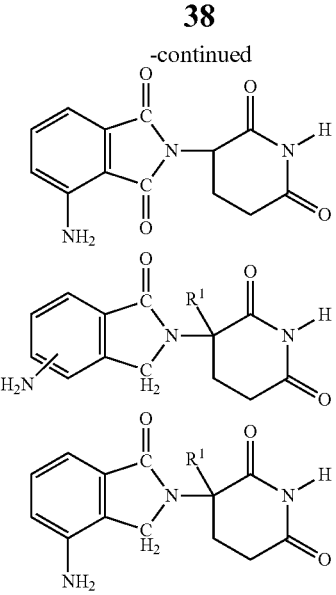

wherein R$^1$ is hydrogen or methyl. In a separate embodiment, encompassed is the use of enantiomerically pure forms (e.g. optically pure (R) or (S) enantiomers) of these compounds.

Still other specific immunomodulatory compounds belong to a class of isoindole-imides disclosed in U.S. Patent Application Publication Nos. US 2003/0096841 and US 2003/0045552, and WO 02/059106, each of which are incorporated herein by reference. Representative compounds are of formula II:

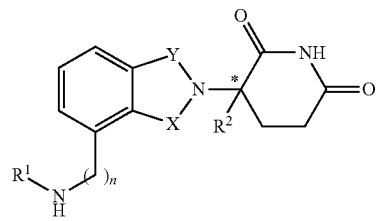

and pharmaceutically acceptable salts, hydrates, solvates, clathrates, enantiomers, diastereomers, racemates, and mixtures of stereoisomers thereof, wherein:

one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to faun a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)_2$; $(C_0-C_8)$alkyl-NH—C(O)O—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

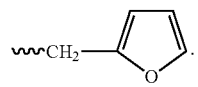

In another embodiment of the compounds of formula II, $R^1$ is

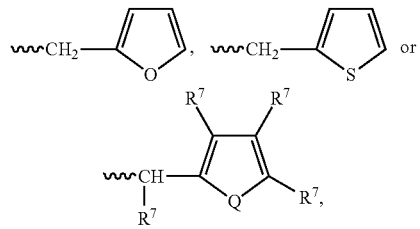

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds belong to a class of isoindole-imides disclosed in U.S. Patent Application Publication No. 2002/0045643, International Publication No. WO 98/54170, and U.S. Pat. No. 6,395,754, each of which is incorporated herein by reference. Representative compounds are of formula III:

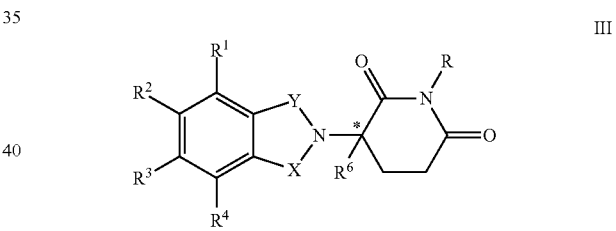

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1, R^2, R^3$, or $R^4$, independently of the others, is halo, alkyl of 1 to 4 carbon atoms, or alkoxy of 1 to 4 carbon atoms or (ii) one of $R^1, R^2, R^3$, or $R^4$ is nitro or —$NHR^5$ and the remaining of $R^2, R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

$R^1$ is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center.

Other representative compounds are of formula:

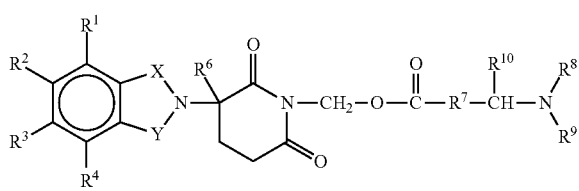

wherein:

one of X and Y is C=O and the other of X and Y is C=O or CH$_2$;

(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzo, chloro, or fluoro;

R$^7$ is m-phenylene or p-phenylene or —(C$_n$H$_{2n}$)— in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S—, or —NH—;

R$^{10}$ is hydrogen, alkyl of to 8 carbon atoms, or phenyl.

Other representative compounds are of formula:

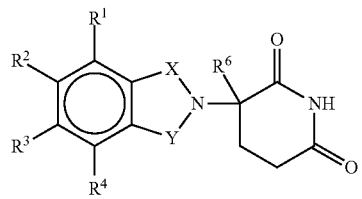

in which one of X and Y is C=O and the other of X and Y is C=O or CH$_2$;

each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and R$^6$ is hydrogen, alkyl of 1 to 8 carbon atoms, benzo, chloro, or fluoro.

Other representative compounds are of formula:

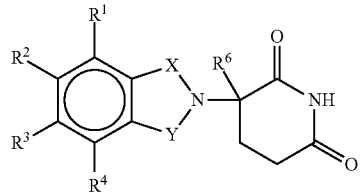

in which:

one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and R$^6$ is alkyl of 1 to 8 carbon atoms, benzo, chloro, or fluoro.

Specific examples of the compounds are of formula:

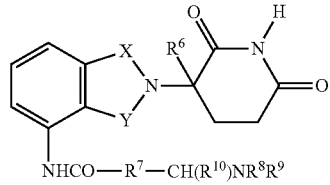

in which:

one of X and Y is C=O and the other of X and Y is C=O or CH$_2$;

R$^6$ is hydrogen, alkyl of 1 to 8 carbon atoms, benzyl, chloro, or fluoro;

R$^7$ is m-phenylene, p-phenylene or —(C$_n$H$_{2n}$)— in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and R$^{10}$ is hydrogen, alkyl of 1 to 8 carbon atoms, or phenyl.

The most preferred immunomodulatory compounds are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

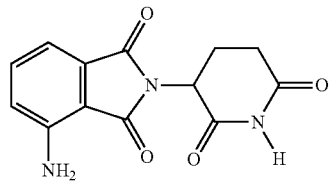 [SMILES: Nc1cccc2c1C(=O)N(C1CCC(=O)NC1=O)C2=O]

The compound 3-(4-amino-1-oxo-1,3-dihydro-isoindol-2-yl)-piperidine-2,6-dione has the following chemical structure:

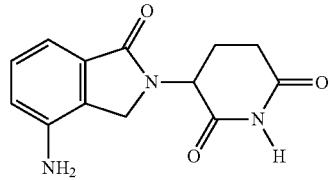 [SMILES: Nc1cccc2c1CN(C1CCC(=O)NC1=O)C2=O]

In another embodiment, specific immunomodulatory compounds encompass polymorphic forms of 3-(4-amino-1-oxo-1,3 dihydro-isoindol-2-yl)-piperidene-2,6-dione such as Form A, B, C, D, E, F, G and H, disclosed in U.S. publication no. US 2005/0096351 A1, which is incorporated herein by reference. For example, Form A of 3-(4-amino-1-oxo-1,3 dihydro-isoindol-2-yl)-piperidene-2,6-dione is an unsolvated, crystalline material that can be obtained from nonaqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds usable in the methods provided herein include, but are not limited to, 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

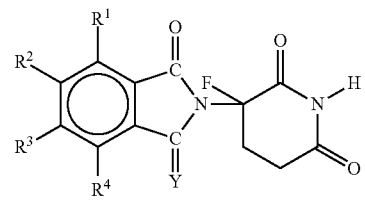

wherein Y is oxygen or $H^2$ and
each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds usable in the methods provided herein include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

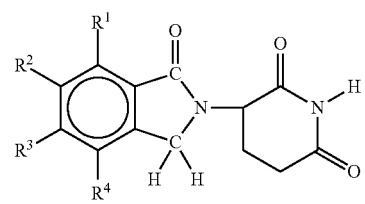

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds that can be used in the methods provided herein include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

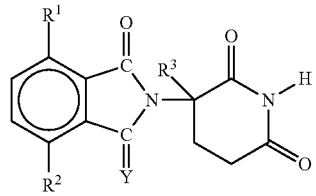

in which
Y is oxygen or $H_2$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

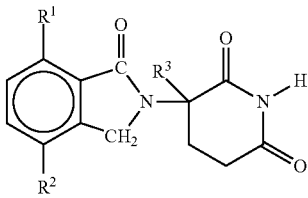

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other compounds that can be used in the methods provided herein are of formula:

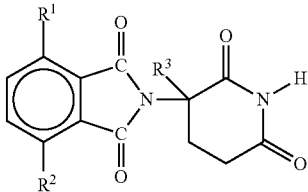

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl.

Other specific immunomodulatory compounds that can be used in the methods provided herein include, but are not limited to, 1-oxo and 1,3-dioxoisoindolines substituted in the 4- or 5-position of the indoline ring described in U.S. Pat. No. 6,380,239 and U.S. Application Publication No. 2006/0084815, which are incorporated herein by reference. Representative compounds are of formula:

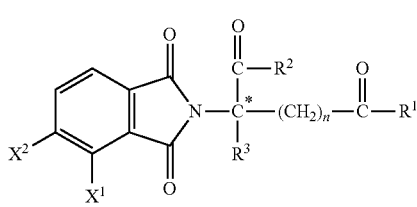

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further compounds that can be used in the methods provided herein are of formula:

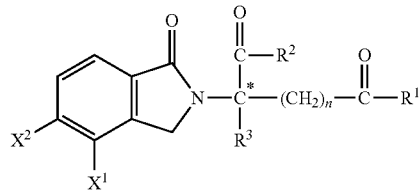

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples of compounds that can be used in the methods provided herein include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, prodrugs, and stereoisomers thereof:

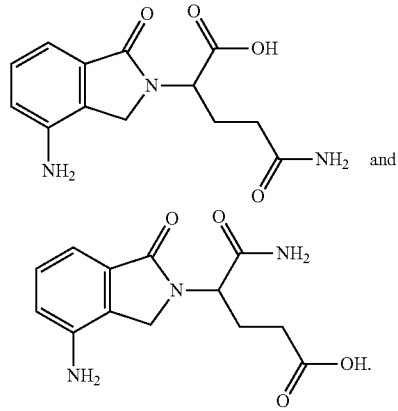

Other representative compounds are of formula:

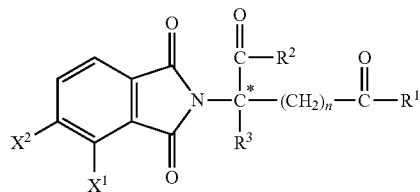

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

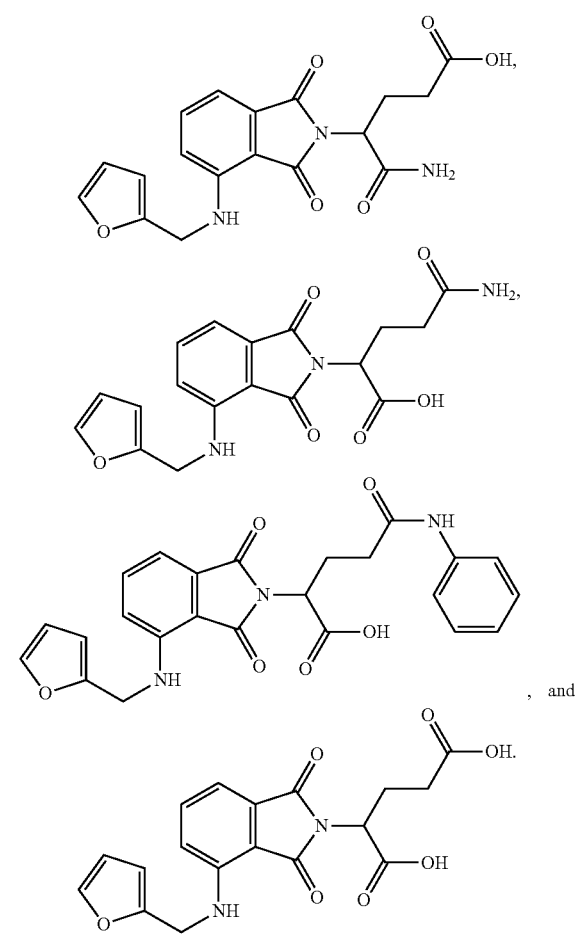

Other specific examples of the compounds are of formula:

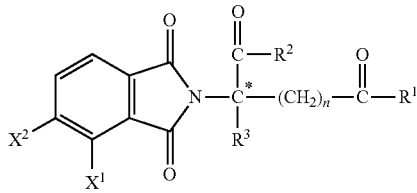

wherein one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2;
provided that if one of $X^1$ and $X^2$ is nitro, and n is 1 or 2, then $R^1$ and $R^2$ are other than hydroxy; and
if —COR$^2$ and —(CH$_2$)$_n$COR$^1$ are different, the carbon atom designated C* constitutes a center of chirality. Other representative compounds are of formula:

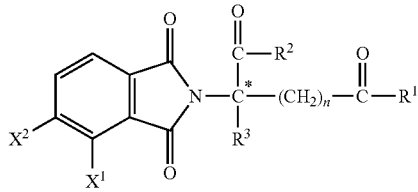

wherein one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —COR$^2$ and —(CH$_1$)$_n$COR$^1$ are different, the carbon atom designated C* constitutes a center of chirality.

Still other specific immunomodulatory compounds include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

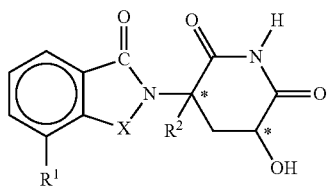

wherein:
the carbon atoms designated * constitute centers of chirality;
X is —C(O)— or —CH$_2$—;
$R^1$ is alkyl of 1 to 8 carbon atoms or —NHR$^3$;
$R^2$ is hydrogen, alkyl of 1 to 8 carbon atoms, or halogen; and
$R^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —COR$^4$ in which
$R^4$ is hydrogen,
alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

Compounds provided herein can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Various immunomodulatory compounds contain one or more chiral centers, and can exist as racemic mixtures of enantiomers or mixtures of diastereomers. Encompassed is the use of stereomerically pure forms of such compounds, as well as the use of mixtures of those forms. For example, mixtures comprising equal or unequal amounts of the enantiomers of a particular immunomodulatory compounds may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.9. Administration of PINK Cells, Human Placental Perfusate, or Combined Natural Killer Cells The PINK cells, human placental perfusate cells, combined natural killer cells, populations of cells comprising such cells, or combinations thereof, may be administered to an individual, e.g., an individual having tumor cells, e.g., a cancer patient, by any medically-acceptable route known in the art suitable to the administration of live cells. In various embodiments, the cells provided herein may be surgically implanted, injected, infused, e.g., by way of a catheter or syringe, or otherwise administered directly or indirectly to the site in need of repair or augmentation. In one embodiment, the cells are administered to an individual intravenously. In another embodiment, the cells are administered to the individual at the site of a tumor, e.g., a solid tumor. In a specific embodiment in which the individual has a tumor at more than one site, the cells are administered to at least two, or all, tumor sites. In certain other embodiments, the cells provided herein, or compositions comprising the cells, are administered orally, nasally, intraarterially, parenterally, ophthalmically, intramuscularly, subcutaneously, intraperitoneally, intracerebrally, intraventricularly, intracerebroventricularly, intrathecally, intracisternally, intraspinally and/or perispinally. In certain specific embodiments, the cells are delivered via intracranial or intravertebral needles and/or catheters with or without pump devices.

The PINK cells, human placental perfusate cells, combined natural killer cells, or combinations thereof, or cell populations comprising such cells, can be administered to an individual in a composition, e.g., a matrix, hydrogel, scaffold, or the like that comprise the cells.

In one embodiment, the cells provided herein are seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796, the disclosure of which is hereby incorporated by reference in its entirety.

In another embodiment, the PINK cells, human placental perfusate cells, combined natural killer cells, or combinations thereof, or cell populations comprising such cells, are suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. The cells in such a matrix can also be cultured so that the cells are mitotically expanded prior to implantation. The hydrogel can be, for example, an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix of the invention is biodegradable.

In some embodiments of the invention, the formulation comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells of the invention or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the invention.

Examples of scaffolds that can be used in the present invention include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ϵ-caprolactone)/poly(glycolic acid) (PCL/PGA) copolymer, formed by processes such as freeze-drying, or lyophilization (see, e.g., U.S. Pat. No. 6,355,699), can also be used as scaffolds.

Placental stem cells of the invention can also be seeded onto, or contacted with, a physiologically-acceptable ceramic material including, but not limited to, mono-, di-, tri-, alphatri-, beta-tri-, and tetra-calcium phosphate, hydroxyapatite, tluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS, RHAKOSS™ and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells of the invention can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1 M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasmacoating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

6. EXAMPLES

6.1. Example 1

Characterization of Placenta-Derived Intermediate Natural Killer Cells from Placental Perfusate and Umbilical Cord Blood The present example demonstrates the isolation and culture of natural killer cells from human placental perfusate.

Isolation of Placental Natural Killer Cells. Natural killer cells were isolated from 8 units of human placental perfusate (HPP), and from 4 units of umbilical cord blood (UCB), using CD56-conjugated microbeads. Isolation of PINK cells was conducted by magnetic bead selection (Miltenyi Biotec). The post partum placenta was exsanguinated and perfused with about 200 to about 750 mL of perfusion solution (0.9% NaCl injection solution USP Grade (Cat No. 68200-804, VWR). The unprocessed perfusate was collected and processed to remove erythrocytes. Mononuclear cells from HPP or UCB were washed one time with fluorescence-activated cell sorting (FACS) buffer (RPMI 1640, without phenol red, plus 5% FBS), then centrifuged at 1500 rpm for 6 minutes. The cell number was counted, and the cell pellet was resuspended in 80 µL of buffer per $10^7$ total cells with 20 µL of CD3 Microbeads (Catalog No. 130-050-101, Miltenyi). The system was mixed well and incubated for 15 minutes at 4-8° C. 1-2 mL of buffer per $10^7$ total cells was added, and the mixture was then centrifuged at 300 g for 10 minutes. The supernatant was pipetted off completely. The cell pellet was resuspended up to $10^8$ cells in 500 µL of buffer and prepared for magnetic separation. An LS column (Miltenyi Biotec) was placed in the magnetic field of a MIDIMACS™ cell separator (Miltenyi Biotec), 3 mL buffer was applied to rinse the column, and the cell/microbead suspension was applied to the column. Unlabeled CD3⁻ cells, which passed through the column and which would include natural killer cells, were collected, together with 2×3 mL washing buffer. The CD3⁻ cells were counted, washed one time, then were stained with CD56 MicroBeads (Cat#: 130-050-401, Miltenyi), and separated/isolated using the same protocol as for the CD3 microbead separation described above. A CD56+CD3− population was thus collected and ready for further analysis. The percentage range of natural killer cells was 3.52 to 11.6 (median 6.04, average 5.22) in HPP, and 1.06 to 8.44 in UCB (median: 3.42, average: 4.2). CD56 microbead selection of natural killer cells from HPP produced a population that was approximately 80% pure. See FIG. 1. Among the whole CD56⁺, CD3 natural killer cell population, the percentage range of CD56⁺, CD16⁻ natural killer cells (that is, PINK cells) was 56.6 to 87.2 (median 74.2, average 65.5) from HPP, and 53.7 to 96.6 (median 72.8) from UCB. The percentage range of CD56⁺, CD16⁺ natural killer cells was 12.8 to 43.3 (median 25.8, average 34.5) from HPP, and 3.4 to 46.3 (median 27.3, average 33.4) for UCB.

In other experiments, natural killer cells were isolated using a magnetic negative selection kit that targets cell surface antigens on human blood cells (CD3, CD4, CD14, CD19, CD20, CD36, CD66b, CD123, HLA-DR, glycophorin A). HPP and UCB cryopreserved units were thawed and diluted at 1:1 with Thaw media (RPMI Media 1640 (Catalog #22400, Gibco) plus 20% Fetal Bovine Serum-Heat Inactivated (Catalog #SH30070.03, Hyclone)) and centrifuged at 1500 rpm for 8 minutes. The supernatant was removed and ammonium chloride treatment was applied to further deplete erythrocytes; each unit was resuspended in approximately 30 mL of ice cold FACS buffer (RPMI 1640, without phenol red, plus 5% FBS), and then 60 mL ice cold ammonium chloride (Catalog #07850, Stem Cell) was added, the solution was vortexed and then incubated on ice for 5 minutes. The mononuclear cells were then washed with FACS buffer 3 times and then centrifuged at 1500 rpm for 8 minutes. The cell number was counted and the cell pellet was resuspended in 5×$10^7$ live cells/ml in RoboSep Buffer (Catalog #20104, Stem Cell) plus 0.1 mg/mL DNAase I solution (Catalog #07900, Stem Cell)

was added to the cell suspension, mixed gently by pipette and incubated 15 minutes at room temperature prior to isolation. Clumps were removed from the cell suspension by filtering with 40 µm mesh nylon strainer (Catalog #352340, BD Falcon) before proceeding to isolation. Isolation is automated by the device RoboSep (Catalog #20000, Stem Cell) and the program "Human NK Negative Selection 19055 and high recovery" (50 µL/mL cocktail addition, 100 µL/mL Microparticle addition, 10 and 5 minute incubations, 1×2.5 minute separations) with Human NK Cell Enrichment Kit (Catalog #19055, Stem Cell) including EasySep Negative Selection Human NK Cell Enrichment Cocktail and EasySep Magnetic Microparticles. A CD56$^+$CD3$^-$ population was thus collected and ready for further analysis.

Expansion of Natural Killer Cells. In general, natural killer cells were expanded as follows. Start Medium for natural killer cell culture was prepared based on a modification of a protocol described in Yssel et al., *Immunol. Methods* 72(1): 219-227 (1984) and Litwin et al., *J. Exp. Med.* 178(4):1321-1326 (1993). Briefly, Start Medium includes IMDM (Invitrogen) with 10% FCS (Hyclone), containing the following reagents with final concentration of 35 µg/mL transferrin (Sigma-Aldrich), 5 µg/mL insulin (Sigma-Aldrich), 2×10$^{-5}$ M ethanolamine (Sigma-Aldrich), 1 µg/mL oleic acid (Sigma-Aldrich), 1 µg/mL linoleic acid (Sigma-Aldrich), 0.2 µg/mL palmitic acid (Sigma-Aldrich), 2.5 µg/mL BSA (Sigma-Aldrich) and 0.1 µg/mL Phytohemagglutinin (PHA-P, Sigma-Aldrich). CD56$^+$CD3$^-$ NK cells were resuspended at 2.5×10$^5$ live cells/mL Start Medium plus 200 iu/mL IL-2 (R&D Systems) in cell culture treated 24-well plate or T flask. Mitomycin C-treated allogenic PBMC and K562 cells (chronic myelogenous leukemia cell line) were both added to the Start Medium as feeder cells, to a final concentration of 1×10$^6$ per mL. NK cells were cultured for 5-6 days at 37° C. in 5% CO$_2$. After 5-6 days and then every 3-4 days an equal volume of Maintenance Medium (IMDM with 10% FCS, 2% Human AB serum, antibiotics, L-glutamine and 400 units of IL-2 per mL) was added to the culture. NK cells were harvested at day 21.

Characterization of Placenta-Derived Intermediate Natural Killer Cells. Donor matched HPP and CB was thawed, and the cells were washed with FACS buffer (RPMI-1640 with 5% FBS). Natural killer cells were then enriched with CD56 microbeads using the ROBOSEP® magnetic separation system (StemCell Technologies) as instructed by the manufacturer. The CD56 enriched natural killer cell population was stained with the following antibodies (BD Bioscience if not otherwise indicated) for immunophenotypic characterization: anti-CD56 conjugated to PE-Cy-7, anti-CD3 APC Cy7, anti-CD16 FITC, anti-NKG2D APC, anti-NKp46 APC, anti-CD94 PE(R&D), anti-NKB1 PE, and anti-KIR-NKAT2 PE. CD94, NKG2D and NKp46 are markers absent, or showing reduced expression, in NK cell progenitors but present on fully-differentiated NK cells. See Freud et al., "Evidence for Discrete States of Human Natural Killer Cell Differentiation In Vivo," *J. Exp. Med.* 203(4):1033-1043 (2006); Eagle & Trowsdale, "Promiscuity and the Single Receptor: NKG2D," *Nature Reviews Immunology* Published online Aug. 3, 2007; Walzer et al., "Natural Killer Cells: From CD3$^-$NKp46$^+$ to Post-Genomics Meta-Analyses," *Curr. Opinion Immunol.* 19:365-372 (2007). As shown in Table 1, expression of KIR3DL1, KIR2DL2/L3, NKG2D, NKp46 and CD94 was not significantly different between an enriched CD56$^+$ cell population from HPP and an HLA-matched CD56$^+$ cell population from umbilical cord blood (CB).

TABLE 1

Percentage of NK cells bearing certain marker combinations. Mean of 3 samples.

| | Mean (%) | | |
|---|---|---|---|
| | CB | HPP | p value |
| CD3−CD56+ | 0.6 | 0.7 | 0.799 |
| CD3−CD56+CD16− | 53.9 | 58.7 | 0.544 |
| CD3−CD56+CD16+ | 46.1 | 41.3 | 0.544 |
| CD3−CD56+KIR3DL1+ | 5.8 | 7.3 | 0.762 |
| CD3−CD56+KIR2DL2/L3+ | 10.7 | 9.9 | 0.89 |
| CD3−CD56+NKG2D+ | 60.3 | 58.5 | 0.865 |
| CD3−CD56+CD94+ | 74.6 | 76.8 | 0.839 |

6.2. Example 2

Characterization of Placenta-Derived Intermediate Natural Killer Cells From Combined Placental Perfusate and Umbilical Cord Blood Donor matched mononucleated cells of umbilical cord blood and placental perfusate (combo) were mixed and washed with FACS buffer (RPMI-1640 with 5% FBS) once and immunophenotypically characterized using the antibodies listed in Table 2 on a BD FACSCanto (BD Biosciences). The data were analyzed by FlowJo software (Tree Star).

TABLE 2

List of antibodies used in immunophenotypic characterization.

| Item | vendor | Cat No. |
|---|---|---|
| FITC anti-hu CD3 | BD Bioscience | 555332 |
| FITC anti-hu CD3 | Miltenyi | 130-080-401 |
| APC-Cy7 anti-hu CD3 | BD Bioscience | 557832 |
| FITC anti-hu CD16 | BD Bioscience | 555406 |
| PE-Cy5 anti-hu CD16 | BD Bioscience | 555408 |
| PE anti-hu CD56 | BD Bioscience | 555516 |
| PE anti-hu CD56 | Miltenyi | 130-090-755 |
| PE-CY5 anti-hu CD56 | BD Bioscience | 555517 |
| PE-Cy7 anti-hu CD56 | BD Bioscience | 557747 |
| PE anti-hu CD94 | R&D | FAB-1058P |
| PE anti-hu KIR-NKAT2 (2DL2/L3) | BD Bioscience | 556071 |
| PE anit-hu NKB1(3DL1) | BD Bioscience | 555967 |
| APC anit-hu NKG2D | BD Bioscience | 558071 |
| APC anit-hu NKp46 | BD Bioscience | 558051 |
| PE anti-hu CD226 | BD Bioscience | 559789 |
| PE anit-hu NKp44 | BD Bioscience | 558563 |
| PE anti-hu NKp30 | BD Bioscience | 558407 |
| PE anti-hu 2B4 | BD Bioscience | 550816 |
| Isotype FITC mouse IgG1 | BD Bioscience | 340755 |
| Isotype FITC mouse IgG2b | BD Bioscience | 556577 |
| Isotype PE mouse IgG1 | BD Bioscience | 340761 |
| Isotype PE mouse IgG2b | BD Bioscience | 555743 |
| Isotype PerCP mouse IgG1 | BD Bioscience | 340762 |
| Isotype PE-Cy5 mouse IgG2b | BD Bioscience | 555744 |
| Isotype APC mouse IgG1 | BD Bioscience | 340754 |
| Isotype APC mouse IgG2a | BD Bioscience | 555576 |
| Isotype APC-Cy7 mouse IgG1 | BD Bioscience | 348802 |
| Isotype PE-Cy7 mouse IgG1 | BD Bioscience | 348798 |

Immunophenotypic Characterization of Placental NK Cells and Peripheral Blood (PB) NK Cells. NK cells can be divided into two main groups: CD56$^+$CD16$^+$ NK cells, and CD56$^+$CD16$^-$ cells. CD56$^+$CD16$^+$ NK cells have abundant cytolytic granules and high expression of CD16, and are therefore capable of eliciting antibody-dependent cell-mediated cytotoxicity (ADCC). CD56$^+$CD16$^-$ NK cells, conversely, have very few cytolytic granules, low or no expression of CD16, but are capable of producing cytokines and chemokines upon activation. Individual NK cells display a diverse repertoire of activating and inhibitory receptors, including the killer immunoglobulin-like receptors (KIRs, e.g., KIR3DL1, and KIR2DL2/3), natural cytotoxicity receptors NCRs (e.g., NKp30, NKp44, and NKp46), killer cell lectin-like receptors (KLRs; e.g., CD94, NKG2D), 2B4 and CD226.

FACS analysis was performed on placental NK and peripheral blood NK cells using fluorescence-conjugated mAbs against specific NK receptors. Among 11 NK subsets characterized, the numbers of cells in seven out of 11 NK subsets (CD3$^-$CD56$^+$CD16$^-$, CD3$^-$CD56$^+$CD16$^+$, CD3$^-$CD56$^+$KIR2DL2/3$^+$, CD3$^-$CD56NKp46$^{30}$, CD3$^-$CD56$^+$NKp30$^+$, CD3$^-$CD56$^+$2B4$^+$ and CD3$^-$CD56$^+$CD94$^+$) showed significant difference (p<0.05) between placental NK and peripheral blood NK cells (accounted for 64% difference) (Table 3A; see also Tables 3B and 3C).

TABLE 3A

Phenotypic characterization of CD3$^-$CD56$^+$ NK cells in 16 units of combined donor-matched umbilical cord blood and human placental perfusate (combo) and 13 units of peripheral blood (PB). The two-sample t-test is used to determine if population means are equal in placental and peripheral blood units.

| Surface markers | Combo (16 units) Mean % | PB (13 units) Mean % | P Value |
|---|---|---|---|
| CD3-CD56+ | 2.2 | 2.4 | 0.728 |
| CD3-CD56+CD16- | 60.9 | 21.4 | 0.000 |
| CD3-CD56+CD16+ | 39.1 | 78.6 | 0.000 |
| CD3-CD56+KIR3DL1 | 12.3 | 7.1 | 0.099 |
| CD3-CD56+KIR2DL2/L3 | 21.9 | 9.5 | 0.004 |
| CD3-CD56+NKG2D | 42.1 | 29.9 | 0.126 |
| CD3-CD56+NKp46 | 7.0 | 18.9 | 0.011 |
| CD3-CD56+CD226 | 16.0 | 26.7 | 0.135 |
| CD3-CD56+NKp44 | 9.5 | 4.9 | 0.073 |
| CD3-CD56+NKp30 | 39.1 | 19.0 | 0.006 |
| CD3-CD56+2B4 | 11.1 | 4.5 | 0.019 |
| CD3-CD56+CD94 | 71.3 | 26.2 | 0.000 |

Tables 3B and 3C show the phenotypic characterization of CD3$^-$CD56$^+$CD16$^-$ and CD3$^-$CD56$^+$CD16$^+$ NK cells in 16 units of combined donor-matched umbilical cord blood and human placental perfusate (combo) and 13 units of peripheral blood (PB) in a separate experiment.

TABLE 3B

| Surface markers | Combo Mean % | PB Mean % | P Value |
|---|---|---|---|
| CD3-CD56+CD16- | 62.3 | 14.1 | 0.000 |
| CD3-CD56+CD16-KIR3DL1 | 7.8 | 1.5 | 0.004 |
| CD3-CD56+CD16-NKG2D | 43.5 | 42.7 | 0.941 |
| CD3-CD56+CD16-KIR2DL2/L3 | 13.6 | 2.4 | 0.000 |
| CD3-CD56+CD16-NKp46 | 6.7 | 43.6 | 0.001 |
| CD3-CD56+CD16-CD94 | 69.8 | 48.5 | 0.057 |
| CD3-CD56+CD16-CD226 | 7.6 | 4.9 | 0.068 |
| CD3-CD56+CD16-NKp44 | 3.4 | 0.6 | 0.076 |
| CD3-CD56+CD16-NKp30 | 46.7 | 22.0 | 0.000 |
| CD3-CD56+CD16-2B4 | 3.7 | 0.5 | 0.078 |

TABLE 3C

| Surface markers | Combo Mean % | PB Mean % | P Value |
|---|---|---|---|
| CD3-CD56+CD16+ | 37.7 | 85.9 | 0.000 |
| CD3-CD56+CD16+KIR3DL1 | 21.5 | 8.9 | 0.014 |
| CD3-CD56+CD16+NKG2D | 42.1 | 28.5 | 0.066 |
| CD3-CD56+CD16+KIR2DL2/L3 | 34.5 | 12.1 | 0.000 |
| CD3-CD56+CD16+NKp46 | 10.4 | 14.5 | 0.242 |
| CD3-CD56+CD16+CD94 | 72.9 | 23.8 | 0.000 |
| CD3-CD56+CD16+CD226 | 35.5 | 32.6 | 0.347 |
| CD3-CD56+CD16+NKp44 | 22.6 | 6.4 | 0.016 |
| CD3-CD56+CD16+NKp30 | 45.7 | 19.7 | 0.000 |
| CD3-CD56+CD16+2B4 | 31.2 | 6.1 | 0.008 |

60.9% of placental NK cells are CD56$^+$CD16$^-$ (placenta-derived intermediate natural killer (PINK) cells) while only 21.4% of peripheral blood NK cells are CD56$^+$CD16$^-$. After cultivation for 21 days, the percentage of four out 11 NK subsets (CD3$^-$CD56$^+$KIR2DL2/3$^+$, CD3$^-$CD56$^+$NKp46$^-$, CD3$^-$CD56$^+$NKp44$^+$ and CD3$^-$CD56$^-$NKp30$^+$) showed significant difference (p<0.05) between placental and peripheral blood NK cells (Table 4).

TABLE 4

Phenotypic characterization of day 21-cultured NK cells derived from 12 units of combined donor-matched umbilical cord blood and human placental perfusate (Combo), and 9 units of peripheral blood (PB). The two-sample t-test is used to determine if population means are equal in combo and peripheral blood units.

| Surface markers | Combo (16 units) Mean % | PB (13 units) Mean % | P Value |
|---|---|---|---|
| CD3-CD56+ | 2.2 | 2.4 | 0.728 |
| CD3-CD56+CD16- | 60.9 | 21.4 | 0.000 |
| CD3-CD56+CD16+ | 39.1 | 78.6 | 0.000 |
| CD3-CD56+KIR3DL1 | 12.3 | 7.1 | 0.099 |
| CD3-CD56+KIR2DL2/L3 | 21.9 | 9.5 | 0.004 |
| CD3-CD56+NKG2D | 42.1 | 29.9 | 0.126 |
| CD3-CD56+NKp46 | 7.0 | 18.9 | 0.011 |
| CD3-CD56+CD226 | 16.0 | 26.7 | 0.135 |
| CD3-CD56+NKp44 | 9.5 | 4.9 | 0.073 |
| CD3-CD56+NKp30 | 39.1 | 19.0 | 0.006 |
| CD3-CD56+2B4 | 11.1 | 4.5 | 0.019 |
| CD3-CD56+CD94 | 71.3 | 26.2 | 0.000 |

In addition, in a separate experiment, it was determined that, after cultivation for 21 days, placental and peripheral blood NK cells demonstrated unique cytokine profiles, particularly for IL-8, as determined by Luminex assay (Table 5).

TABLE 5

| Cytokine | PB (pg/mL) | Combo (pg/mL) |
|---|---|---|
| IL-13 | 1.26 | 1.89 |
| IL-8 | 6.61 | 15.77 |
| IL-10 | 1.26 | 2.23 |
| TNFa | 0.28 | 0.34 |
| MCP-1 | 10.49 | 11.32 |

MicroRNA Profiling of Placental NK Cells and Peripheral Blood NK Cells. Isolated or expanded NK cells were subjected to microRNA (miRNA) preparation using a MIR-VANA™ miRNA Isolation Kit (Ambion, Cat#1560). NK cells (0.5 to 1.5×10$^6$ cells) were disrupted in a denaturing lysis buffer. Next, samples were subjected to acid-phenol+chloroform extraction to isolate RNA highly enriched for small RNA species. 100% ethanol was added to bring the samples to 25% ethanol. When this lysate/ethanol mixture was passed through a glass fiber filter, large RNAs were immobilized, and the small RNA species were collected in the filtrate. The ethanol concentration of the filtrate was then increased to 55%, and the mixture was passed through a second glass fiber filter where the small RNAs became immobilized. This RNA was washed a few times, and eluted in a low ionic strength solution. The concentration and purity of the recovered small RNA was determined by measuring its absorbance at 260 and 280 nm.

miRNAs found to be unique for PINK cells are shown in Table 6. One miRNA, designated hsa-miR-199b, was found to be unique for peripheral blood NK cells.

inhibitory receptors) remained not affected during 21-day expansion. The changes in the expression NKRs were further correlated with a marked increase in cytolytic activity at day 21 versus day 14 against K562 cells (63%±15% versus 45%±4%, p value of 0.0004). These findings have led to identification of the putative markers of NK cells which correlate well with the NK cell cytotoxicity activity.

TABLE 6 miRNA profiling for piNK cells and PB NK cells via qRT-PCR.

| miRNA ID | Sanger Accession No. | Sequence |
| --- | --- | --- |
| hsa-miR-100 | MIMAT0000098 | aacccguagauccgaacuugug |
| hsa-miR-127 | MIMAT0000446 | ucggauccgucugagcuuggcu |
| hsa-miR-211 | MIMAT0000268 | uucccuuugucauccuucgccu |
| hsa-miR-302c | MIMAT0000717 | uaagugcuuccauguuucagugg |
| hsa-miR-326 | MIMAT0000756 | ccucugggcccuuccuccag |
| hsa-miR-337 | MIMAT0000754 | uccagcuccuauaugaugccuuu |
| hsa-miR-497 | MIMAT0002820 | cagcagcacacugugguuugu |
| hsa-miR-512-3p | MIMAT0002823 | aagugcugucauagcugagguc |
| hsa-miR-515-5p | MIMAT0002826 | uucuccaaaagaaagcacuuucug |
| hsa-miR-517b | MIMAT0002857 | ucgugcaucccuuuagaguguu |
| hsa-miR-517c | MIMAT0002866 | aucgugcauccuuuuagagugu |
| hsa-miR-518a | MIMAT0002863 | aaagcgcuucccuuugcugga |
| hsa-miR-518e | MIMAT0002861 | aaagcgcuucccuucagagug |
| hsa-miR-519d | MIMAT0002853 | caaagugccucccuuuagagug |
| hsa-miR-520g | MIMAT0002858 | acaaagugcuucccuuuagagugu |
| hsa-miR-520h | MIMAT0002867 | acaaagugcuucccuuuagagu |
| hsa-miR-564 | MIMAT0003228 | aggcacggugucagcaggc |
| hsa-miR-566 | MIMAT0003230 | gggcgccugugaucccaac |
| hsa-miR-618 | MIMAT0003287 | aaacucuacuuguccuucugagu |
| hsa-miR-99a | MIMAT0000097 | aacccguagauccgaucuugug |

Immunophenotypic Characterization of Cultured Placental NK Cells and Uncultured NK Cells. The overall properties of cultured PINK cells were evaluated by extensive immunophenotypic studies and cytotoxicity assays. To determine the phenotype of expanded NK cells, expression of NK receptors (NKRs) such as KIRs, NKG2D, NKp46, NKp44 and 2B4 were analyzed. Cytotoxicity assays were performed by labeling tumor cells (K562 cells) with PKH26 then co-culturing with PINK cells for 4 hours. From day 0 to day 21 the expression of NKG2D was increased from 60.9%±4.8% to 86%±17.4% (p value of 0.024); NKp46 was increased from 10.5%±5.4% to 82.8%±9.0% (p value of 0.00002); NKp44 was increased from 9.6%±6.5% to 51.6%±27.5% (p value of 0.022); and 2B4 was decreased from 13.0%±7.1% to 0.65%±0.5% (p value of 0.009%) (Table 7). Under these culture conditions the inhibitory KIRs including KIR3DL1 (killer cell immunoglobulin-like receptor, three domains, long cytoplasmic tail 1, an inhibitory receptor) and KIR2DL2/L3 (killer cell immunoglobulin-like receptor, two domains, long cytoplasmic tail 2 and long cytoplasmic tail 3;

TABLE 7

Phenotypic characterization of piNK cells before and after 21-day cultivation. Standard deviation (Stdev) was calculated for population means for 5 donors.

| | Day 0 | | Day 21 | |
| --- | --- | --- | --- | --- |
| | Mean % | Stdev | Mean % | Stdev |
| CD3−CD56+ | 2.9 | 1.1 | 85.5 | 8.6 |
| CD3−CD56+CD16− | 62.6 | 20.2 | 27.8 | 8.3 |
| CD3−CD56+CD16+ | 37.4 | 20.2 | 72.2 | 8.3 |
| CD3−CD56+KIR3DL1+ | 22.7 | 4.2 | 20.0 | 16.7 |
| CD3−CD56+KIR2DL2/L3+ | 28.4 | 4.2 | 29.6 | 6.4 |
| CD3−CD56+NKG2D+ | 60.9 | 4.8 | 86.0 | 17.4 |
| CD3−CD56+NKp46+ | 10.5 | 5.4 | 82.8 | 8.9 |
| CD3−CD56+CD226+ | 19.5 | 7.4 | 14.1 | 13.3 |
| CD3−CD56+NKp44+ | 9.6 | 6.5 | 51.6 | 27.5 |
| CD3−CD56+NKp30+ | 58.9 | 7.0 | 76.5 | 19.4 |
| CD3−CD56+2B4+ | 13.0 | 7.1 | 0.6 | 0.5 |
| CD3−CD56+CD94+ | 79.7 | 4.9 | 63.9 | 19.4 |

Membrane Proteomic Profiling of Cultured Placental NK Cells and Cultured Peripheral Blood NK Cells Via Lipid-Based Protein Immobilization Technology and Linear Ion Trap LC/MS. Membrane Protein Purification: Placental natural killer cells from combined placental perfusate and cord blood cells, and PB NK cells, cultured for 21 days, were incubated for 15 min with a protease inhibitor cocktail solution (P8340, Sigma Aldrich, St. Louis, Mo.; contains 4-(2-aminoethyl)benzenesulfonyl fluoride (AEBSF), pepstatin A, E-64, bestatin, leupeptin, and aprotinin, without metal chelators) prior to cell lysis. The cells were then lysed by the addition of a 10 mM HCl solution, without detergents, and centrifuged for 10 min at 400 g to pellet and remove the nuclei. The post-nuclear supernatant was transferred to an ultracentriguation tube and centrifuged on a WX80 ultracentrifuge with T-1270 rotor (Thermo Fisher Scientific, Asheville, N.C.) at 100,000 g for 150 minutes generating a membrane protein pellet.

Generation, Immobilization and Digestion of Proteoliposomes: The membrane protein pellet was washed several times using NANOXIS® buffer (10 mM Tris, 300 mM NaCl, pH 8). The membrane protein pellet was suspended in 1.5 mL of NANOXIS® buffer and then tip-sonicated using a VIBRA-CELL™ VC505 ultrasonic processor (Sonics & Materials, Inc., Newtown, Conn.) for 20 minutes on ice. The size of the proteoliposomes was determined by staining with FM1-43 dye (Invitrogen, Carlsbad, Calif.) and visualization with fluorescence microscopy. The protein concentration of the proteoliposome suspension was determined by a BCA assay (Thermo Scientific). The proteoliposomes were then injected onto an LPI™ Flow Cell (Nanoxis AB, Gothenburg, Sweden) using a standard pipette tip and allowed to immobilize for 1 hour. After immobilization, a series of washing steps were carried out and trypsin at 5 µg/mL (Princeton Separations, Adelphi, N.J.) was injected directly onto the LPI™ Flow Cell. The chip was incubated overnight at 37° C. Tryptic peptides were then eluted from the chip and then desalted using a Sep-Pak cartridge (Waters Corporation, Milford, Mass.).

Strong Cation-Exchange (SCX) Fractionation: Tryptic peptides were reconstituted in a 0.1% formic acid/water solution and loaded onto a strong-cation exchange (SCX) TOP-TIP™ column (PolyLC, Columbia, Md.), a pipette tip packed with 30 µm polysufoETHYL aspartamide SCX packing material. Peptides were eluted from the SCX TOP-TIP™ using a step-gradient of ammonium formate buffer, pH 2.8 (10 mM-500 mM). Each SCX fraction was dried using a speed-vac system and reconstituted with 5% acetonitrile, 0.1% Formic Acid in preparation for downstream LC/MS analysis.

LTQ Linear Ion Trap LC/MS/MS Analysis: Each SCX fraction was separated on a 0.2 mm×150 mm 3 µm 200 Å MAGIC C18 column (Michrom Bioresources, Inc., Auburn, Calif.) that was interfaced directly to an axial desolvation vacuum-assisted nanocapillary electrospray ionization (AD-VANCE) source (Michrom Bioresources, Inc.) using a 180 min gradient (Buffer A: Water, 0.1% Formic Acid; Buffer B: Acetonitrile, 0.1% Formic Acid). The ADVANCE source achieves a sensitivity that is comparable to traditional nanoESI while operating at a considerably higher flow rate of 3 µL/min. Eluted peptides were analyzed on an LTQ linear ion trap mass spectrometer (Thermo Fisher Scientific, San Jose, Calif.) that employed ten data-dependent MS/MS scans following each full scan mass spectrum.

Bioinformatics: Six RAW files corresponding to the 6 salt fractions that were collected for each tumor cell line (AML, CML) were searched as a single search against the IPI Human Database using an implementation of the SEQUEST algorithm on a SORCERER™ SOLO™ workstation (Sage-N Research, San Jose, Calif.). A peptide mass tolerance of 1.2 amu was specified, oxidation of methionine was specified as a differential modification, and carbamidomethylation was specified as a static modification. A Scaffold software implementation of the Trans-Proteomic Pipeline (TPP) was used to sort and parse the membrane proteomic data. Proteins were considered for analysis if they were identified with a peptide probability of 95%, protein probability of 95% and 1 unique peptide. Comparisons between membrane proteomic datasets were made using custom Peri scripts that were developed in-house.

The analysis revealed the identification of 8 membrane proteins from cultured placental NK cells that were unique with respect to membrane proteins identified from peripheral blood NK cells. See Table 8. Further, 8 membrane proteins were identified from peripheral blood NK cells that were unique with respect to cultured placental NK cells. See Table 8. Only 10 membrane proteins identified were found to be shared among both cultured placental NK cells and peripheral blood NK cells.

TABLE 8

| PROTEINS SPECIFIC FOR PLACENTAL NK CELLS | PROTEINS SPECIFIC FOR PB NK CELLS |
|---|---|
| Aminopeptidase N | Fibroblast growth factor receptor 4 precursor |
| Apolipoprotein E | Immunity-associated nucleotide 4-like 1 protein |
| Atrophin-1 interacting protein 1 | Integrin alpha-L precursor |
| Innexin inx-3 | Integrin beta-2 precursor |
| Integrin alpha-2 precursor | Integrin beta-4 precursor |
| Integrin beta-5 precursor | Membrane-bound lytic murein transglycosylase D precursor |
| Mast cell surface glycoprotein GP49B precursor | Oxysterol binding protein-related protein 8 |
| Ryanodine receptor 1 | Perforin 1 precursor |

6.3. Example 3

Natural Killer Cell Cytotoxicity Towards Tumor Cells

This example demonstrates that placental intermediate natural killer cells are cytotoxic towards tumor cells. PINK cells from HPP are cytotoxic to acute myelogenous leukemia cells, as demonstrated in a cytotoxicity assay and by Luminex analysis of NK cell cytokine secretion.

In the cytokine secretion assay, CD56 microbead-enriched NK cells from HPP were mixed with KG-1a acute myelogenous leukemia cells at a 1:1 ratio. After incubation for 24 hours, supernatant was collected and subjected to Luminex analysis of IFN-γ and GM-CSF secretion. Increased levels of IFN-γ and GM-CSF was observed after 24 h incubation of CD56-enriched HPP cells with KG-1a cells as shown in FIG. 2.

Cytotoxicity of PINK Cells

In a cytotoxicity assay utilizing PINK cells, target tumor cells were labeled with carboxyfluoroscein succinimidyl ester (CFSE). CFSE is a vital stain that is non-toxic to cells, and is partitioned between daughter cells during cell division. The cells were then placed in 96-well U-bottomed tissue culture plates and incubated with freshly isolated CD56+ CD16− PINK cells at effector-target (E:T) ratios of 20:1, 10:1, 5:1 and 1:1 in RPMI 1640 supplemented with 10% FBS. After a 4 hour incubation time, cells were harvested and examined by flow cytometry for the presence of CFSE. The number of target cells recovered from culture without NK cells was used as a reference. Cytotoxicity is defined as: $(1-CFSE_{sample}/CFSE_{control})*100\%$. Significant tumor cell cytotoxicity was observed at the 20:1 ratio. See FIG. 3.

Tumor Cell Susceptibility to Cultured PINK Cells

Lactate Dehydrogenase (LDH)—Release Assay. The LDH—release assay was performed using the CYTOTOX 96® colorimetric cytotoxicity assay kit (Promega, Cat#G1780). In this assay, cultured NK cells, comprising a combination of $CD56^+$ $CD16^-$ cells and $CD56^+CD16^+$ cells derived from matched HPP/UCB, were effector cells, and tumor cells were target cells. Effector cells and target cells were placed in 96-well U-bottom tissue culture plates and incubated at various effector-target (E:T) ratios in 100 µl RPMI 1640 without phenol red (Invitrogen, Cat#11835-030) supplemented with 2% human AB serum (Gemini, Cat#100-512). Cultures were incubated for 4 h at 37° C. in 5% $CO_2$. After incubation, 50 µl supernatant was transferred to enzymatic assay plate, LDH activity was detected as provided by the manufacturer, and absorption was measured at 490 nm in an ELISA reader (Synergy HT, Biotek). The degree of cytotoxicity was calculated according to the following equation: % Cytotoxicity= (Sample-Effector Spontaneous-Target Spontaneous)/(Target maximum-Target Spontaneous)*100.

Certain tumor types may be more responsive to NK cells than others. To analyze susceptibility of tumor cells to cultured PINK cells, twelve different tumor cell lines, cocultured with PINK cells, were analyzed in an LDH release assay. The 12 tumor cell lines included human chronic myelogenous leukemia (CML), lymphoma, retinoblastoma (RB), and multiple myeloma (MM) (Table 9). The NK cell cytotoxicity was measured by the LDH release assay after 4-hour co-culture.

TABLE 9

ATCC Tumor cell lines

| Name | Description |
| --- | --- |
| CCRF-CEM | Human leukemia |
| KG-1 | Human acute myeloid leukemia |
| KG-1A | Human acute myeloid leukemia |
| K562 | Human chronic myeloid leukemia |
| KU812 | Human chronic myeloid leukemia |
| U-937 | Human histiocytic lymphoma |
| WERI-RB-1 | Human retinoblastoma |
| HCC2218 | Human breast cancer |
| RPMI 8226 | Human multiple myeloma |
| HCT116 | Human colorectal carcinoma |
| HT29 | Human colorectal adenocarcinama |
| U266 | Human multiple myeloma |

At effector to target (E:T) ratio of 10:1 significant cytotoxicity of cultured PINK cells was seen towards K562 cells (CML) at 88.6%±5.6%, U937 cells (lymphoma) at 89.2%±9.8%, WERI-RB-1 cells (RB) at 73.3%±11.8%, RPMI8226 cells (MM) at 61.3%±1.3%, and U266 cells (MM) at 57.4%±4.7% (Table 10).

TABLE 10

Differential susceptibility of tumor cells to cultured piNK cells. Standard error of the mean (S. E. M.) was calculated for average cytotoxicity from 3 donors.

| Cell Line | % Cytotoxicity | S.E.M |
| --- | --- | --- |
| CCRF-CEM | 7.6 | 1.2 |
| KG-1 | 20.5 | 1.5 |

TABLE 10-continued

Differential susceptibility of tumor cells to cultured piNK cells. Standard error of the mean (S. E. M.) was calculated for average cytotoxicity from 3 donors.

| Cell Line | % Cytotoxicity | S.E.M |
| --- | --- | --- |
| KG-1a | 6.0 | 3.2 |
| K562 | 88.6 | 5.6 |
| KU812 | 40.3 | 8.2 |
| U937 | 89.2 | 9.8 |
| WERI-RB-1 | 73.3 | 11.8 |
| RPMI8226 | 61.3 | 1.3 |
| U266 | 57.4 | 4.7 |
| HCT-116 | 61.0 | 5.1 |
| HCC2218 | 14.8 | 3.7 |
| HT-29 | 45.6 | 6.0 |

Enhancement of PINK Cell Cytotoxicity By Treatment with Lenalidomide and Potnalidomide RNA Isolation and Purification. Isolated or expanded NK cells were subjected to RNA preparation using RNAQUEOUS®-4PCR Kit (Ambion, Cat #AM1914). In brief, NK cells (0.5 to 1.5×10⁶ cells) were lysed in the guanidinium lysis solution. The sample lysate was then mixed with an ethanol solution, and applied to a silica-based filter which selectively and quantitatively binds mRNA and the larger ribosomal RNAs; very small RNAs such as tRNA and 5S ribosomal RNA were not quantitatively bound. The filter was then washed to remove residual DNA, protein, and other contaminants, and the RNA was eluted in nuclease-free water containing a trace amount of EDTA to chelate heavy metals. The silica filter was housed in a small cartridge which fits into the RNase-free microfuge tubes supplied with the kit. The sample lysate, wash solutions, and elution solution were moved through the filter by centrifugation or vacuum pressure. After elution from the filter the RNA was treated with the ultra-pure DNase 1 provided with the kit to remove trace amounts of DNA. Finally, the DNase and divalent cations were removed by a reagent also provided with the kit. The concentration and purity of the recovered RNA was determined by measuring its absorbance at 260 and 280 nm.

Quantitative Real-Time (qRT-PCR) Analysis. Isolated RNA can then be used for cDNA synthesis using TAQMAN® Reverse Transcription Reagents (Applied Biosystems, Cat #N8080234) followed by real-time PCR analysis by the 7900HT Fast Real-Time PCR System using Human Immune Array (Applied Biosystems, Cat#4370573) and Human MicroRNA Array (Applied Biosystems, Cat#4384792).

Lenalidomide and pomalidomide are chemical analogs of thalidomide with enhanced anti-cancer and anti-inflammatory activities. To study if lenalidomide and pomalidomide could enhance PINK cell cytotoxicity, ex vivo cultured (day 19) PINK cells were pre-treated with lenalidomide or pomalidomide for 24 hours followed by co-culturing with target colorectal carcinoma cell line HCT-116. Lenalidomide-treated NK cells demonstrated 42.1% cytotoxicity and pomalidomide-treated NK cells showed 47A % cytotoxicity, while control untreated PINK cells showed only 24.3% cytotoxicity.

Quantitative real-time PCR (qRT-PCR) and flow cytometry analyses showed that the pomalidomide-elicited enhancement of NK cell cytotoxicity was correlated with increased granzyme B (GZMB) gene expression (60%±1.7% increase) (Table 11) and increased percentage of GZMB-positive NK cells (25% increase). In addition, expression of GM-CSF was increased in lenalidomide (232%±1.6% increase) and pomalidomide (396%±0.3% increase)-treated PINK cells (Table 11A, 11B).

Table 11A, 11B. qRT-PCT analysis of lenalidomide- and pomalidomide-treated cultured PINK cells compared to untreated cells. 11A: Fold change of gene expression between lenalidomide-treated and lenalidomide-untreated samples for genes listed. The paired t-test is used to determine if fold changes are equal in lenalidomide-treated and -untreated samples. 11B: Fold change of gene expression between pomalidomide-treated and pomalidomide-untreated samples for 25 genes listed. The paired t-test is used to determine if fold changes are equal in treated and untreated samples.

TABLE 11A

|  | Veh | Len. | Veh-stdev | Len.-stdev | P Value |
|---|---|---|---|---|---|
| BAX | 1 | 1.38 | 0.06 | 0.02 | 0.05 |
| CCL5 | 1 | 1.24 | 0.11 | 0.07 | 0.04 |
| CCR5 | 1 | 0.9 | 0.07 | 0.08 | 0.02 |
| CD68 | 1 | 4.04 | 0.05 | 0.13 | 0.01 |
| CD8A | 1 | 1.3 | 0.01 | 0.02 | 0.02 |
| CSF2 | 1 | 2.32 | 0.14 | 0.02 | 0.02 |
| FAS | 1 | 1.11 | 0.02 | 0.04 | 0.04 |
| GUSB | 1 | 1.13 | 0.04 | 0.07 | 0.05 |
| IL2RA | 1 | 1.26 | 0.03 | 0.01 | 0.03 |
| TNFRSF18 | 1 | 0.7 | 0.1 | 0.16 | 0.04 |

BAX—BCL2-associated X protein
CCL5—chemokine (C-C motif) ligand 5
CCR5—chemokine (C-C motif) receptor 5
CSF2—colony stimulating factor 2 (granulocyte-macrophage)
FAS—TNF receptor superfamily, member 6
GUSB—β glucuronidaseβ
IL2RA—α interleukin 2 receptor
TNFRSF18—tumor necrosis factor receptor superfamily, member 18

TABLE 11B

|  | Veh | Pom. | Veh-stdev | Pom.-stdev | P Value |
|---|---|---|---|---|---|
| ACTB | 1 | 0.77 | 0.01 | 0 | 0.01 |
| BAX | 1 | 2.23 | 0.06 | 0 | 0.01 |
| CCL2 | 1 | 5.46 | 0.01 | 0.37 | 0.02 |
| CCL3 | 1 | 2.2 | 0.04 | 0.16 | 0.02 |
| CCL5 | 1 | 1.78 | 0.11 | 0.04 | 0.02 |
| CCR5 | 1 | 0.68 | 0.07 | 0 | 0.05 |
| CD68 | 1 | 8.74 | 0.05 | 0.19 | 0 |
| CD80 | 1 | 1.59 | 0.13 | 0.19 | 0.02 |
| CD8A | 1 | 2.39 | 0.01 | 0.08 | 0.01 |
| CSF1 | 1 | 1.41 | 0.07 | 0.05 | 0.01 |
| CSF2 | 1 | 3.96 | 0.14 | 0 | 0.01 |
| ECE1 | 1 | 1.56 | 0.06 | 0.12 | 0.02 |
| FAS | 1 | 1.34 | 0.02 | 0.03 | 0.01 |
| GNLY | 1.01 | 1.96 | 0.18 | 0.02 | 0.05 |
| GUSB | 1 | 1.76 | 0.04 | 0.01 | 0.01 |
| GZMB | 1 | 1.59 | 0.06 | 0.02 | 0.03 |
| IL10 | 1.02 | 1.52 | 0.31 | 0.22 | 0.04 |
| IL1A | 1.01 | 2.61 | 0.19 | 0.12 | 0.01 |
| IL2RA | 1 | 1.58 | 0.03 | 0.06 | 0.01 |
| IL8 | 1 | 1.62 | 0.04 | 0.06 | 0.04 |
| LTA | 1 | 2.88 | 0.02 | 0.21 | 0.02 |
| PRF1 | 1 | 1.17 | 0.07 | 0.1 | 0.05 |
| PTGS2 | 1 | 1.68 | 0.01 | 0.05 | 0.02 |
| SKI | 1 | 1.96 | 0.04 | 0.02 | 0.01 |
| TBX21 | 1.01 | 2.05 | 0.14 | 0.2 | 0.01 |

ACTB—β-actin
BAX—BCL2-associated X protein
CCL2—chemokine (C-C motif) ligand 2
CCL3—chemokine (C-C motif) ligand 3
CCL5—chemokine (C-C motif) ligand 5
CCR5—chemokine (C-C motif) receptor 5
CSF1—colony stimulating factor 1 (macrophage)
CSF2—colony stimulating factor 2 (granulocyte-macrophage)
ECE1—endothelin converting enzyme 1
FAS—TNF receptor superfamily, member 6
GNLY—granulysin
GUSB—glucuronidase-β
GZMB—granzyme B (granzyme 2, cytotoxic T-lymphocyte-associated serine esterase 1)
IL1A—α interleukin 1
IL2RA—interleukin 2 receptor-α
IL8—interleukin 8
IL10—interleukin 10
LTA—lymphotoxin α (TNF superfamily, member 1)
PRF1—perforin 1 (pore forming protein)
PTGS2—prostaglandin-endoperoxide synthase 2 (prostaglandin G/H synthase and cyclooxygenase)
SKI—v-ski sarcoma viral oncogene homolog (avian)
TBX21—T-box21

Cytotoxicity of Combined Natural Killer Cells

In a separate cytotoxicity assay, cultured NK cells derived from donor matched umbilical cord blood and placental perfusate were effector cells, while tumor cells were target cells. Tumor cells were labeled with PKH26 (Sigma-Aldrich Catalog #PKH26-GL) (see, e.g., Lee-MacAry et al., *J. Immunol. Meth.* 252(1-2):83-92 (2001)), which inserts into cell plasma membrane due to its lipophilic aliphatic residue, then placed in 96-well U-bottom tissue culture plates and incubated with cultured NK cells at various effector-target (E:T) ratios in 200 µl RPMI 1640 supplemented with 10% FBS. Cultures were incubated for 4 h at 37° C. in 5% $CO_2$. After incubation, cells were harvested and TO-PRO-3 (Invitrogen Catalog #T3605), a membrane-impermeable DNA stain, was added to cultures to 1 µM final concentration followed by FACS analysis using BD FACSCanto. Cytotoxicity was expressed as percentage of dead cell ($PKH26^+TO-PRO-3^+$) within the total $PKH26^+$ target tumor cells.

In this cytotoxicity assay, human chronic myeloid lymphoma (CML) K562 cells were labeled with PKH26, which inserts into cell plasma membrane, and placed in 96-well U-bottomed tissue culture plates. Placental (combo) or peripheral blood NK cells cultured for 21 days were mixed with K562 cells at effector to target (E:T) ratios of 10:1, 5:1, 2.5:1 and 1.25:1 in RPMI 1640 supplemented with 10% v/v FBS. After a 4 hour incubation time, cells were harvested and TO-PRO-3 was added to cell cultures followed by flow cytometry for the presence of PKH26 and TO-PRO-3. Cytotoxicity was expressed as percentage of $PKH26^+TO-PRO-3^+$ dead cells within the total $PM-126^+$ target tumor cells. Both placental NK cells and peripheral blood NK cells showed substantial toxicity towards K562 cells at all E:T ratios tested (FIG. 4). Significantly higher toxicity of placental NK cells than peripheral blood NK cells towards K562 cells was observed at two E:T ratios, 10:1 and 5:1 (FIG. 4).

6.4. Example 4

Cytotoxicity of Human Placental Perfusate Towards Tumor Cells

This Example demonstrates that human placental perfusate cells are cytotoxic to tumor cells, and that the cytotoxicity of total nucleated cells from HPP (TNC-HPP) on KG-1a was higher than that of TNC from matched UCB. Total nucleated cells from HPP or umbilical cord blood (UCB) were mixed with KG-1a cells at ratios of 1:1, 5:1, 10:1, 20:1 or 100:1. After 24 h or 48 h incubation, cells were harvested and examined for the presence of CFSE by FACS analysis (BD FACSCanto, BD Bioscience). Tumor cells cultured alone were used as controls. Cytotoxicity was defined as: (1-CFSE$_{Sample}$/CFSE$_{Control}$)*100%. Significant cytotoxicity was shown at the 100:1 ratio. See FIG. 5.

In a separate experiment, the cytotoxicity of total nucleated cells from HPP was compared to that of total nucleated cells from umbilical cord blood. Matched TNC-HPP or UCB was mixed with KG-1a cells at ratios of 0.78:1, 1.56:1, 3.12:1, 6.25:1, 12.5:1, 25:1, 50:1 or 100:1. TNC-HPP showed consistently higher cytotoxicity at all ratios compared to that of UCB. See FIG. 6.

In another experiment, 24 hours prior to incubation with KG-1a cells, TNC-HPP was stimulated with 100 U/mL, or 1000 U/mL of IL-2, while HPP cultured with RPMI medium was used as control. At a ratio of 6.25 NK cells per KG-1a cells and above, IL-2 appears to increase the cytotoxicity of the TNC-HPP. See FIG. 7.

The experiments were repeated using a broader array of tumor cell types, as shown in Table 12, using 5×10$^5$ HPP cells and 1×10$^4$ tumor cells.

TABLE 12

Tumor Cell Types Tested for Cytotoxic Effect of Placental Perfusate

| | |
|---|---|
| HCC2218 | Human primary ductal carcinoma |
| CCRF-CEM | Human leukemia |
| J.RT3-T3.5 | Human acute T cell leukemia |
| K562 | Human chronic myeloid lymphoma (CML) |
| KG-1 | Human acute myelogenous leukemia |
| KG-1a | Human acute myelogenous leukemia (AML) |
| KU812 | Human leukemia (CML) |
| NCI-H1417 | Human lung carcinoma |
| SNU-CI | Human colon adenocarcinoma |
| U-937 | Human histiocytic lymphoma |
| WERI-RB-1 | Human retinoblastoma |
| HCT-116 | Human colorectal carcinoma |
| HT-29 | Human colorectal adenocarcinoma |
| U266 | Human myeloma |

When HPP cells and tumor cells were co-cultured for 24 hours or 48 hours at a 50:1 ratio, the HPP cells showed substantial toxicity towards the tumor cells. For both times, co-culture resulted in the death of over 50% of the tumor cells. See FIGS. 8A and 8B.

6.5. Example 5

Cytokine Production by Human Placental Perfusate Cells During Exposure to Tumor Cells To determine the primary mechanism of action responsible for mediating the potent anti-leukemic effects of HPP cells, the cytokine release profile of HPP cells cocultured with tumor cell lines was analyzed, and compared to that of UCB cells, at different time points by multiplexed Luminex assay.

Supernatants collected post-incubation were subjected to Luminex assay to determine the concentrations of IFN-γ, TNF-α, and GM-CSF (Cat#HCYTO-60K-03, Millipore). These three cytokines are related with NK cytotoxicity. (See, e.g., Imai et al., *Blood* 2005. 106(1):376-83.). Quantitative RT-PCR was also performed to examine the expression of IFN-γ, TNF-α, and GM-CSF using Applied Biosystems FAST 7900HT instrument and primers. Culture conditions were the same as for the co-culture cytotoxicity assays described above. Concentrations of cytokines were determined using a Luminex assay.

Secretion of IFN-γ, TNF-α, and GM-CSF from HPP cells cocultured with tumor cells was determined to be significantly higher than that of UCB cells. In one experiment, HPP cells were mixed with KG-1a cells at ratios of 0.78:1, 1.56:1, 3.12:1, 6.25:1, 12.5:1, 25:1, 50:1 or 100:1, in the presence or absence of 100 U IL-2. TNC-HPP showed consistently increased production of IFN-γ in the presence of IL-2 compared to the absence of IL-2. IFN-γ levels at 24 h were determined to increase about 5-26 fold (median: 16 fold); at 48 h around 3~65 fold (median: 27 fold), which was consistent with the results from cytotoxicity study. See FIG. 9.

In another experiment, 24 hours prior to incubation with KG-1a cells, TNC-HPP was stimulated with 100 U/mL, or 1000 U/mL of IL-2, while HPP cultured with RPMI media was used as control. HPP or matched UCB cells were incubated 24 h with or without IL-2, before cocultured with KG-1a cells. The secretion of IFN-γ was most increased in HPP cells cocultured with K562 and KG-1a at 48 h. When HPP cells were treated with 100 U/mL IL-2, the cytotoxicity of HPP cells on KG-1a at 24 h and 48 h was increased. The secretion level of IFN-γ in MPP cells was higher than that of the matched UCB cells upon IL-2 treatment. Higher expression of IFN-γ was confirmed by RT-PCR analysis of cells from matched HPP and UCB. These results show that HPP cells exhibit higher anti-leukemic activity as compared to UCB cells and this higher activity is associated with a significant increase in IFN-γ production.

IFN-γ production in HPP cells, and in umbilical cord blood cells, during co-culture with a panel of tumor cell lines was analyzed using the tumor cells lines listed in Table 1, above. HPP cells and tumor cells were co-cultured for 24 hours or 48 hours at a ratio of 50:1, using 10$^4$ tumor cells and 5×10$^5$ HPP cells. For CCRF-CEM, J.RT3-T3.5, K562, KG1, KG-1a, KU812, NC1-H1417, U-937 and WER1-RB-1 cell lines, the increase in IFN-γ production in HPP cells at 24 hours co-culture exceeded that of umbilical cord blood cells co-cultured with these cell lines for the same time. See FIG. 10A. At 48 hours co-culture, the increase in IFN-γ production in HPP cells exceeded that of umbilical cord blood for all tumor cell lines. See FIG. 10B. Of the tumor cell lines, K562 cells induced the greatest increase in IFN-γ production in HPP cells at both 24 hours and 48 hours. Similar results were observed for TNF-α and GM-CSF.

Cell cycle analysis demonstrated that the percentage of KG-1a in S phase decreased 30% when cocultured with HPP as compared to KG-1a cells cultured alone. Further coculture experiments performed using different enriched fractions of HPP demonstrated that the anti-leukemic activity of HPP was largely attributed to the high concentration of unique immature natural killer cells characterized by high expression of CD56$^+$, lack of expression of CD16.

6.6. Example 6

Suppression of Tumor Cell Proliferation In Vivo by Human Placental Perfusate Cells 6.6.1. Materials & Methods This Example demonstrates the effectiveness of human placental perfusate in vivo against tumor cells using a NOD/SCID mouse xenograft tumor model.

Culturing of KG-1 Cells. KG-1 cells were maintained in Iscove's modified Dulbecco's medium supplemented with 20% of fetal bovine serum (growth medium) at 37° C. in 95% air/5% CO$_2$ and 100% humidity. Medium in the culture was changed every other day and cells were passaged weekly. KG-1 cells grow as suspensions. Therefore, for changing medium or passaging cells, the cell suspensions were collected in centrifuge tubes and centrifuged at 2,000 rpm for 10 min in a SORVALL® HERAEUS® rotor (part no.

75006434). The supernatant was discarded and an appropriate amount of the cell pellet was resuspended in the growth medium for continuation of culturing.

KG-1 Cell Preparation for Implantation. For cell implantation to mice, cells were harvested by centrifugation as described above. Cell pellets were collected and re-suspended in phosphate buffered saline. To determine the number of cells to be implanted to the mice, an aliquot of the cell suspension was counted using a hemacytometer. Trypan Blue dye was used to exclude the non-viable cells in the suspension.

HPP Cell Preparation for Implantation. For HPP storage and thawing, samples were received frozen in a dry shipper container in good condition. The units were stored in the dry shipping container until thawing on Feb. 7, 2007. On the day of thawing, HPP units were removed from the cryofreezer (one at a time) and placed into ziptop plastic bags. The bags were then placed into a 37° C. water bath with gentle agitation until mostly thawed (a small frozen piece remaining in the bag). The bags were then removed from the water bath, the units were removed from the zip-top bags, and the units were gently inverted until completely thawed. The units were then placed into a laminar flow hood and the outer surface of the blood bag was sterilized by spraying with 70% ethanol. Blood bags were cut open using sterile scissors, and cells were transferred to sterile 50 ml conical tubes (1 tube for each HPP unit; 2 tubes for each UCB unit) by sterile pipette. Next, 10 mL thawing buffer (2.5% human albumin, 5% dextran 40) was slowly added to each tube with gentle mixing (over a period of 2.2-2.9 minutes). Each blood bag was then rinsed with 10 mL thawing buffer, which was then slowly added to the 50 ml conical tube (over a period of 0.7-1.3 min).

After thawing, each unit was stored on wet ice prior to centrifugation. All tubes were centrifuged for 10 min (440×g at 10° C.), supernatants were aspirated using sterile pipettes, and pellets were gently disrupted by shaking the tube. A 1-ml aliquot of vehicle (PBS+1% fetal calf serum) was added to one of the tubes, and the tube was mixed by gentle swirling. Using a 2-ml pipette, the contents were transferred to a second tube and then to a third tube and then a fourth tube. The emptied tubes were washed with 0.2 ml dilution buffer.

For cell counting, a 25 µl aliquot of was transferred to a 15 ml conical tube containing 975 µl vehicle on ice. Erythrocytes were then lysed by adding 4 ml cold ammonium chloride lysis reagent and incubating on ice for 10 min. After incubation, 5 ml cold PBS was added to each tube and the tubes were centrifuged (10 min, 400×g, 10° C.). After RBC lysis, cells were counted by hemacytometer, using trypan blue to assess viability. Counting results were corrected for dilution and then divided by a lysis factor (0.46) to estimate the number of cells present before RBC lysis.

For HPP dose preparation, after counting, HPP cells were diluted to $1\times10^8$ cells/ml by adding vehicle. MPP cells were then stored on ice until syringes were loaded. The elapsed time between thawing the first unit and completion of dose preparation was less than 3 hours.

Before filling syringes, a 50 µl aliquot of the dosing material was set aside for post-dose verification by counting as described above. After dosing, remaining dose material was assessed for dose verification.

Study Design. On Day 1, twenty-four NOD/SCID male mice (Jackson Laboratories) were implanted with 5 million viable KG-1 cells S/C at the flank region. The mice were separated such that four to five mice were housed in a micro-isolation cage system with wood chip bedding. Sterilized rodent feed and water was provided ad libitum. The mice were closely monitored twice a week for tumor growth. The first measurable tumor was observed on Day 25. Body weights were then recorded once a week and tumor measurements recorded twice a week with a caliper. On Day 52 post-implantation, the animals were randomized into three separate groups, with tumor volumes averaging about 300-350 mm³. See Table 13, below. The first group consisted of four control mice with an average tumor volume of 312 mm³. Two of these mice were implanted intravenously (IV), and two intra-tumorally (IT), with 200 µl and 50 µl of a vehicle solution, respectively. The second group with an average tumor volume of 345 mm³ consisted of four mice implanted intravenously with 200 µl of HPP cells per mouse ($2\times10^7$ cells). The last group, implanted IT with 50 µl of HPP cells per mouse also consisted of four mice with an average tumor volume of 332 mm³.

TABLE 13

Experimental groups for in vivo tumor suppression experiment.

| Animal # | HPP Treatment Group | Tumor Volume On Day of HPP Implantation |
|---|---|---|
| Group 1 (Control) | | |
| 1 | IV 1 | 457 |
| 2 | IT 2 | 429 |
| 3 | IT 3 | 214 |
| 4 | IV 4 | 147 |
| | Mean: | 312 |
| Group 2 (IV Cell Implantation) | | |
| 5 | 1 | 466 |
| 6 | 2 | 209 |
| 7 | 3 | 217 |
| 8 | 4 | 487 |
| | Mean: | 345 |
| Group 3 (IT Cell Implantation) | | |
| 9 | 1 | 491 |
| 10 | 2 | 256 |
| 11 | 3 | 296 |
| 12 | 4 | 285 |
| | Mean: | 332 |

IV—200 µL implantation; IT—50 µL implantation.

On Day 66, 14 days after the implantation of HPP cells, the study was terminated due to high tumor volumes.

6.6.2. Results

The tumor volumes (TV) were measured until Day 66 (day 14 post HPP-cell implantation) when the TV of the control group reached an average of 2921 mm³. The IV treatment group at the end of study had an average TV of 2076 mm³, and the IT group had a TV of 2705 mm³. With respect to % increase in the TV post-treatment, the IT group showed a modest 20% inhibition whereas the IV group showed more than 35% inhibition of tumor growth compared to the control group. Inhibition in the IT group was demonstrable. See FIG. 11.

Equivalents

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes. The citation of any publication is for its disclosure prior to the filing date and should not be construed as an admission that the present invention is not entitled to antedate such publication by virtue of prior invention.

What is claimed is:

1. A method of treating an individual having tumor cells, comprising administering to said individual a therapeutically effective amount of human placental perfusate cells, wherein said placental perfusate cells comprise CD56$^+$ placental intermediate natural killer cells.

2. The method of claim 1, wherein the tumor cells are blood cancer cells.

3. The method of claim 1, wherein the tumor cells are solid tumor cells.

4. The method of claim 1, wherein the tumor cells are primary ductal carcinoma cells, leukemia cells, acute T cell leukemia cells, chronic myeloid lymphoma (CML) cells, acute myelogenous leukemia cells, chronic myelogenous leukemia (CML) cells, lung carcinoma cells, colon adenocarcinoma cells, histiocytic lymphoma cells, colorectal carcinoma cells, colorectal adenocarcinoma cells, or retinoblastoma cells.

5. The method of claim 1, wherein said perfusate comprises a culture medium.

6. The method of claim 1, wherein said perfusate has been treated to remove a plurality of erythrocytes.

7. The method of claim 1, wherein said placental intermediate natural killer cells are administered intravenously.

8. The method of claim 1, wherein said plurality of placental perfusate cells are total nucleated cells from placental perfusate.

9. The method of claim 1, wherein said placental perfusate cells comprise at least about 50% CD56$^+$ placental cells.

10. A method of treating an individual comprising tumor cells comprising administering to said individual a therapeutically effective amount of CD56+, CD16− placental intermediate natural killer cells.

11. The method of claim 10, wherein said tumor cells are primary ductal carcinoma cells, leukemia cells, acute T cell leukemia cells, chronic myeloid lymphoma (CML) cells, acute myelogenous leukemia cells, chronic myelogenous leukemia (CML) cells, lung carcinoma cells, colon adenocarcinoma cells, histiocytic lymphoma cells, multiple myeloma cells, colorectal carcinoma cells, colorectal adenocarcinoma cells, or retinoblastoma cells.

12. The method of claim 10, wherein said placental intermediate natural killer cells are contacted with an immunomodulatory compound in an amount and for a time sufficient for said placental intermediate natural killer cells to express detectably more granzyme B than an equivalent number of placental intermediate natural killer cells not contacted with said immunomodulatory compound.

13. The method of claim 12, wherein said immunomodulatory compound is lenalidomide or pomalidomide.

14. A method of treating an individual having tumor cells, comprising administering to said individual a therapeutically effective amount of combined natural killer cells, wherein said combined natural killer cells comprise placental intermediate natural killer cells isolated from placental perfusate and natural killer cells isolated from umbilical cord blood, and wherein said umbilical cord blood is isolated from the placenta from which said placental perfusate is obtained.

15. The method of claim 14, wherein said tumor cells are primary ductal carcinoma cells, leukemia cells, acute T cell leukemia cells, chronic myeloid lymphoma (CML) cells, acute myelogenous leukemia cells, chronic myelogenous leukemia (CML) cells, lung carcinoma cells, colon adenocarcinoma cells, histiocytic lymphoma cells, multiple myeloma cells, colorectal carcinoma cells, colorectal adenocarcinoma cells, or retinoblastoma cells.

16. The method of claim 14, wherein said combined natural killer cells comprise:
   a detectably higher number of CD3−CD56+CD16− natural killer cells than an equivalent number of natural killer cells from peripheral blood;
   a detectably lower number of CD3−CD56+CD16+ natural killer cells than an equivalent number of natural killer cells from peripheral blood;
   a detectably higher number of CD3−CD56+KIR2DL2/L3+ natural killer cells than an equivalent number of natural killer cells from peripheral blood;
   a detectably lower number of CD3−CD56+NKp46+ natural killer cells than an equivalent number of natural killer cells from peripheral blood;
   a detectably higher number of CD3−CD56+NKp30+ natural killer cells than an equivalent number of natural killer cells from peripheral blood;
   a detectably higher number of CD3−CD56+2B4+ natural killer cells than an equivalent number of natural killer cells from peripheral blood; or
   a detectably higher number of CD3−CD56+CD94+ natural killer cells than an equivalent number of natural killer cells from peripheral blood.

17. The method of claim 16, wherein said natural killer cells have not been cultured.

18. The method of claim 14, wherein said combined natural killer cells comprise:
   a detectably lower number of CD3⁻CD56⁺KIR2DL2/L3⁺ natural killer cells than an equivalent number of natural killer cells from peripheral blood;
   a detectably higher number of CD3⁻CD56⁺NKp46⁺ natural killer cells than an equivalent number of natural killer cells from peripheral blood;
   a detectably higher number of CD3⁻CD56⁺NKp44⁺ natural killer cells than an equivalent number of natural killer cells from peripheral blood; or
   a detectably higher number of CD3⁻CD56⁺NKp30⁺ natural killer cells than an equivalent number of natural killer cells from peripheral blood.

19. The method of claim 18, wherein said natural killer cells have been cultured.

20. The method of claim 19, wherein said natural killer cells have been cultured for about 21 days.

21. The method of claim 1, wherein said placental perfusate cells comprise at least about 50% CD56⁺, CD16⁻ placental intermediate natural killer cells.

22. The method of claim 10, wherein said placental perfusate cells comprise at least about 50% CD56⁺, CD16⁻ placental intermediate natural killer cells.

23. The method of claim 1, wherein said placental intermediate natural killer cells express one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p, hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, or hsa-miR-99a at a detectably higher level than peripheral blood natural killer cells.

24. The method of claim 10, wherein said placental intermediate natural killer cells express one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p, hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, or hsa-miR-99a at a detectably higher level than peripheral blood natural killer cells.

25. The method of claim 14, wherein said placental intermediate natural killer cells express one or more of the microRNAs hsa-miR-100, hsa-miR-127, hsa-miR-211, hsa-miR-302c, hsa-miR-326, hsa-miR-337, hsa-miR-497, hsa-miR-512-3p, hsa-miR-515-5p , hsa-miR-517b, hsa-miR-517c, hsa-miR-518a, hsa-miR-518e, hsa-miR-519d, hsa-miR-520g, hsa-miR-520h, hsa-miR-564, hsa-miR-566, hsa-miR-618, or hsa-miR-99a at a detectably higher level than peripheral blood natural killer cells.

26. The method of claim 1, wherein said placental intermediate natural killer cells express one or more of aminopeptidase N protein, apolipoprotein E protein, atrophin-1 interacting protein 1, innexin inx-3 protein, integrin alpha-2 precursor protein, integrin beta-5 precursor, mast cell surface glycoprotein GP49B precursor protein, or ryanodine receptor 1 protein; and do not express one or more of fibroblast growth factor receptor 4 precursor protein, immunity-associated nucleotide 4-like protein, integrin alpha-L precursor protein, integrin beta 2 precursor protein, integrin beta 4 precursor protein, membrane-bound lytic murein transglycosylase D precursor protein, oxysterol binding protein-related protein 8, or perforin 1 precursor 1 protein.

27. The method of claim 10, wherein said placental intermediate natural killer cells express one or more of aminopeptidase N protein, apolipoprotein E protein, atrophin-1 interacting protein 1, innexin inx-3 protein, integrin alpha-2 precursor protein, integrin beta-5 precursor, mast cell surface glycoprotein GP49B precursor protein, or ryanodine receptor 1 protein; and do not express one or more of fibroblast growth factor receptor 4 precursor protein, immunity-associated nucleotide 4-like protein, integrin alpha-L precursor protein, integrin beta 2 precursor protein, integrin beta 4 precursor protein, membrane-bound lytic murein transglycosylase D precursor protein, oxysterol binding protein-related protein 8, or perforin 1 precursor 1 protein.

28. The method of claim 14, wherein said placental intermediate natural killer cells express one or more of aminopeptidase N protein, apolipoprotein E protein, atrophin-1 interacting protein 1, innexin inx-3 protein, integrin alpha-2 precursor protein, integrin beta-5 precursor, mast cell surface glycoprotein GP49B precursor protein, or ryanodine receptor 1 protein; and do not express one or more of fibroblast growth factor receptor 4 precursor protein, immunity-associated nucleotide 4-like protein, integrin alpha-L precursor protein, integrin beta 2 precursor protein, integrin beta 4 precursor protein, membrane-bound lytic murein transglycosylase D precursor protein, oxysterol binding protein-related protein 8, or perforin 1 precursor 1 protein.

29. The method of claim 1, additionally comprising administering to said individual an anti-cancer agent.

30. The method of claim 10, additionally comprising administering to said individual an anti-cancer agent.

31. The method of claim 14, additionally comprising administering to said individual an anti-cancer agent.

* * * * *

```
                              SEQUENCE LISTING

<160> NUMBER OF SEQ ID NOS: 20

<210> SEQ ID NO 1
<211> LENGTH: 22
<212> TYPE: RNA
<213> ORGANISM: Homo sapiens

<400> SEQUENCE: 1
aacccguaga uccgaacuug ug                                                  22

<210> SEQ ID NO 2
<211> LENGTH: 22
<212> TYPE: RNA
<213> ORGANISM: Homo sapiens

<400> SEQUENCE: 2
ucggauccgu cugagcuugg cu                                                  22

<210> SEQ ID NO 3
<211> LENGTH: 22
<212> TYPE: RNA
<213> ORGANISM: Homo sapiens

<400> SEQUENCE: 3
uucccuuugu cauccuucgc cu                                                  22

<210> SEQ ID NO 4
<211> LENGTH: 23
<212> TYPE: RNA
<213> ORGANISM: Homo sapiens

<400> SEQUENCE: 4
uaagugcuuc cauguuucag ugg                                                 23

<210> SEQ ID NO 5
<211> LENGTH: 20
<212> TYPE: RNA
<213> ORGANISM: Homo sapiens

<400> SEQUENCE: 5
ccucugggcc cuuccuccag                                                     20

<210> SEQ ID NO 6
<211> LENGTH: 23
<212> TYPE: RNA
<213> ORGANISM: Homo sapiens

<400> SEQUENCE: 6
uccagcuccu auaugaugcc uuu                                                 23

<210> SEQ ID NO 7
<211> LENGTH: 21
<212> TYPE: RNA
<213> ORGANISM: Homo sapiens

<400> SEQUENCE: 7
cagcagcaca cuguggguuug u                                                  21

<210> SEQ ID NO 8
<211> LENGTH: 22
<212> TYPE: RNA
```

```
<213> ORGANISM: Homo sapiens

<400> SEQUENCE: 8
aagugcuguc auagcugagg uc                                          22

<210> SEQ ID NO 9
<211> LENGTH: 24
<212> TYPE: RNA
<213> ORGANISM: Homo sapiens

<400> SEQUENCE: 9
uucuccaaaa gaaagcacuu ucug                                        24

<210> SEQ ID NO 10
<211> LENGTH: 22
<212> TYPE: RNA
<213> ORGANISM: Homo sapiens

<400> SEQUENCE: 10
ucgugcaucc cuuuagagug uu                                          22

<210> SEQ ID NO 11
<211> LENGTH: 22
<212> TYPE: RNA
<213> ORGANISM: Homo sapiens

<400> SEQUENCE: 11
aucgugcauc cuuuuagagu gu                                          22

<210> SEQ ID NO 12
<211> LENGTH: 21
<212> TYPE: RNA
<213> ORGANISM: Homo sapiens

<400> SEQUENCE: 12
aaagcgcuuc ccuuugcugg a                                           21

<210> SEQ ID NO 13
<211> LENGTH: 21
<212> TYPE: RNA
<213> ORGANISM: Homo sapiens

<400> SEQUENCE: 13
aaagcgcuuc ccuucagagu g                                           21

<210> SEQ ID NO 14
<211> LENGTH: 22
<212> TYPE: RNA
<213> ORGANISM: Homo sapiens

<400> SEQUENCE: 14
caaagugccu cccuuuagag ug                                          22

<210> SEQ ID NO 15
<211> LENGTH: 24
<212> TYPE: RNA
<213> ORGANISM: Homo sapiens

<400> SEQUENCE: 15
acaaagugcu ucccuuuaga gugu                                        24

<210> SEQ ID NO 16
<211> LENGTH: 22
```

```
<212> TYPE: RNA
<213> ORGANISM: Homo sapiens

<400> SEQUENCE: 16
acaaagugcu ucccuuuaga gu                                            22

<210> SEQ ID NO 17
<211> LENGTH: 19
<212> TYPE: RNA
<213> ORGANISM: Homo sapiens

<400> SEQUENCE: 17
aggcacggug ucagcaggc                                                19

<210> SEQ ID NO 18
<211> LENGTH: 19
<212> TYPE: RNA
<213> ORGANISM: Homo sapiens

<400> SEQUENCE: 18
gggcgccugu gaucccaac                                                19

<210> SEQ ID NO 19
<211> LENGTH: 23
<212> TYPE: RNA
<213> ORGANISM: Homo sapiens

<400> SEQUENCE: 19
aaacucuacu uguccuucug agu                                           23

<210> SEQ ID NO 20
<211> LENGTH: 22
<212> TYPE: RNA
<213> ORGANISM: Homo sapiens

<400> SEQUENCE: 20
aacccguaga uccgaucuug ug                                            22
```